United States Patent
Kaplan et al.

(10) Patent No.: US 6,916,933 B2
(45) Date of Patent: Jul. 12, 2005

(54) 4-PYRIDINYL-N-ACYL-L-PHENYLALANINES

(75) Inventors: Gerald Lewis Kaplan, New York, NY (US); Achyutharao Sidduri, Livingston, NJ (US); Jefferson Wright Tilley, North Caldwell, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 170 days.

(21) Appl. No.: 10/670,182

(22) Filed: Sep. 24, 2003

(65) Prior Publication Data

US 2004/0127706 A1 Jul. 1, 2004

Related U.S. Application Data

(60) Continuation of application No. 10/059,618, filed on Jan. 29, 2002, now abandoned, which is a division of application No. 09/717,684, filed on Nov. 21, 2000, now Pat. No. 6,388,084.
(60) Provisional application No. 60/245,603, filed on Nov. 3, 2000, and provisional application No. 60/169,090, filed on Dec. 6, 1999.

(51) Int. Cl.$^7$ .................... C07D 213/70; C07D 211/72; C07D 417/00; C07D 401/00; C07D 405/00
(52) U.S. Cl. .................... 546/291; 546/300; 546/268.7; 546/269.7; 546/269.1; 546/271.1; 546/271.4; 546/272.1; 546/272.4; 546/272.7; 546/276.4; 546/280.1; 546/280.4; 546/282.1; 546/301; 546/303; 546/194; 544/66; 544/131; 544/360
(58) Field of Search .................... 546/272.4, 276.4, 546/291, 300, 303, 268.7, 269.1, 271.1, 271.4, 269.7, 280.4, 280.1, 282.1, 272.7, 301; 544/66, 131

(56) References Cited

FOREIGN PATENT DOCUMENTS

| EP | 2 354 440 | 3/2001 |
|---|---|---|
| WO | 98 53814 | 12/1998 |
| WO | 98 53817 | 12/1998 |
| WO | 99 10312 | 3/1999 |
| WO | 99 10313 | 3/1999 |
| WO | 99 26921 | 6/1999 |
| WO | WO 99/26923 | 6/1999 |
| WO | 99 36393 | 7/1999 |
| WO | 99 37618 | 7/1999 |
| WO | 99 43642 | 9/1999 |
| WO | WO 99/64390 | 12/1999 |
| WO | 99 64395 | 12/1999 |
| WO | 00 37429 | 6/2000 |
| WO | 00 43354 | 7/2000 |
| WO | 00 48988 | 8/2000 |
| WO | 00 48994 | 8/2000 |
| WO | WO 01/12183 A1 | 2/2001 |

OTHER PUBLICATIONS

Tilley et. al., "Biphenylcarboxamide Derivatives as Antagonists of Platelet–Activating Factor", J. Med. Chem. 32, 1814–1820.*

Ca 89:5710 reference, "Substituent effect on selectivity in photoisomerization of 4–pyrones and 4–pyridones", p. 492, 1978.

* cited by examiner

Primary Examiner—Johann Richter
Assistant Examiner—Binta Robinson
(74) Attorney, Agent, or Firm—George W. Johnston; Dennis P. Tramaloni

(57) ABSTRACT

Compounds of Formula I have activity as inhibitors of binding between VCAM-1 and cells expressing VLA-4 and are useful for treating disease whose symptoms and or damage are related to the binding of VCAM-1 to cells expressing VLA-4.

61 Claims, No Drawings

4-PYRIDINYL-N-ACYL-L-PHENYLALANINES

This application is a Continuation of Ser. No. 10/059,618, filed Jan. 29, 2002, now abandoned, which claims priority under 35 U.S.C. § 119(e) of Ser. No. 09/717,684, filed Nov. 21, 2000, now U.S. Pat. No. 6,388,084, which is a non-provisional application of Ser. No. 60/169,090, filed Dec. 6, 1999, and Ser. No. 60/245,603, filed Nov. 3, 2000.

BACKGROUND OF THE INVENTION

Vascular cell adhesion molecule-1 (VCAM-1), a member of the immunoglobulin (Ig) supergene family, is expressed on activated, but not resting, endothelium. The integrin VLA-4 ($\alpha_4\beta_1$), which is expressed on many cell types including circulating lymphocytes, eosinophils, basophils, and monocytes, but not neutrophils, is the principal receptor for VCAM-1. Antibodies to VCAM-1 or VLA-4 can block the adhesion of these mononuclear leukocytes, as well as melanoma cells, to activated endothelium in vitro. Antibodies to either protein have been effective at inhibiting leukocyte infiltration and preventing tissue damage in several animal models of inflammation. Anti-VLA-4 monoclonal antibodies have been shown to block T-cell emigration in adjuvant-induced arthritis, prevent eosinophil accumulation and bronchoconstriction in models of asthma, and reduce paralysis and inhibit monocyte and lymphocyte infiltration in experimental autoimmune encephalitis (EAE). Anti-VCAM-1 monoclonal antibodies have been shown to prolong the survival time of cardiac allografts. Recent studies have demonstrated that anti-VLA-4 mAbs can prevent insulitis and diabetes in non-obese diabetic mice, and significantly attenuate inflammation in the cotton-top tamarin model of colitis. It has further been shown that VCAM is expressed on endothelial cells of inflamed colonic tissue in a TNB/ethanol rat model of inflammatory bowel disease (*Gastroenterology* 1999, 116, 874–883).

Thus, compounds which inhibit the interaction between $\alpha_4$-containing integrins and VCAM-1 will be useful as therapeutic agents for the treatment of chronic inflammatory diseases such as rheumatoid arthritis (RA), multiple sclerosis (MS), asthma, and inflammatory bowel disease (IBD).

SUMMARY OF THE INVENTION

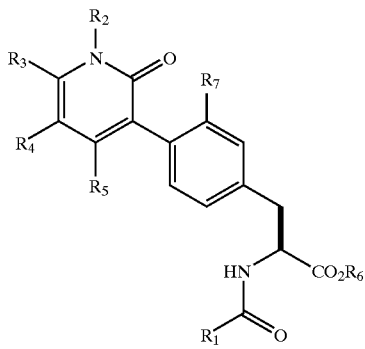

I

It has been discovered that compounds of the formula I and the pharmaceutically acceptable salts thereof wherein $R_1$, $R_2$, $R_3$, $R_5$, $R_6$ and $R_7$ are as defined below, inhibit the binding of VCAM-1 to VLA-4 and so are useful in treating inflammatory diseases in which such binding contributes to the disease process.

DETAILED DESCRIPTION OF THE INVENTION

As used in this specification, the term "halogen" means any of the four halogens, bromine, chlorine, fluorine, and iodine unless indicated otherwise. Preferred halogens are bromine, fluorine, and chlorine.

The term "lower alkyl", alone or in combination, means a straight-chain or branched-chain alkyl group containing a maximum of six carbon atoms, such as methyl, ethyl, n-propyl, isopropyl, n-butyl, sec.butyl, isobutyl, tert.butyl, n-pentyl, n-hexyl and the like. Also, as used herein "lower alkyl" may be groups which are unsubstituted or substituted by one or more groups selected independently from cycloalkyl, nitro, aryloxy, aryl, hydroxy, halogen, cyano, lower alkoxy, lower alkanoyl, lower alkylthio, lower alkyl sulfinyl, lower alkyl sulfonyl, and amino or mono- or di-lower alkyl amino. Examples of substituted lower alkyl groups include 2-hydroxylethyl, 3-oxobutyl, cyanomethyl, and 2-nitropropyl. Although this invention is specifically directed to the substituted lower alkyl group trifluoromethyl at positions $R_3$, $R_5$, $R_{22}$ and $R_{23}$, pentafluoroethyl is also contemplated at these positions.

The term "cycloalkyl" (or lower cycloalkyl) means an unsubstituted or substituted 3- to 7-membered carbacyclic ring. Substituents useful in accordance with the present invention are hydroxy, halogen, cyano, lower alkoxy, lower alkanoyl, lower alkyl, aroyl, lower alkylthio, lower alkyl sulfinyl, lower alkyl sulfonyl, aryl, heteroaryl and substituted amino.

The term "lower alkenyl" means an alkylene group having from 2 to 10 carbon atoms with a double bond located between any two adjacent carbon atoms.

The term "lower alkoxy" means a straight-chain or branched-chain alkoxy group containing a maximum of six carbon atoms, such as methoxy, ethoxy, n-propoxy, isopropoxy, n-butoxy, tert-butoxy and the like.

The term "lower alkylthio" means a lower alkyl group bonded to the rest of the molecule through a divalent sulfur atom, for example, a methyl mercapto or a isopropyl mercapto group. The term "lower alkylsulfinyl" means a lower alkyl group as defined above bound to the rest of the molecule through the sulfur atom in the sulfinyl group. The term "lower alkyl sulfonyl" means a lower alkyl group as defined above bound to the rest of the molecule through the sulfur atom in the sulfonyl group.

The term "aryl" means a mono- or bicylic aromatic group, such as phenyl or naphthyl, which is unsubstituted or substituted by conventional substituent groups. Preferred substituents are lower alkyl, lower alkoxy, hydroxy lower alkyl, hydroxy, hydroxyalkoxy, halogen, lower alkylthio, lower alkylsulfinyl, lower alkylsulfonyl, cyano, nitro, perfluoro lower alkyl, alkanoyl, aroyl, aryl alkynyl, lower alkynyl and lower alkanoylamino. Examples of aryl groups that may be used in accordance with this invention are phenyl, p-tolyl, p-methoxyphenyl, p-chlorophenyl, m-hydroxy phenyl, m-methylthiophenyl, 2-methyl-5-nitrophenyl, 2,6-dichlorophenyl, 1-naphthyl and the like.

The term "arylalkyl" means a lower alkyl group as hereinbefore defined in which one or more hydrogen atoms is/are replaced by an aryl or heteroaryl group as herein defined. Any conventional aralkyl may be used in accordance with this invention, such as benzyl and the like.

The term "heteroaryl" means an unsubstituted or substituted 5- or 6-membered monocyclic hetereoaromatic ring or a 9- or 10-membered bicyclic hetereoaromatic ring containing 1, 2, 3 or 4 hetereoatoms which are independently N, S or O. Examples of hetereoaryl rings are pyridine, benzimidazole, indole, imidazole, thiophene, isoquinoline, quinzoline and the like. Substituents as defined above for "aryl" are included in the definition of heteroaryl.

The term "lower alkoxycarbonyl" means a lower alkoxy group bonded via a carbonyl group. Examples of alkoxycarbonyl groups are ethoxycarbonyl and the like.

The term "lower alkylcarbonyloxy" means lower alkylcarbonyloxy groups bonded via an oxygen atom, for example an acetoxy group. This has the same meaning as the term "acyloxy".

The term "lower alkanoyl" means lower alkyl groups bonded via a carbonyl group and embraces in the sense of the foregoing definition groups such as acetyl, propionyl and the like. The term "perfluoro lower alkanoyl" means a perfluoro lower alkyl group (a substituted lower alkyl group where all of the hydrogens are substituted by fluoro, preferably trifluoromethyl or pentafluoroethyl) bonded to the rest of the molecule via a carbonyl group. The term perfluoro lower alkanoylamino" means a perfluoro lower alkanoyl group bonded to the rest of the molecule via an amino group.

The term "lower alkylcarbonylamino" means lower alkylcarbonyl groups bonded to the rest of the molecule via a nitrogen atom, such as acetylamino. The term lower alkylaminocarbonyl" means lower alkyl amino groups bonded to the rest of the molecule via a carbonyl group. The term "arylaminocarbonyl" means aryl groups bonded to an amino group further bonded to the rest of the molecule via a carbonyl group.

The term "aroyl" means a mono- or bicyclic aryl or heteroaryl group bonded to the rest of the molecule via a carbonyl group. Examples of aroyl groups are benzoyl, 3-cyanobenzoyl, 2-naphthoyl, nicotinoyl, and the like.

Pharmaceutically acceptable salts are well known in the art and can be made by conventional methods taking into account the chemical nature of the compound. Examples of pharmaceutically acceptable salts for acidic compounds are alkali metal or alkaline earth metals such as sodium, potassium, calcium, magnesium, basic amines or basic amino acids, ammonium or alkyl ammonium salts. Particularly desirable salts for compounds of this invention are sodium salts. The sodium salt of any acid of this invention is easily obtained from the acid by treatment with sodium hydroxide. For basic compounds, examples are salts of inorganic or organic acids such as hydrochloric, hydrobromic, sulphuric, nitric, phosphoric, citric, formic, fumaric, maleic, acetic, succinic, tartaric, methanesulfonic, and p-toluenesulfonic.

The present invention comprises a compound of formula I:

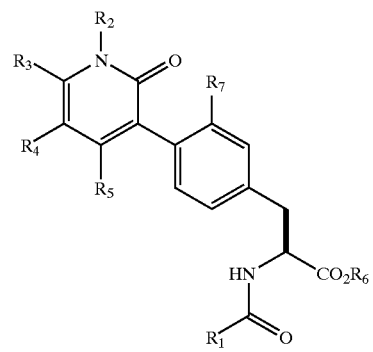

and the pharmaceutically acceptable salts thereof.

In accordance with the invention, $R_1$ is a group Y-1, Y-2 or Y-3 as described below: Y-1 is a group of the formula,

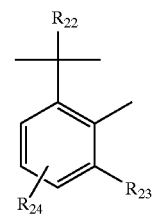

wherein: $R_{22}$ and $R_{23}$ are independently hydrogen, lower alkyl, lower alkoxy, cycloalkyl, aryl, arylalkyl, nitro, cyano, lower alkylthio, lower alkylsulfinyl, lower alkyl sulfonyl, lower alkanoyl, halogen, or perfluorolower alkyl and at least one of $R_{22}$ and $R_{23}$ is other than hydrogen, and $R_{24}$ is hydrogen, lower alkyl, lower alkoxy, aryl, nitro, cyano, lower alkyl sulfonyl, or halogen, Y-2 is a group of the formula Y-2, which is a five or six membered heteroaromatic ring bonded via a carbon atom to the amide carbonyl wherein said ring contains one, two or three heteroatoms selected from the group consisting of N, O and S and one or two atoms of said ring are independently substituted by lower alkyl, cycloalkyl, halogen, cyano, perfluoro lower alkyl, or aryl and at least one of said substituted atoms is adjacent to the carbon atom bonded to the amide carbonyl;

Y-3 is a 3–7 membered ring of the formula:

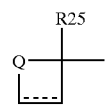

wherein: $R_{25}$ is lower alkyl, unsubstituted or fluorine substituted lower alkenyl, or a group of formula $R_{26}-(CH_2)_e-$, $R_{26}$ is aryl, heteroaryl, azido, cyano, hydroxy, lower alkoxy, lower alkoxycarbonyl, lower alkanoyl, lower alkylthio, lower alkyl sulfonyl, lower alkyl sulfinyl, perfluoro lower alkanoyl, nitro, or $R_{26}$ is a group of formula $-NR_{28}R_{29}$, wherein $R_{28}$ is hydrogen or lower alkyl, $R_{29}$ is hydrogen, lower alkyl, lower alkoxycarbonyl, lower alkanoyl, aroyl, perfluoro lower alkanoylamino, lower alkyl sulfonyl, lower alkylaminocarbonyl, arylaminocarbonyl, or $R_{28}$ and $R_{29}$, taken together with the attached nitrogen atom, form a 4, 5 or 6-membered saturated heterocyclic ring optionally containing one additional heteroatom selected from O, S, and N—$R_{40}$. Q is —$(CH_2)_fO$—, —$(CH_2)_fS$—, —$(CH_2)_fN(R_{27})$—, —$(CH_2)_f$—, $R_{27}$ is H, lower alkyl, aryl, lower alkanoyl, aroyl or lower alkoxycarbonyl, $R_{40}$ is H, lower alkyl, aryl, lower alkanoyl, aroyl or lower alkoxycarbonyl, the carbon atoms in the ring are unsubstituted or substituted by lower alkyl or halogen, e is an integer from 0 to 4, and f is an integer from 0 to 3;

$R_2$ is hydrogen, lower alkyl, substituted lower alkyl, aryl, or aryl lower alkyl, $R_3$ is hydrogen, halogen, lower alkyl, or aryl, and may also include trifluoromethyl, $R_4$ is hydrogen, halogen, lower alkyl, or aryl, $R_5$ is hydrogen, lower alkyl, lower alkoxy, trifluoromethyl, or OH, $R_6$ is hydrogen, lower alkyl, lower alkylcarbonyloxy lower alkyl, or $R_6$ is a group of formula P-3:

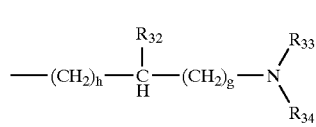

P-3 wherein: $R_{32}$ is hydrogen or lower alkyl $R_{33}$ is hydrogen, lower alkyl, aryl, $R_{34}$ is hydrogen or lower alkyl, h is an integer from 0 to 2, g is an integer from 0 to 2, the sum of h and g is 1 to 3; or $R_6$ is a group of formula P-4:

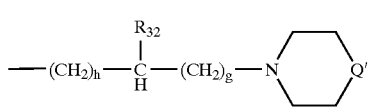

P-4 wherein: $R_{32}$, g, and h are as previously defined, Q' is O, S, —$(CH_2)_j$—, or a group of the formula N—$R_{35}$, $R_{35}$ is hydrogen, lower alkyl, lower alkanoyl, lower alkoxycarbonyl, j is 0, 1 or 2, $R_7$ is hydrogen, chloro, lower alkoxy, or lower alkyl. Preferably Q is —$(CH_2)_fO$—, —$(CH_2)_fS$—, or —$(CH_2)_f$ (Formula 1a). It is also preferred in compounds of formula I or Formula 1a that $R_5$ is hydrogen, lower alkyl, or trifluoromethyl (Formula 1b).

The compounds of the invention can exist as stereoisomers and diastereomers, all of which are encompassed within the scope of the present invention.

In one preferred embodiment of the compound of formula I, Formula 1a, or Formula 1b, $R_2$ is hydrogen, lower alkyl, or aryl lower alkyl, $R_3$ is hydrogen, lower alkyl, or trifluoromethyl, preferably hydrogen, $R_4$ is hydrogen or halogen, preferably halogen, $R_5$ is hydrogen, lower alkyl, trifluoromethyl and may in addition be lower alkoxy, but is preferably hydrogen, $R_6$ is hydrogen or lower alkyl, and $R_7$ is hydrogen, chloro, lower alkoxy, or lower alkyl.

A preferred embodiment of the present invention is a compound of the formula I, 1a, or 1b:

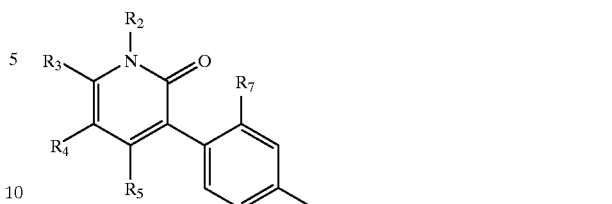

I wherein $R_1$ is a group Y-1

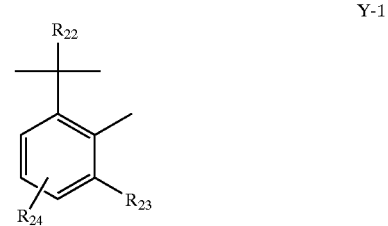

Y-1 wherein $R_{22}$ and $R_{23}$ are independently hydrogen, lower alkyl, lower alkoxy, cycloalkyl, aryl, arylalkyl, nitro, cyano, lower alkylthio, lower alkylsulfinyl, lower alkyl sulfonyl, lower alkanoyl, halogen, or perfluorolower alkyl and at least one of $R_{22}$ and $R_{23}$ is other than hydrogen, and $R_{24}$ is hydrogen, lower alkyl, lower alkoxy, aryl, nitro, cyano, lower alkyl sulfonyl, or halogen. In such compounds, it is preferred that $R_2$ is hydrogen, lower alkyl or aryl lower alkyl; $R_3$ is hydrogen; $R_4$ is hydrogen, or halogen, or may in addition be lower alkyl (but preferably is halogen); $R_5$ is hydrogen, lower alkyl, or trifluoromethyl, or may in addition be lower alkoxy (but preferably is hydrogen); $R_6$ is hydrogen or lower alkyl; and $R_7$ is hydrogen, chloro, lower alkoxy, or lower alkyl.

A more preferred embodiment of the present invention is a compound of the formula I, Formula 1a, or Formula 1b above wherein $R_1$ is a group Y-1

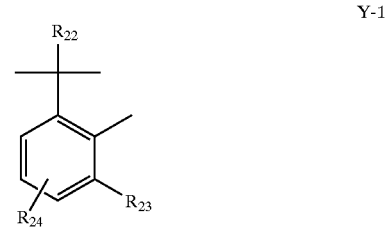

Y-1 wherein $R_{22}$ and $R_{23}$ are independently hydrogen, lower alkyl or halogen, especially lower alkyl or halogen; $R_{24}$ is hydrogen, lower alkyl or lower alkoxy, especially hydrogen. In such compounds, it is preferred that $R_2$ is hydrogen, lower alkyl or aryl lower alkyl; $R_3$ is hydrogen; $R_4$ is hydrogen or halogen, $R_5$ is hydrogen, or lower alkyl, $R_6$ is hydrogen or lower alkyl; and $R_7$ is hydrogen, chloro, lower alkoxy, or lower alkyl. In particularly preferred compounds $R_{22}$ and $R_{23}$ are independently hydrogen, lower alkyl or halogen, $R_{24}$ is hydrogen or lower alkoxy, and $R_2$ is or aryl lower alkyl. Alternatively, in such compounds, it is preferred that $R_2$ is hydrogen, lower alkyl or aryl lower alkyl; $R_3$ is hydrogen; $R_4$ is hydrogen, or may in addition be lower alkyl (but preferably is halogen); $R_5$ is hydrogen, lower alkyl, or trifluoromethyl, or may in addition be lower alkoxy (but preferably is hydrogen); $R_6$ is hydrogen or lower alkyl; and $R_7$ is hydrogen, chloro, lower alkoxy, or lower alkyl.

Another preferred embodiment of the present invention is a compound of the formula I, Formula 1a, or Formula 1b above wherein $R_1$ is a five or six membered heteroaromatic ring bonded via a carbon atom to the amide carbonyl wherein said ring contains one, two or three heteroatoms selected from the group consisting of N, O and S and one or two atoms of said ring are independently substituted by lower alkyl, cycloalkyl, halogen, cyano, perfluoro lower alkyl, or aryl and at least one of said substituted atoms is adjacent to the carbon atom bonded to the amide carbonyl. In such compounds, it is particularly preferred that $R_2$ is hydrogen, lower alkyl or aryl lower alkyl; $R_3$ is hydrogen; $R_4$ is hydrogen or halogen (preferably halogen); $R_5$ is hydrogen, trifluoromethyl or lower alkyl (preferably hydrogen); $R_6$ is hydrogen or lower alkyl; and $R_7$ is hydrogen, chloro, lower alkoxy, or lower alkyl. Alternatively, in such compounds, it is preferred that $R_2$ is hydrogen, lower alkyl or aryl lower alkyl; $R_3$ is hydrogen; $R_4$ is hydrogen, or halogen, or may in addition be lower alkyl (but preferably is halogen); $R_5$ is hydrogen, lower alkyl, or trifluoromethyl, or may in addition be lower alkoxy (but preferably is hydrogen); $R_6$ is hydrogen or lower alkyl; and $R_7$ is hydrogen, chloro, lower alkoxy, or lower alkyl.

Another preferred embodiment of the present invention is a compound of the formula I, Formula 1a, or Formula 1b above wherein $R_1$ is a group of the formula Y-3 which is a 3–7 membered ring of the formula:

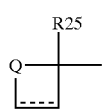

Y-3 wherein $R_{25}$ is lower alkyl, unsubstituted or fluorine substituted lower alkenyl, or a group of formula $R_{26}$—$(CH_2)_e$—, $R_{26}$ is aryl, heteroaryl, azido, cyano, hydroxy, lower alkoxy, lower alkoxycarbonyl, lower alkanoyl, lower alkylthio, lower alkyl sulfonyl, lower alkyl sulfinyl, perfluoro lower alkanoyl, nitro, or $R_{26}$ is a group of formula —$NR_{28}R_{29}$, wherein $R_{28}$ is hydrogen or lower alkyl, $R_{29}$ is hydrogen, lower alkyl, lower alkoxycarbonyl, lower alkanoyl, aroyl, perfluoro lower alkanoylamino, lower alkyl sulfonyl, lower alkylaminocarbonyl, arylaminocarbonyl; or $R_{28}$ and $R_{29}$, taken together with the attached nitrogen atom, form a 4, 5 or 6-membered saturated heterocyclic ring optionally containing one additional heteroatom selected from O, S, and N—$R_{40}$. Q is —$(CH_2)_f$O—, —$(CH_2)_f$S—, —$(CH_2)_f$N($R_{27}$)—, —$(CH_2)_f$—, $R_{27}$ is H, lower alkyl, aryl, lower alkanoyl, aroyl or lower alkoxycarbonyl, $R_{40}$ is H, lower alkyl, aryl, lower alkanoyl, aroyl or lower alkoxycarbonyl, the carbon atoms in the ring are unsubstituted or substituted by lower alkyl or halogen, e is an integer from 0 to 4, and f is an integer from 0 to 3. In such compounds, it is particularly preferred that $R_2$ is hydrogen, lower alkyl or aryl lower alkyl; $R_3$ is hydrogen; $R_4$ is hydrogen or halogen (preferably halogen); $R_5$ is hydrogen, trifluoromethyl, or lower alkyl (preferably hydrogen); $R_6$ is hydrogen or lower alkyl; and $R_7$ is hydrogen, chloro, lower alkoxy, or lower alkyl. Alternatively, in such compounds, it is preferred that $R_2$ is hydrogen, lower alkyl or aryl lower alkyl; $R_3$ is hydrogen; $R_4$ is hydrogen, or halogen, or may in addition be lower alkyl (but preferably is halogen); $R_5$ is hydrogen, lower alkyl, or trifluoromethyl), or may in addition be lower alkoxy (but preferably is hydrogen); $R_6$ is hydrogen or lower alkyl; and $R_7$ is hydrogen, chloro, lower alkoxy, or lower alkyl.

A more preferred embodiment of the present invention is a compound of formula I, Formula 1a, or Formula 1b above wherein $R_1$ is a group of the formula Y-3 which is a 3–7 membered ring of the formula:

Y-3 wherein $R_{25}$ a group of formula $R_{26}$—$(CH_2)_e$—, wherein $R_{26}$ is lower alkoxy, Q is —$(CH_2)_f$—, e is an integer from 0 to 4 and f is an integer from 0 to 3; Such compounds are especially preferred where R2 is hydrogen, lower alkyl, substituted lower alkyl, aryl, or aryl lower alkyl, especially aryl lower alkyl. Such compounds are also preferred when $R_2$ is lower alkyl or aryl lower alkyl; $R_3$ is hydrogen; $R_4$ is hydrogen or halogen; $R_5$ is hydrogen; $R_6$ is hydrogen or lower alkyl; and $R_7$ is hydrogen, chloro, lower alkoxy, or lower alkyl. Alternatively, in such compounds, it is preferred that $R_2$ is hydrogen, lower alkyl or aryl lower alkyl; $R_3$ is hydrogen; $R_4$ is hydrogen, or halogen, or may in addition be lower alkyl (but preferably is halogen); $R_5$ is hydrogen, lower alkyl, or trifluoromethyl), or may in addition be lower alkoxy (but preferably is hydrogen); $R_6$ is hydrogen or lower alkyl; and $R_7$ is hydrogen, chloro, lower alkoxy, or lower alkyl.

In any compound of this invention of formula I, Formula 1a, or Formula 1b, $R_1$ may be a group of formula Y-1 or a group of formula Y-3; $R_2$ may be lower alkyl, aryl lower alkyl, or hydrogen (preferably lower alkyl or aryl lower alkyl), $R_3$ may be hydrogen, lower alkyl, or trifluoromethyl; $R_4$ may be hydrogen or halogen; $R_5$ may be hydrogen, lower alkyl, or trifluoromethyl; $R_6$ may be hydrogen, lower alkyl, lower alkylcarbonyloxy lower alkyl, a group of formula P-3 or a group of formula P-4 (preferably the four former groups); and $R_7$ may be lower alkyl or hydrogen, preferably hydrogen.

In any compound of this invention of formula I, Formula 1a, Formula 1b, or the preferred compounds described in the paragraph immediately above, the groups within Y-1 and Y-3 may be specifically selected as follows: $R_{22}$ and $R_{23}$ are hydrogen, halogen, lower alkyl, $R_{24}$ is hydrogen or lower alkoxy, $R_{25}$ is a group of formula $R_{26}$—$(CH_2)_e$—, wherein $R_{26}$ is lower alkoxy, Q is —$(CH_2)_f$—, e is an integer from 0 to 4 and f is an integer from 0 to 3, and/or where $R_2$ is lower alkyl, $R_4$ is hydrogen, $R_3$ and $R_5$ are lower alkyl or trifluoromethyl, and $R_6$ is hydrogen, lower alkyl, or lower alkylcarbonyloxy lower alkyl, or a group of formula P-3 preferably where $R_{32}$ is hydrogen; $R_{33}$ and $R_{34}$ are lower alkyl; one of g and h is 1 and the other is 0. In such compounds, preferably $R_6$ and $R_7$ are hydrogen, and/or $R_2$ is lower alkyl; $R_3$ is hydrogen; $R_4$ is hydrogen or halogen; and $R_5$ is hydrogen or lower alkyl, and preferably $R_{22}$ and $R_{23}$ are lower alkyl or halogen, especially halogen, and $R_{24}$ is hydrogen, or $R_{22}$ and $R_{23}$ are hydrogen or halogen, and $R_{24}$ is hydrogen or lower alkoxy, preferably hydrogen or $R_1$ is Y-3. In other such compounds, $R_{22}$ and $R_{23}$ are preferably halogen, or lower alkyl, $R_{24}$ is hydrogen, or lower alkoxy, $R_{25}$ is a group of formula $R_{26}$—$(CH_2)_e$—, wherein $R_{26}$ is lower alkoxy, Q is —$(CH_2)_f$—, e is an integer from 0 to 4 and f is an integer from 0 to 3, and/or $R_2$ is aryl lower alkyl; $R_3$ is hydrogen, $R_4$ is halogen, and $R_5$, $R_6$ and $R_7$ are hydrogen. It is also preferred that $R_1$ be Y-1.

In a particularly preferred compound of formula I, Formula 1a, or Formula 1b, $R_1$ is a group of formula Y-1 or a group of formula Y-3; $R_2$ is lower alkyl or aryl lower alkyl; $R_3$ is hydrogen, lower alkyl, or trifluoromethyl; $R_4$ is hydrogen or halogen; $R_5$ is hydrogen, lower alkyl, or trifluoromethyl; $R_6$ is hydrogen, lower alkyl, lower alkylcarbonyloxy lower alkyl, or a group of formula P-3; and $R_7$ is hydrogen (Formula A)

In a preferred compound of Formula A, the groups within Y-1 and Y-3 may be specifically selected as follows: $R_{22}$ and $R_{23}$ are hydrogen, halogen, or lower alkyl, $R_{24}$ is hydrogen, or lower alkoxy, $R_{25}$ is a group of formula $R_{26}$—$(CH_2)_e$—, wherein $R_{26}$ is lower alkoxy, Q is —$(CH_2)_f$—, e is an integer from 0 to 4 and f is an integer from 0 to 3 (Formula A-1).

In a preferred compound of Formula A-1, $R_2$ is lower alkyl, $R_4$ is hydrogen, and $R_3$ and $R_5$ are lower alkyl or trifluoromethyl (Formula A-1a). In one embodiment of Formula A-1a, $R_6$ is hydrogen. In this embodiment, $R_1$ may be Y-1, especially where $R_{22}$ and $R_{23}$ are halogen or lower alkyl, or $R_1$ may be Y-3. In other embodiments of Formula A-1 a, $R_6$ is lower alkyl, or is lower alkylcarbonyloxy lower alkyl, or is a group of formula P-3 wherein $R_{32}$ is hydrogen; $R_{33}$ and $R_{34}$ are lower alkyl; one of g and h is 1 and the other is 0.

In another preferred compound of Formula A-1, $R_6$ is hydrogen. It is preferred that $R_2$ is lower alkyl; $R_3$ is hydrogen; $R_4$ is hydrogen or halogen; and $R_5$ is hydrogen or lower alkyl (Formula A-1b). In one embodiment of Formula A-1b, $R_1$ is Y-1. Preferably $R_{22}$ and $R_{23}$ are lower alkyl or halogen, and $R_{24}$ is hydrogen, or $R_{22}$ and $R_{23}$ are halogen, and $R_{24}$ is hydrogen, or $R_{22}$ and $R_{24}$ are hydrogen or halogen, and $R_{23}$ is lower alkoxy. In another embodiment of Formula A-1b, $R_1$ is Y-3.

In another preferred compound of Formula A, $R_{22}$ and $R_{23}$ are hydrogen, halogen, or lower alkyl, $R_{24}$ is hydrogen or lower alkoxy, $R_{25}$ is a group of formula $R_{26}$—$(CH_2)_e$—, wherein $R_{26}$ is lower alkoxy, Q is —$(CH_2)_f$—, e is an integer from 0 to 4 and f is an integer from 0 to 3. Preferably $R_2$ is aryl lower alkyl; $R_3$ is hydrogen, $R_4$ is halogen, and $R_5$, $R_6$ and $R_7$ are hydrogen. It is also preferred that $R_1$ be Y-1 or Y-3.

The compounds of the invention inhibit the binding of VCAM-1 and fibronectin to VLA-4 on circulating lymphocytes, eosinophils, basophils, and monocytes ("VLA-4-expressing cells"). The binding of VCAM-1 and fibronectin to VLA-4 on such cells is known to be implicated in certain disease states, such as rheumatoid arthritis, multiple sclerosis, inflammatory bowel disease, and particularly in the binding of eosinophils to airway endothelium which contributes to the cause of the lung inflammation which occurs in asthma. Thus, the compounds of the present invention would be useful for the treatment of asthma.

On the basis of their capability of inhibiting binding of VCAM-1 and fibronectin to VLA-4 on circulating lymphocytes, eosinophils, basophils, and monocytes, the compounds of the invention can be used as medicament for the treatment of disorders which are known to be associated with such binding. Examples of such disorders are rheumatoid arthritis, multiple sclerosis, asthma, and inflammatory bowel disease. The compounds of the invention are preferably used in the treatment of diseases which involve pulmonary inflammation, such as asthma. The pulmonary inflammation which occurs in asthma is related to the activation and lung infiltration of eosinophils, monocytes and lymphocytes which have been activated by some asthma-triggering event or substance.

Furthermore, compounds of the invention also inhibit the binding of MadCAM to the cellular receptor alpha4-beta7, also known as LPAM, which is expressed on lymphocytes, eosinophiles and T-cells. While the precise role of alpha4-beta7 interaction with various ligands in inflammatory conditions such as asthma is not completely understood, compounds of the invention which inhibit both alpha4-beta1 and alpha4-beta7 receptor binding are particularly effective in animal models of asthma. Furthermore work with monoclonal antibodies to alpha4-beta7 indicate that compounds which inhibit alpha4-beta7 binding to MadCAM are useful for the treatment of inflammatory bowel disease. They would also be useful in the treatment of other diseases in which such binding is implicated as a cause of disease damage or symptoms.

The compounds of the invention can be administered orally, rectally, or parentally, e.g., intravenously, intramuscularly, subcutaneously, intrathecally or transdermally; or sublingually, or as opthalmalogical preparations, or as an aerosol in the case of pulmonary inflammation. Capsules, tablets, suspensions or solutions for oral administration, suppositories, injection solutions, eye drops, salves or spray solutions are examples of administration forms.

Intravenous, intramuscular, oral or inhalation administration is a preferred form of use. The dosages in which the compounds of the invention are administered in effective amounts depending on the nature of the specific active ingredient, the age and the requirements of the patient and the mode of administration. Dosages may be determined by any conventional means, e.g., by dose-limiting clinical trials. Thus, the invention further comprises a method of treating a host suffering from a disease in which VCAM-1 or fibronectin binding to VLA-4-expressing cells is a causative factor in the disease symptoms or damage by administering an amount of a compound of the invention sufficient to inhibit VCAM-1 or fibronectin binding to VLA-4-expressing cells so that said symptoms or said damage is reduced. In general, dosages of about 0.1–100 mg/kg body weight per day are preferred, with dosages of 1–25 mg/kg per day being particularly preferred, and dosages of 1–10 mg/kg body weight per day being espeically preferred.

The invention further comprises pharmaceutical compositions which contain a pharmaceutically effective amount of a compound of the invention and a pharmaceutically acceptable carrier. Such compositions may be formulated by any conventional means. Tablets or granulates can contain a series of binders, fillers, carriers or diluents. Liquid compositions can be, for example, in the form of a sterile water-miscible solution. Capsules can contain a filler or thickener in addition to the active ingredient. Furthermore, flavour-improving additives as well as substances usually used as preserving, stabilizing, moisture-retaining and emulsifying agents as well as salts for varying the osmotic pressure, buffers and other additives can also be present.

The previously mentioned carrier materials and diluents can comprise any conventional pharmaceutically acceptable organic or inorganic substances, e.g., water, gelatine, lactose, starch, magnesium stearate, talc, gum arabic, polyalkylene glycols and the like.

Oral unit dosage forms, such as tablets and capsules, preferably contain from 25 mg to 1000 mg of a compound of the invention.

Generally the compounds of the present invention can be prepared from suitable phenylalanine derivatives via a palladium catalyzed reaction with a 3-halo-2-pyridone.

As shown in Reaction Scheme 1, a 4-iodo- or 4-bromophenylalanine derivative such as 1, is converted into a protected phenylalanine derivative 2 in which $R_7$' is hydrogen, chloro, lower alkyl or lower alkoxy, $P_1$ is a standard nitrogen protecting group such as a Boc, or carbobenzyloxy group and $P_2$ is lower alkyl or substituted lower alkyl selected appropriately to serve as a protecting group or an element of a prodrug. The group $P_2$ can be introduced by conventional means familiar to those who practice peptide chemistry. The order of the addition of $P_1$ and $P_2$ is not critical and will depend on the particular choice of reagents. A discussion of the use and introduction of protecting groups is provided in Theodora W. Greene and Peter G. M. Wuts., *Protecting Groups in Organic Synthesis*, Wiley Interscience, New York, 1991. Alternatively, a compound of formula 1 may be converted to a compound of formula 4, in which $R_1'$ represents a component of an acyl group of the invention. A convenient method is to introduce the ester group $P_2$ first, followed by a coupling reaction of the free amine using conventional peptide coupling reagents, for example HBTU in the presence of a tertiary amine base such as diethylisopropylamine. Again, the particular choice of reagents may dictate altering the sequence of the introduction of $R_1'$ and $P_2$. Conversion of compounds of formula 2 or 4 to derivatives 3 or 5, in which M represents a substituted tin or boron atom, can be effected by treatment with a suitable species, for example hexamethylditin, hexabutylditin or a tetraalkoxydiboron in the presence of a source of palladium zero. The methodology is outlined and referenced in F. Diederich and P. J. Stang, ed, *Metal Catalyzed Cross Coupling Reactions*, Wiley-VCH, Weinheim, Germany, 1998.

Reaction Scheme 1.

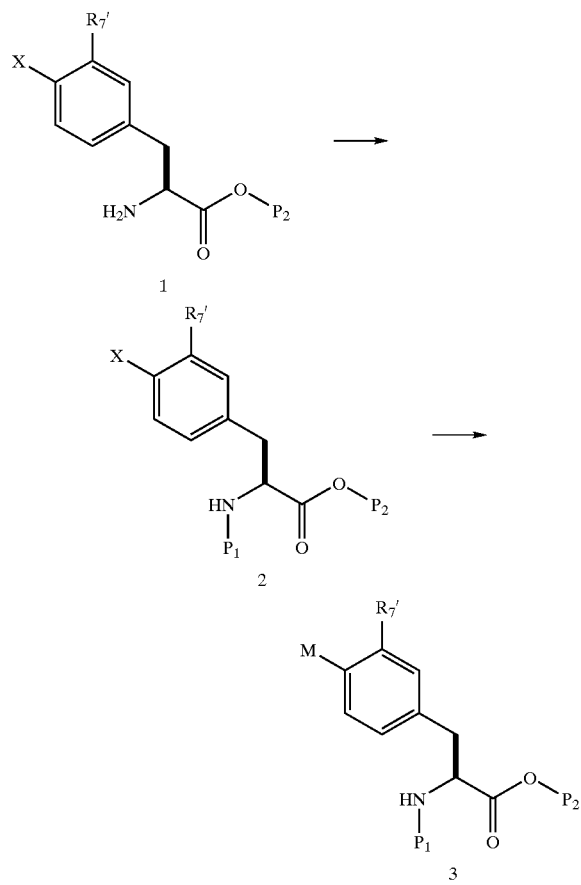

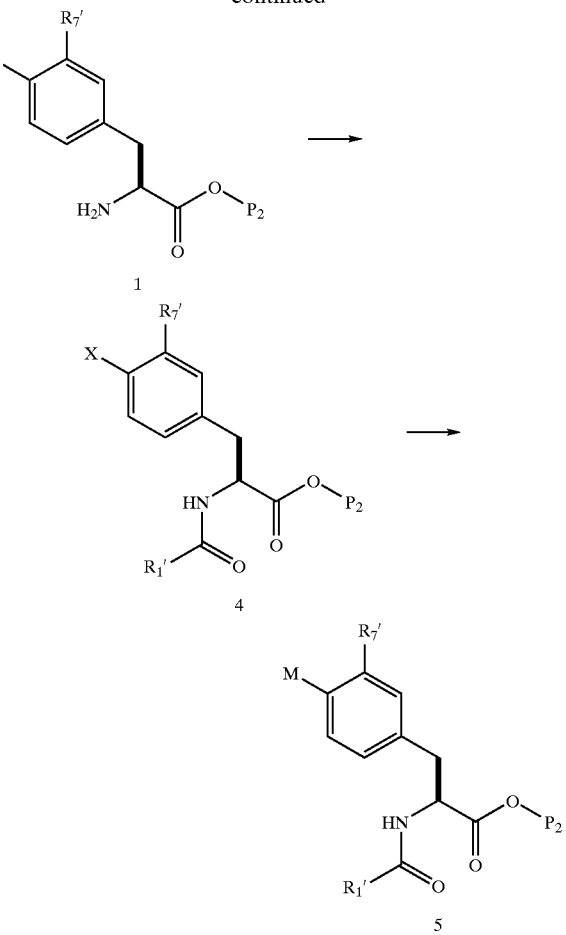

Substituted pyridones of formula 6 wherein $R_{3'}$, $R_{4'}$, and $R_{5'}$ are hydrogen, lower alkyl, perfluorolower alkyl, halogen, aryl, hydroxy, or lower alkoxy are commercially available or prepared following general literature methods (for example, discussion of some of these known methods are found in: P. Wirth, et al., Ger. Offen. 28 17 293, Aug. 12, 1979, Masaru Hojo, et al. Chem. Lett. 1976, 499–502, Robert W. Lang, et al. Helvetica Chimica Acta, 1988, 71, 596–601). Compounds of formula 7 wherein $R_{2'}$ is lower alkyl or aryl lower alkyl, may be obtained by alkylation of compounds of formula 6 by treatment with an alkylating agent such as iodomethane, benzylbromide in the presence of a base such as potassium carbonate and optionally, a phase transfer catalyst. For less reactive alkylating agents, it may be necessary to use a stronger base such as an alkali metal hydroxide and to heat the reaction mixture. Compounds of formula 7 as defined above may be halogenated in the 3-position by treatment with conventional halogenating reagents such as bromine, N-iodosuccinimide or N-bromosuccinimide in a suitable solvent such as glacial acetic acid or aqueous acetic acid to give halopyridones of formula 8, X=Br or I, $R_{2'}$ is independently hydrogen, lower alkyl, substituted lower alkyl, or aryl lower alkyl, $R_{3'}$ and $R_{5'}$ are hydrogen, lower alkyl or perfluorolower alkyl. Treatment with excess halogenating agent leads to compounds of structure 8 with $R_{4'}$=halogen. For compounds of formula 8 with $R_{2'}$=aryl, it is convenient to start with N-aryl pyridones which are known compounds or can be prepared by known methods, or to introduce an aryl moiety for example by using an Ullmann coupling reaction as described by Masakatsu, et al., Chem. Pharm. Bull. 1997, 45, 719.

Reaction Scheme 2.

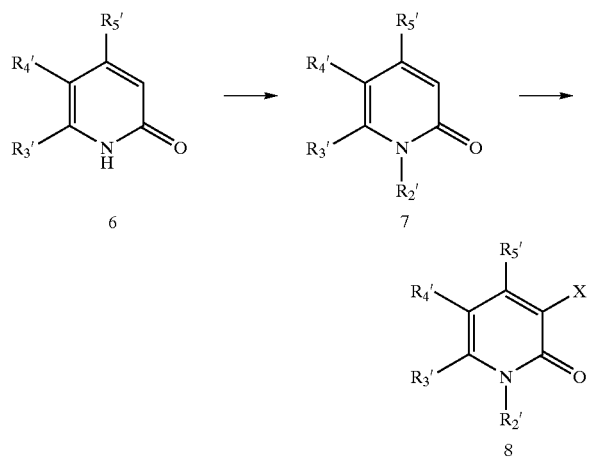

As shown in Reaction Scheme 3, a compound of formula 8 can be used in a palladium catalyzed coupling reaction with a phenylalanine derivative of formula 3 or 5. For example, when M is a substituted tin, treatment of a mixture of 8 and the phenylalanine of formula 3 or 5 with a source of palladium zero such as tetraakis(triphenylphosphine) palladium or bis(triphenylphosphine)palladium dichloride in the presence of an inert solvent such as DMF at a temperature of between room temperature and 100° C. gives a compound of formula 9 or 10. Compounds of structure 9 may be converted into compounds of structure 10 by removal of the protecting group $P_1$, which may be accomplished by conventional means depending on the selection of $P_1$. For example, if $P_1$ is a Boc group, it may be removed by treatment with a strong acid, such as trifluoroacetic acid, optionally in the presence of a solvent such as methylene chloride and a scavenging agent. The resulting free amine may then be acylated with an acid of the formula $R_1'CO_2H$ using convention peptide coupling techniques. For example, by treatment with HBTU in the presence of a tertiary amine base such as diethylisopropylamine in the presence of an aprotic solvent such as DMF to give the compound of structure 10.

If the free acid 11 is the desired end product, the ester group, $P_2$ may be removed by conventional means. For example, in the case that $P_2$ is lower alkyl, for example methyl, it may be removed by treatment with an alkali metal hydroxide, for example lithium hydroxide, in a suitable solvent, for example aqueous THF optionally containing methanol to assist with solubility. If $P_2$ were a benzyl or substituted benzyl group, it could also be removed by catalytic hydrogenation over a noble metal catalyst, for example palladium on carbon.

Reaction Scheme 3.

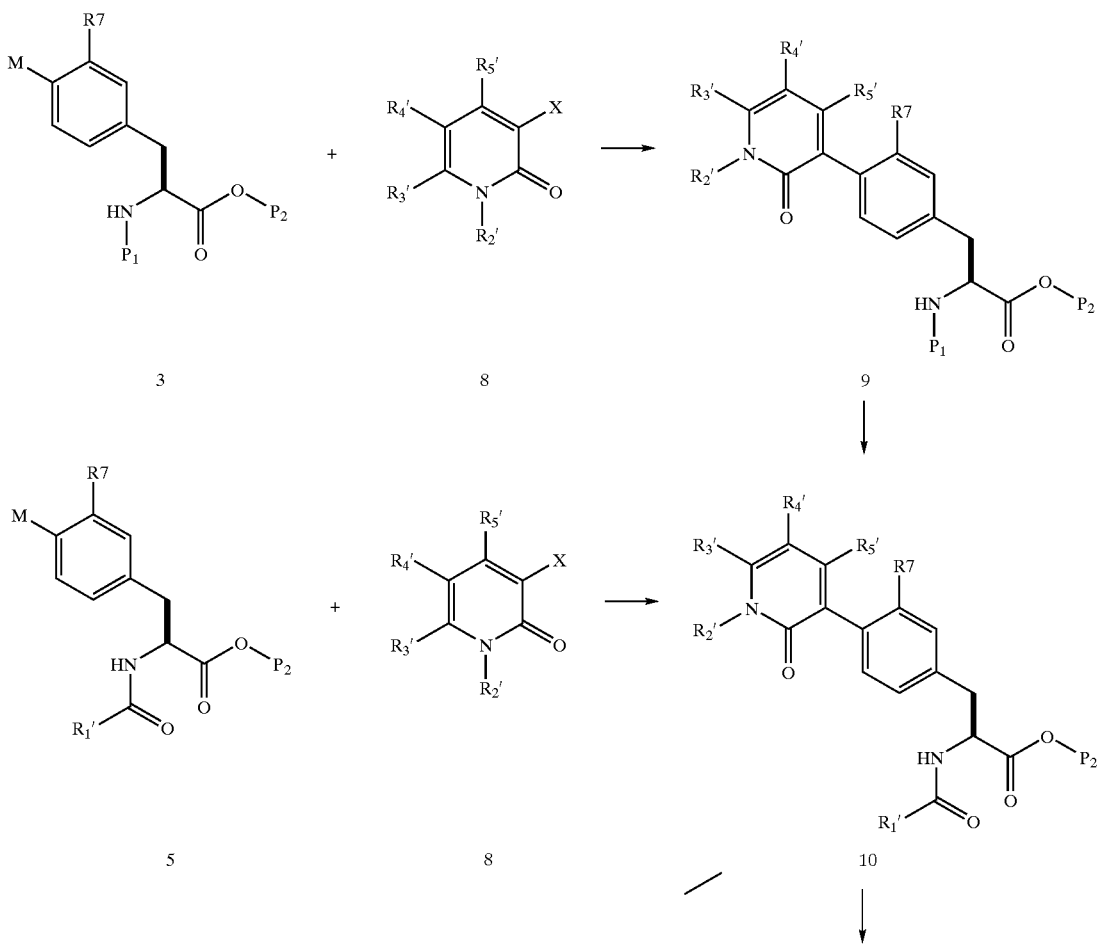

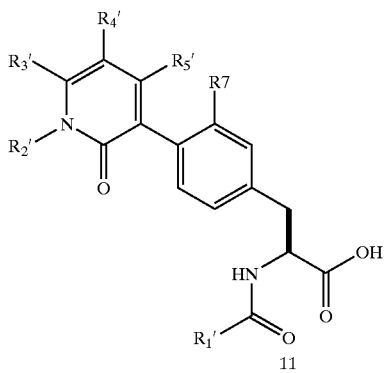

Alternatively, as shown in Reaction Scheme 4, a compound of structure 8, wherein X is bromide or iodide, may be converted to a species of formula 12, in which M' represents a substituted tin, boron or zinc atom. In the case of the tin or boron derivatives, in which M' represents a substituted tin or boron atom, the conversion can be effected by treatment with a suitable species, for Reaction Scheme 4.

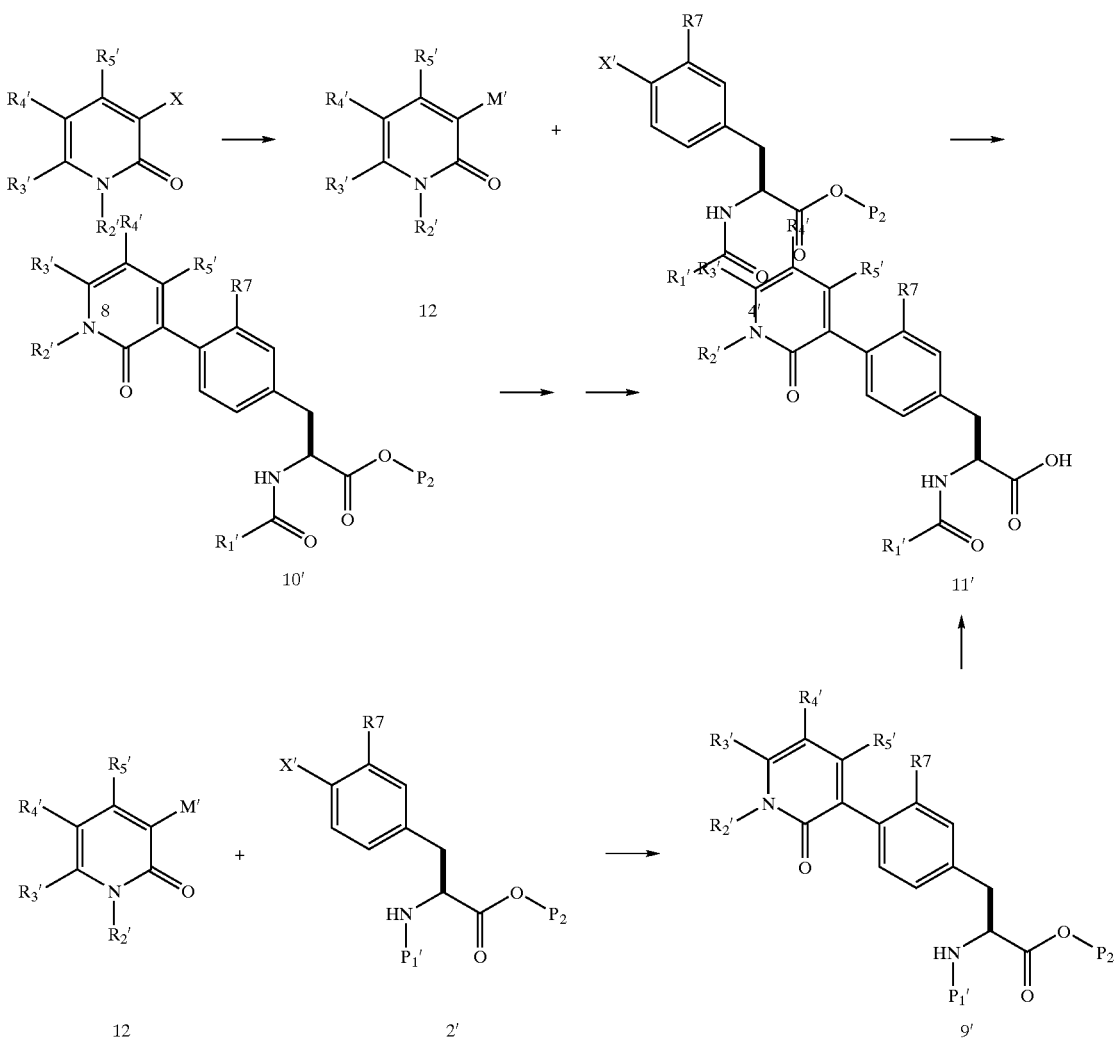

example hexamethylditin, hexabutylditin or a tetraalkoxy-diboron in the presence of a source of palladium zero. For the formation of the zinc derivative, 12, M'=Zn(halogen), conversion may be effected by treatment of the compound of formula 8, X=I with a source of activated zinc metal in a suitable inert solvent, for example dimethylacetamide at a temperature of from room temperature to 100° C. until conversion is complete to give a compound of formula 12, M'=Zn(halogen). These compounds of formula 12 can be reacted with a 4-substituted phenylalanine derivative of formula 4' in which X' is iodo, bromo, or trifluoromethylsulfonyloxy in the presence of a source of palladium zero to give a compound of formula 10'. In the case where the ester group represented by $P_2$ is not part of the targeted compound, it can be removed using ester hydrolysis procedures appropriate to the particular $P_2$. For example, where $P_2$ is lower alkyl, for example methyl, it can be removed by standard base hydrolysis using an alkali metal hydroxide, for example, lithium hydroxide. In a variation on this procedure, it may be desirable to carry a protecting group through the coupling reaction and substitute it at a later time. In this case, a compound of formula 2', in which $P_1'$ is lower alkoxycarbonyl or benzyloxycarbonyl and X' is as defined above, may be coupled with a pyridone of structure 12 to give a compound of structure 9' which in turn may be converted to a compound of the invention using the general procedures noted above in reaction scheme 3.

An alternative route to compounds of this invention, as shown in Reaction Scheme 5, which is particularly applicable to compounds in which $R_7'$ is other than hydrogen, is to build an aldedyde of formula 14. This can be accomplished by reacting a compound of formula 12 with a compound of formula 13, in which $R_7'$ represents lower alkyl or lower alkoxy, and X" represents an iodide, bromide, of trifluoromethylsulfonyloxy moiety and $R_8$ represents a protected alcohol or an aldehyde. For alcohols, suitable protecting groups include silyl ethers, benzyl ethers. If necessary, aldehydes, may be protected as their acetal derivatives. The compound of formula 12 can be converted to an aldehyde of formula 15 by convertional steps which, when $R_8$ is an alcohol, would involve protecting group removal, if necessary, followed by oxidation. Any of the common reagents for the selective oxidation of primary benzyl alcohols to aldehydes may be employed, for example, treatment with activated manganese dioxide in an inert solvent. In the case where $R_8$ represents a protected aldehyde, conversion to an aldehyde of formula 15 can be carried out by a suitable protecting group removal, for example hydrolysis of an acetal with dilute acid. Reaction of 15 to give a dehydroamino acid of formula 16 can be effected by treatment with a Wittig reagent of formula 17 in which $P_1'$ is lower alkoxycarbonyl or benzyloxycarbonyl and $P_2$ is as defined above. For example treatment of 15 with (±)-N-(benzyloxycarbonyl)-α-phosphonoglycine trimethyl ester in the presence of a suitable base for example tetramethylguanidine leads directly to a dehydroamino acid of formula 16, $P_2$=methyl and $P_1'$=benzyloxycarbonyl. Enantioselective reduction of 16 to the L-amino acid 18 can be effected by use of a number of reducing agents suitable for the purpose, for example, the recently described ethyl-DuPHOS rhodium reagent (Burk, M. J., Feaster, J. E.; Nugent, W. A.; Harlow, R. L. *J. Am. Chem. Soc.* 1993, 115, 10125) using essentially the literature procedure. Further conversion of 18 to the compounds of the invention can be carried out using the general procedures discussed above. Alternatively, the general methods outlined in reaction scheme 5 can be used to prepare compounds of structure 4 or 4' in which $R_7'$ is other than hydrogen. These compounds of structure 4 or 4' can then be employed to prepare compounds of the invention as outlined in reaction schemes 1 to 4.

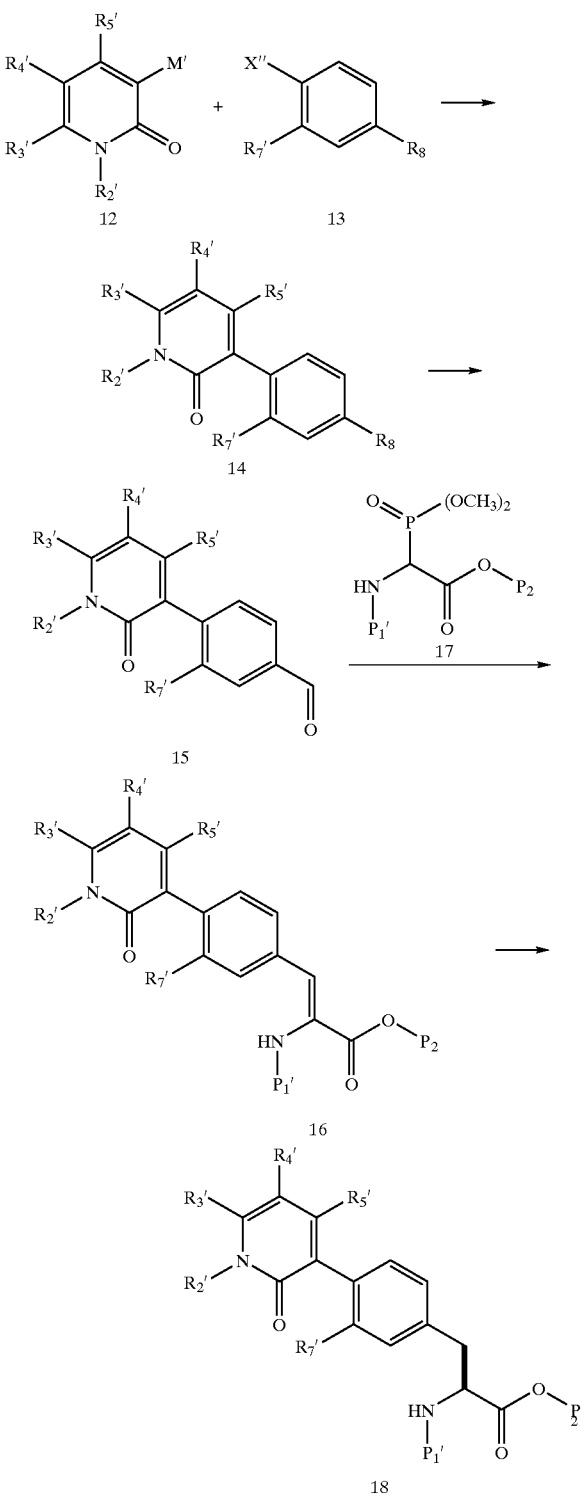

Reaction Scheme 5.

In one embodiment, the N-acyl group, $R_1'$ of structure 11, is derived from a 2-subsituted benzoic acid. Appropriate 2-substituted benzoic acids are either commercially available or can be prepared by conventional means. For example ortho-substituted aryl iodides or triflates may be carbonylated in the presence of carbon monoxide and a suitable palladium catalyst. The preparation of such iodide or triflate intermediates is dependent on the particular substitution pattern desired and they may be obtained by direct iodination or diazotization of an aniline followed by treatment with a source of iodide for example, potassium iodide. Triflates may be derived from the corresponding phenols by conventional means such as by treatment with trifluoromethane sulfonic anhydride in the presence of a base such as triethylamine or diisopropylethylamine in an inert solvent. As shown in Reaction Scheme 6, one other means of obtaining ortho-substituted benzoic acids involves treatment of an 2-methoxyphenyloxazoline derivative such as compound 19, $Z_1$ and $Z_2$=hydrogen, alkyl, chloro, perfluoro lower alkyl, lower alkoxy with an alkyl Grignard reagent followed by hydrolysis of the oxazoline ring following the general procedure described by Meyers, A. I., Gabel, R., Mihelick, E. D, *J. Org. Chem.* 1978, 43, 1372–1379, to give an acid of formula 20. 2- or 2,6-Disubstituted benzonitriles also serve as convenient precursors to the corresponding benzoic acids. In the case of highly hindered nitriles, for example 2-chloro-6-methylbenzonitrile, conventional hydrolysis under acidic or basic conditions is difficult and better results are obtained by DIBAL reduction to the corresponding benzaldehyde followed by oxidation using a chromium based oxidizing reagent. Other methods are exemplified in Chen, et al., WO 9910312.

Reaction Scheme 6

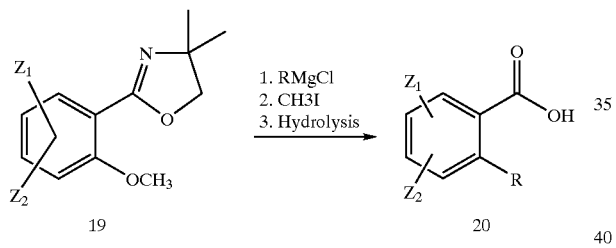

Referring now to Reaction Scheme 7, cyclic acids of formula 23 are known compounds or can be prepared using standard methodologies. For the preparation of substituted alkyl- or cycloalkylcarboxylic acids, alkylation reactions can be employed using an alkali metal dianion of the acid or monoanion of the corresponding ester. For example, a cycloalkyl carboxylic acid ester of formula 21 can be treated with a strong base, for example, lithium diisopropylamide in an inert solvent, for example THF followed by addition of group $R_{41}$-Lv wherein $R_{41}$ represents a desired side chain, such as a substituted benzyl, lower alkyl, lower alkoxy alkyl, azido lower alkyl and the like and Lv represents a leaving group such as a bromide, iodide, mesylate or similar group known to participate in ester enolate alkylation reactions. The product ester 22 may be hydrolyzed to the acid 23 using alkali metal hydroxide in a suitable solvent, for example aqueous alcohol. Depending on the nature of $R_{41}$ and the eventual target, the compound 23 may be coupled to an amine such as compound 1 and converted to the target directly or $R_{41}$ may be subject to further manipulation at a suitable point in the synthesis. For example, if $R_{41}$ is an azido lower alkyl moiety, the azide may be reduced using for example a trialkyl phosphine reagent followed by functionalization of the product amine by alkylation, acylation, sulfonylation and related procedures well known to those skilled in the art. If $R^{41}$ incorporates a leaving group, for example, a terminal bromine atom, this group may be displaced by an appropriate nucleophile, for example, sodium methyl mercaptide to give in this case, a thioether which may be the desired product or can be itself further manipulated, for example by oxidation to a sulfoxide or sulfone using standard reaction conditions. Other nucleophiles which may be employed to produce intermediates leading to compounds of this invention include: sodium cyanide, sodium methoxide, sodium azide, morpholine and others. When $R_{41}$ incorporates a ketal group, this group may be hydrolzyed at a convenient point in the synthesis to provide a keto group. This group in turn may be further manipulated, for example by reduction to an alcohol or conversion to derivative such as an oxime.

Examples of the application of these methods to the synthesis of compounds of formula 23 are provided in Chen, et al. WO 9910313.

Reaction Scheme 7.

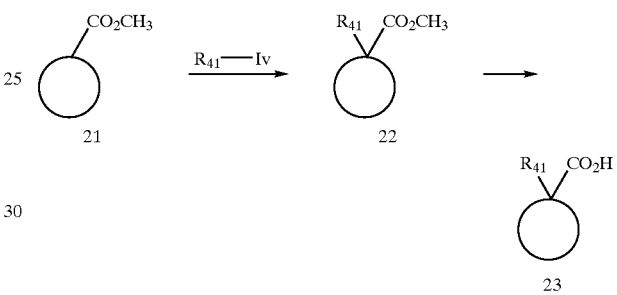

In general, ortho-substituted aromatic acids needed for the preparation of compounds in which $R^1$=Y-1 can be prepared as exemplified in Chen, et al., WO9910312.

For the synthesis of 2-chloro-6-alkylbenzoic acids of formula 28, wherein $R_{43}$ is lower alkyl or cycloalkyl, the procedure described in Reaction Scheme 8 is particularly suitable. Thus a commercially available aldehyde of formula 24 is converted to the imine 25 wherein R42 is lower alkyl, preferably butyl, by treatment with butylamine in an inert, hydrophobic organic solvent, for example heptane. The resulting compound of formula 25 is treated with an excess of a Grignard derivative 26 in an inert solvent, for example THF, followed by acid treatment during the workup to give an aldehyde of formula 27. Oxidation of 27 to an acid of formula 28 can be carried out by conventional means, for example by treatment of a solution of 27 in a suitable solvent such as aqueous acetonitrile with sodium chlorite and 30% hydrogen peroxide at or below room temperature.

Reaction Scheme 8

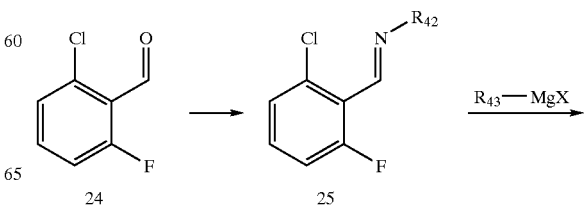

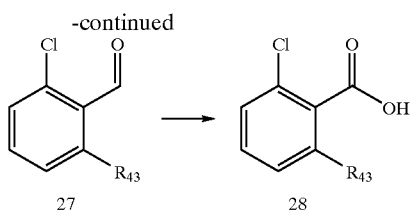

It may be desirable to prepare prodrug esters of the compounds of this invention for which it would be more convenient to introduce the ester moiety at the end of the synthesis. For this purpose, a variety of common techniques for the formation of esters from carboxylic acids may be employed. Typical methods which may be useful would include, coupling of an alcohol to the carboxylic acid in the presence of acid, for example hydrochloric acid, a procedure commonly known as a Fisher esterification. Alternatively, a diimide mediated coupling between the carboxylic acid and an alcohol may be employed with the optional use of a promoter such as 4,4-dimethylaminopyridine. A typical diimide is dicyclohexylcarbodiimide. Another alternative is to treat the carboxylic acid with a reactive alkyl halide, for example, an alkyl iodide or an acyloxymethyl chloride in the presence of a base, for example sodium bicarbonate and an inert solvent, for example DMF. The particular choice of method will be determined by the nature of the particular combination of carboxylic acid and desired ester moiety and will be apparent to one skilled in the art. Ester groups which may constitute prodrugs may be introduced at any convenient point in the synthesis. For example the group $P_2$ in formula 1 may represent a desirable prodrug ester and be retained in the final product.

EXAMPLES

The Examples which follow are for purposes of illustration and are not intended to limit the invention in any way.

General Methods: Melting points were taken on a Thomas-Hoover apparatus and are uncorrected. Optical rotations were determined with a Perkin-Elmer model 241 polarimeter. $^1$H-NMR spectra were recorded with Varian XL-200, Mercury 300 and Unityplus 400 MHz spectrometers, using tetramethylsilane (TMS) as internal standard. Electron impact (EI, 70 ev) and fast atom bombardment (FAB) mass spectra were taken on VG Autospec or VG 70E-HF mass spectrometers. Silica gel used for column chromatography was Mallinkrodt SiliCar 230–400 mesh silica gel for flash chromatography; columns were run under a 0–5 psi head of nitrogen to assist flow. Thin layer chromatograms were run on glass thin layer plates coated with silica gel as supplied by E. Merck (E. Merck # 1.05719) and were visualized by viewing under 254 nm UV light in a view box, by exposure to $I_2$ vapor, or by spraying with either phosphomolybdic acid (PMA) in aqueous ethanol, or after exposure to $Cl_2$, with a 4,4'-tetramethyldiaminodiphenylmethane reagent prepared according to E. Von Arx, M. Faupel and M Brugger, *J. Chromatography*, 1976, 120, 224–228.

Reversed phase high pressure liquid chromatography (RP-HPLC) was carried out using a Rainin HPLC employing a 41.4×300 mm, 8 μM, Dynamax™ C-18 column at a flow of 49 mL/min employing a gradient of acetonitrile:water (each containing 0.75% TFA) typically from 5 to 95% acetonitrile over 35–40 min. HPLC conditions are typically described in the format (5-95-35-214); this refers to a linear gradient of from 5% to 95% acetonitrile in water over 35 min while monitoring the effluent with a UV detector at a wavelength of 214 nM.

Methylene chloride (dichloromethane), 2-propanol, DMF, THF, toluene, hexane, ether, and methanol, were Fisher reagent grade and were used without additional purification except as noted, acetonitrile was Fisher or Baker hplc grade and was used as is.

Definitions as used herein:
THF is tetrahydrofuran,
DMF is N,N-dimethylformamide,
DMA is N,N-dimethylacetamide
HOBT is 1-hydroxybenzotriazole,
BOP is [(benzotriazole-1-yl)oxy]tris-(dimethylamino) phosphonium hexafluorophosphate,
HATU is O-(7-azabenzotriazol-1-yl)-1,1,3,3-tetramethyluronium hexafluorophosphate
HBTU is O-benzotriazole-N,N,N',N',-tetramethyluronium hexafluorophosphate,
DIPEA is diisopropylethylamine,
DMAP is 4-(N,N-dimethylamino)pyridine
DPPA is diphenylphosphoryl azide
DPPP is 1,3-bis(diphenylphosphino)propane
DBU is 1,8-diazabicyclo[5.4.0]undec-7-ene
NaH is sodium hydride
brine is saturated aqueous sodium chloride solution
TLC is thin layer chromatography
LDA is lithium diisopropylamide
BOP-Cl is bis(2-oxo-3-oxazolidinyl)phosphinic chloride
NMP is N-methyl pyrrolidinone
Lawesson's reagent is [2,4-bis(4-methoxyphenyl)-1,3-dithia-2,4-diphosphetane-2,4-disulfide]
NIS is N-iodosuccinimide.

Silica gel chromatography on Biotage columns refers to use of a flash chromatography system supplied by the Biotage Division of the Dyax Corporation employing prepacked 40 g (40 s columns), 90 g (40 m columns) or 800 g (75 m columns). Elution is carried out with hexane-ethyl acetate mixtures under 10–15 psi nitrogen pressure.

Example 1

N-[(1,1-dimethylethoxy)carbonyl]-4-[(tributyl) stannyl]-L-phenylalanine methyl ester

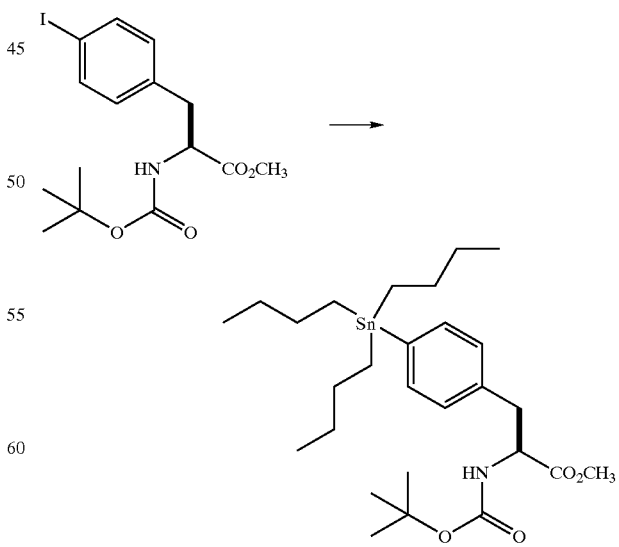

A solution of N-[(1,1-dimethylethoxy)carbonyl]-4-iodo-L-phenylalanine methyl ester (5.3 g, 13 mmol) and hexabutylditin (27.5 mL, 54 mmol) in toluene (50 mL) was deoxygenated by alternately freezing the mixture in a liquid nitrogen bath under vacuum and thawing under argon (3×).

Tetrakis(triphenylphosphine)palladium was added (280 mg, 0.22 mmol) and the reaction mixture was heated to reflux for 45 min as the color changed from yellow to black. TLC (1:6 ethyl acetate:hexane) indicated the presence of some starting iodide and an additional portion (140 mg, 0.11 mmol) of the catalyst was added. Reflux was continued for 1 hr. The mixture was allowed to cool and was concentrated. The residue was taken up in hexane (200 mL) and triethylamine (30 mL), stirred for 30 min and was filtered. The filtrate was concentrated and was chromatographed over a dry silica gel column containing 150 g of silica gel and eluting with hexane followed by 1:6 ethyl acetate:hexanes to give N-[(1,1-dimethylethoxy)carbonyl]-4-[(tributyl)stannyl]-L-phenylalanine methyl ester (5.7 g, 77%) as a clear oil. LR(+)LSIMS (C27H47NO4Sn): m/z 1081 (2M-C4H9) 570 (M+H).

Example 2

2-Amino-3-bromo-5-chloropyridine

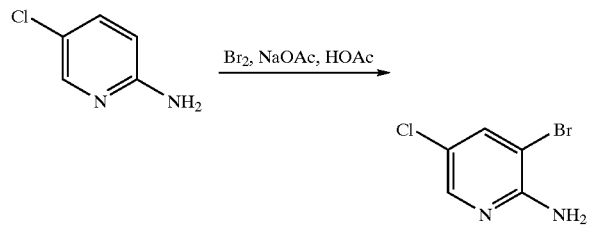

A suspension of 2-amino-5-chloropyridine (5.14 g, 40 mmol) and anhydrous sodium acetate (3.29 g, 40 mmol) in acetic acid (25 mL) was mechanically stirred and warmed to a bath temperature of 45° C. A solution of bromine (2.1 mL, 40 mmol) in acetic acid (2 mL) was added over 1 hour. The resulting orange mixture was cooled to 15° C. and filtered. The solids were taken up in 400 mL of water, the suspension made basic by addition of 1 N NaOH and the suspension extracted with ethyl acetate (5×100 mL). The combined extracts were washed with 10% NaHSO$_3$ (1×100 mL) and were dried over MgSO$_4$. Concentration afforded 2-amino-3-bromo-5-chloropyridine (4 g, 48), mp 82–84° C.

Example 3

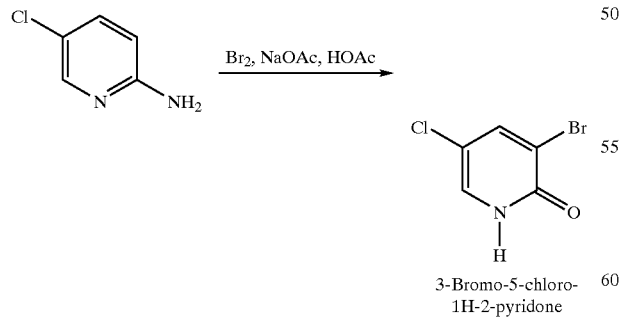

3-Bromo-5-chloro-1H-2-pyridone

A solution of 2-amino-3-bromo-5-chloropyridine (4.0 g, 19.3 mmol) in water (30 mL) and conc. HCl (5.2 mL) was cooled with an ice bath to 0° C. and was treated with a solution of sodium nitrite (1.33 g, 19.3 mmol) in water (12 mL) over 10 min. The mixture was stirred for an additonal 10 min and allowed to warm to room temperature over 48 hr. The mixture was filtered. The solids were washed with water, then with CCl$_4$ and were dried under vacuum at 50° C. for 3 hr to give 3-bromo-5-chloro-1H-2-pyridone (2.77 g, 69%), mp 173.5–175° C.

Example 4

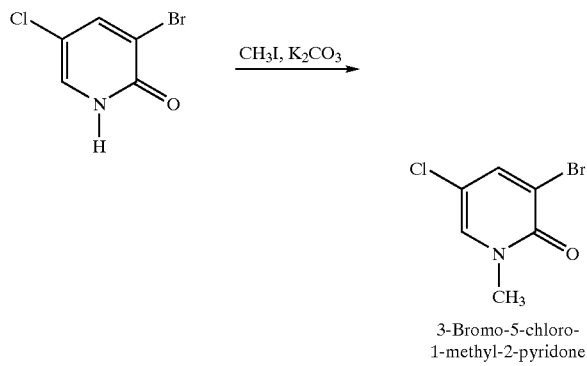

3-Bromo-5-chloro-1-methyl-2-pyridone

A mixture of 3-bromo-5-chloro-1H-2-pyridone (930 mg, 4.46 mmol), potassium carbonate (1.25 g, 9.1 mmol) and iodomethane (2.8 mL, 45 mmol) in 10 mL of DME was heated to reflux for 18 hr. The mixture was filtered hot and concentrated. The residue was recrystallized from ethyl acetate to give 3-bromo-5-chloro-1-methyl-2-pyridone (740 mg, 74%), mp 162–163° C. HRMS (C6H5BrClNO): Obs. Mass 220.9249. Calcd. Mass 220.9243 (M+H).

Example 5

4-(5-Chloro-1-methyl-2-oxo-3-pyridinyl)-N-[(1,1-dimethylethoxy)carbonyl]-L-phenylalanine methyl ester

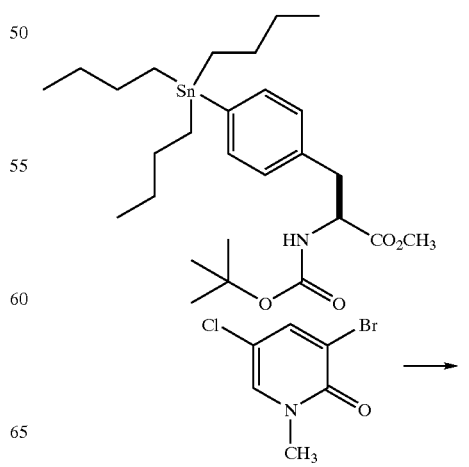

-continued

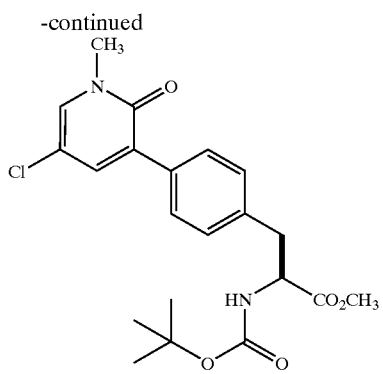

A solution of 3-bromo-5-chloro-1-methyl-2-pyridone (660 mg, 2.97 mmol) and N-[(1,1-dimethylethoxy)carbonyl]-4-[(tributyl)stannyl]-L-phenylalanine methyl ester (1.7 g, 2.99 mmol) in DMF (30 mL) was deoxygenated by alternately freezing the mixture in a liquid nitrogen bath under vacuum and thawing under argon (3x). Tetrakis(triphenylphosphine)palladium (140 mg, 0.20 mmol) was added and the mixture was heated to 90° C. for 3 hr as the mixture turned dark. TLC indicated that the reaction was not complete and an additional 140 mg portion of the catalyst was added and heating continued for 4 hr. The mixture was allowed to cool and was diluted with dichloromethane and was filtered through a pad of celite. The filtrate was evaporated to dryness and the residue was dissolved in 1:1 ether:ethyl acetate (60 mL). The solution was washed with water (3×10 mL) and brine (1×10 mL) and was dried (MgSO$_4$). The residue obtained upon concentration was chromatographed over 150 g of silica gel eluting with 7:3 ethyl acetate:hexane to give 4-(5-chloro-1-methyl-2-oxo-3-pyridinyl)-N-[(1,1-dimethylethoxy)carbonyl]-L-phenylalanine methyl ester (670 mg, 54%). LRMS-Electrospray: m/z 863 (2M+Na), 858 (2M+NH4), 443 (M+Na), 438 (M+NH4), 421(M+H).

Example 6

4-(5-chloro-1-methyl-2-oxo-3-pyridinyl)-L-phenylalanine methyl ester hydrochloride

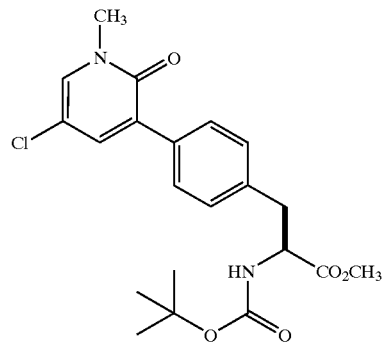

-continued

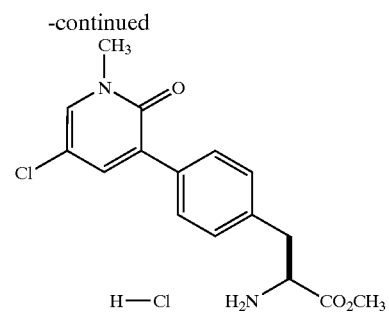

A solution of 4-(5-chloro-1-methyl-2-oxo-3-pyridinyl)-N-[(1,1-dimethylethoxy)carbonyl]-L-phenylalanine methyl ester (210 mg, 0.50 mmol) in 4 N HCl in dioxane (10 mL) was stirred for 1 hr and was concentrated to give 4-(5-chloro-1-methyl-2-oxo-3-pyridinyl)-L-phenylalanine methyl ester (140 mg) as a white powder. LR(+)LSIMS: m/z 641 (2M+H), 321 (M+H).

Example 7

N-[(2-Chloro-6-methylphenyl)carbonyl]-4-(5-chloro-1-methyl-2-oxo-3-pyridinyl)-L-phenylalanine methyl ester

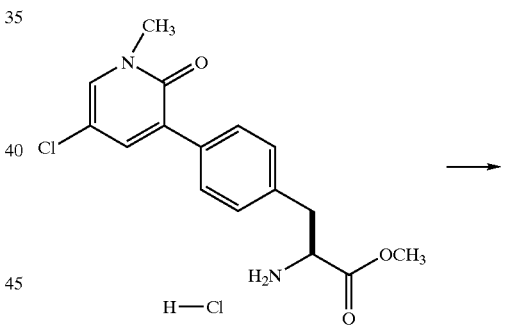

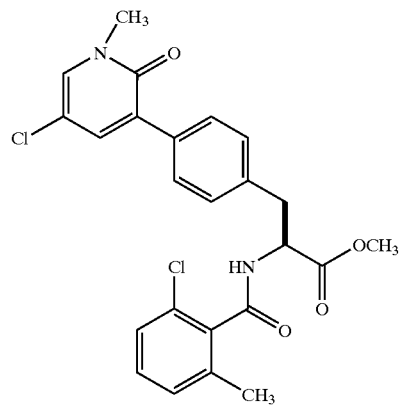

A solution of 4-(5-chloro-1-methyl-2-oxo-3-pyridinyl)-L-phenylalanine methyl ester hydrochloride (89.5 mg, 0.25 mmol), 2-chloro-6-methylbenzoic acid (47 mg, 0.28 mmol), DIEA (175 μL, 1.0 mmol) and HBTU (133 mg, 0.35 mmol) in DMF (3 mL) was stirred at room temperature for 4 hr. The mixture was concentrated, the residue was dissolved in ethyl acetate (15 mL), was washed with 0.5 N HCl (1×5 mL), sat. NaHCO₃ (1×5 mL), brine (1×5 mL) and was dried (MgSO₄). The residue obtained upon evaporation was chromatographed on 25 g of silica gel, eluting with 3:1 ethyl acetate-:hexane to give N-[(2-chloro-6-methylphenyl)carbonyl]-4-(5-chloro-1-methyl-2-oxo-3-pyridinyl)-L-phenylalanine methyl ester (54 mg). LR(+)LSIMS: m/z 962 (2M+NH4), 945 (2M+H), 490 (M+NH4), 473 (M+H (2 Cl)).

Example 8

N-[(2-chloro-6-methylphenyl)carbonyl]-4-(5-chloro-1-methyl-2-oxo-3-pyridinyl)-L-phenylalanine

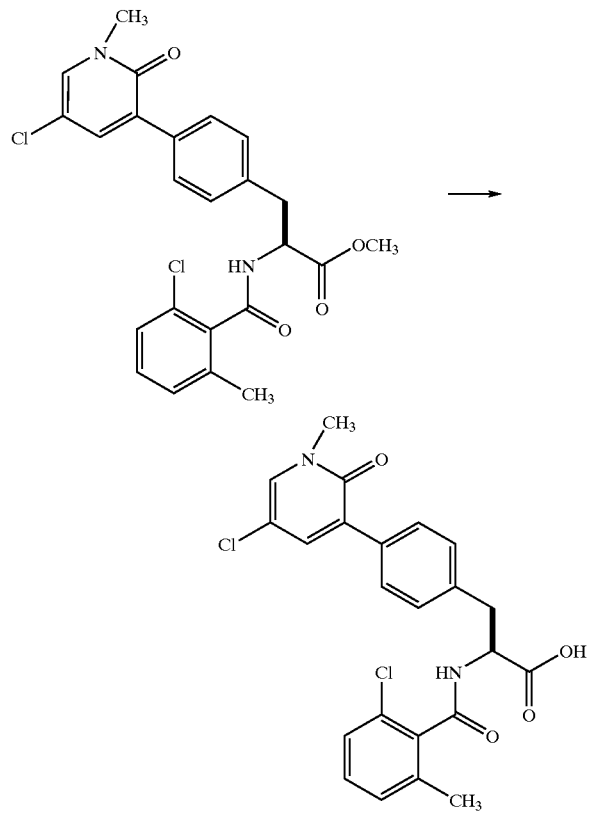

A solution of N-[(2-chloro-6-methylphenyl)carbonyl]-4-(5-chloro-1-methyl-2-oxo-3-pyridinyl)-L-phenylalanine methyl ester (51 mg, 0.108 mmol) in THF (3 mL) was treated with a solution of lithium hydroxide monohydrate (18 mg, 0.43 mmol) in water (1.0 mL). Additional THF was added to effect a clear solution and the reaction mixture was stirred 1 hr. TLC (ethyl acetate) indicated starting material was consumed. A few drops of acetic were added and the entire reaction mixture was applied to a 4×30 cm, C-18 reversed phase HPLC column and eluted with a linear gradient of acetonitrile in water of 5 to 95% over 35 min. The product containing fraction was lyophillyzed to give N-[(2-chloro-6-methylphenyl)carbonyl]-4-(5-chloro-1-methyl-2-oxo-3-pyridinyl)-L-phenylalanine (40 mg, 82%) as a white solid. LR-Electrospray: m/z positive ion, 481(M+Na), 459(M+H (2 Cl)); negative ion, 457 (M−H (2 Cl)).

Example 9

4-(5-chloro-1-methyl-2-oxo-3-pyridinyl)-N-[[1-(2-methoxyethyl)cyclopentyl]carbonyl]-L-phenylalanine methyl ester

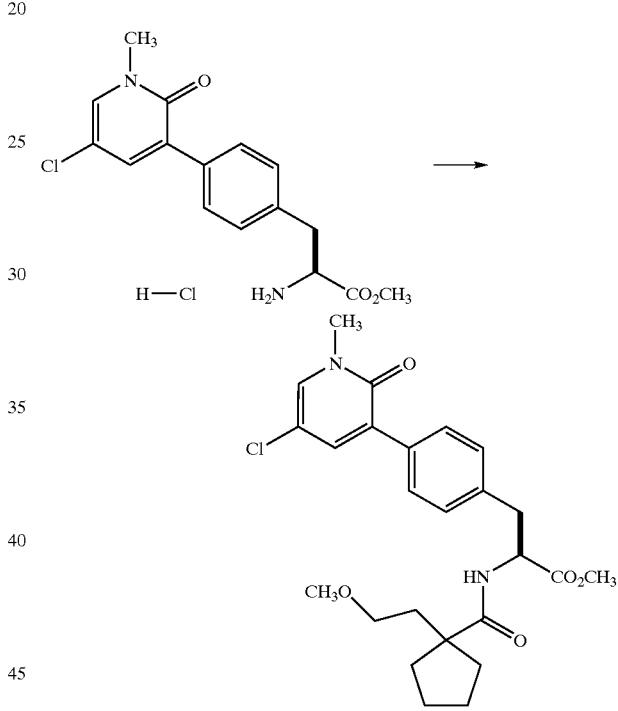

A solution of 4-(5-chloro-1-methyl-2-oxo-3-pyridinyl)-L-phenylalanine methyl ester hydrochloride (47.4 mg, 0.25 mmol), 1-(2-methoxyethyl)cyclopentane carboxylic acid (47 mg, 0.28 mmol), DIEA (175 μL, 1.0 mmol) and HBTU (133 mg, 0.35 mmol) in DMF (3 mL) was stirred at room temperature for 4 hr. The mixture was concentrated, the residue was dissolved in ethyl acetate (15 mL), was washed with 0.5 N HCl (1×5 mL), sat. NaHCO₃ (1×5 mL), brine (1×5 mL) and was dried (MgSO₄). The residue obtained upon evaporation was chromatographed on 25 g of silica gel, eluting with ethyl acetate to give 4-(5-chloro-1-methyl-2-oxo-3-pyridinyl)-N-[[1-(2-methoxyethyl)cyclopentyl]carbonyl]-L-phenylalanine methyl ester (70.5 mg, 59%). LR-Electrospray: m/z positive ion, 943 (2M+Na), 483 (M+Na), 478, (M+NH4), 461 (M+H); negative ion 919 (2M-H), 521, 459 (M−H).

Example 10

4-(5-chloro-1-methyl-2-oxo-3-pyridinyl)-N-[[1-(2-methoxyethyl)cyclopentyl]carbonyl]-L-phenylalanine

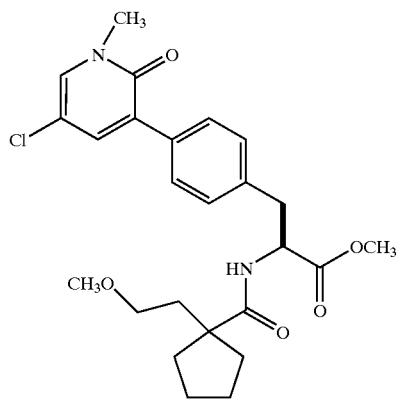

A solution of 4-(5-chloro-1-methyl-2-oxo-3-pyridinyl)-N-[[1-(2-methoxyethyl)cyclopentyl]carbonyl]-L-phenylalanine methyl ester (69 mg, 0.145 mmol) in THF (3 mL) was treated with a solution of lithium hydroxide monohydrate (24.3 mg, 0.58 mmol) in water (1.0 mL). Sufficient THF was added to the mixture to effect solution. The mixture was stirred 1 hr and a few drops of acetic acid were added. The entire reaction mixture was applied to a 4×30 cm, C-18 reversed phase HPLC column and eluted with a linear gradient of acetonitrile in water of 5 to 95% over 35 min. The product containing fraction was lyophilyzed to give 4-(5-chloro-1-methyl-2-oxo-3-pyridinyl)-N-[[1-(2-methoxyethyl)cyclopentyl]carbonyl]-L-phenylalanine (48 mg, 72%) as a white solid. LR-Electrospray: m/z positive ion 943 (2M+Na), 483 (M+Na), 478, (M+NH4), 461 (M+H); negative ion 919 (2M–H), 521, 459 (M–H).

Example 11

Benzyl-3-bromo-5-chloro-2-pyridone

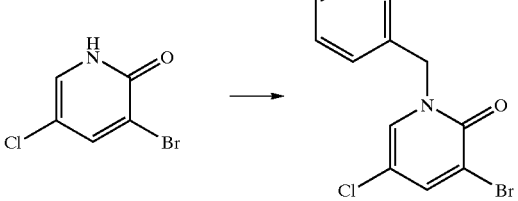

A mixture of 3-bromo-5-chloro-1H-2-pyridone (950 mg, 4.56 mmol), freshly ground potassium carbonate (1.26 g, 9.1 mmol) and tetrabutyl ammonium chloride (100 mg) in was stirred mechanically without solvent for 30 min and benzyl bromide (0.56 mL, 4.7 mmol) was added. The mixture was stirred at room temperature for 72 hr. The mixture was diluted with ethyl acetate and filtered, washing the solids with ethyl acetate. The filtrate was evaporated to dryness and the residue was triturated with several portions of hexane. The residue was chromatographed over 90 g of silica gel eluting with 3:1 hexane:ethyl acetate followed by 100% ethyl acetate to give 1-benzyl-3-bromo-5-chloro-2-pyridone (423 mg, 31%), mp 108–110° C. LR(+)LSIMS: m/z 595 (2M+H, 2 Cl, 2 Br), 298 (M+H, 1 Cl, 1 Br).

Example 12

4-(1-Benzyl-5-chloro-2-oxo-3-pyridinyl)-N-[(1,1-dimethylethoxy)carbonyl]-L-phenylalanine methyl ester

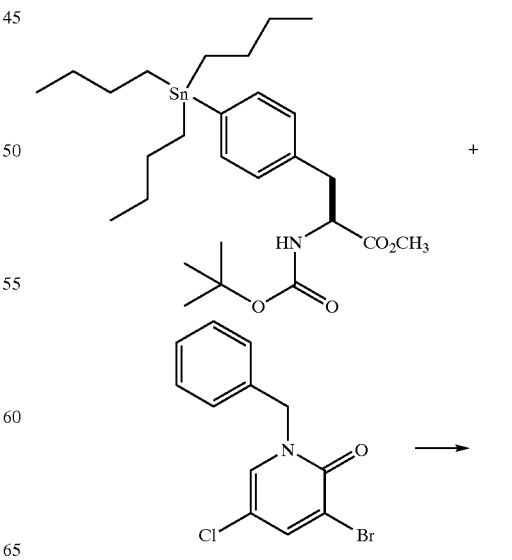

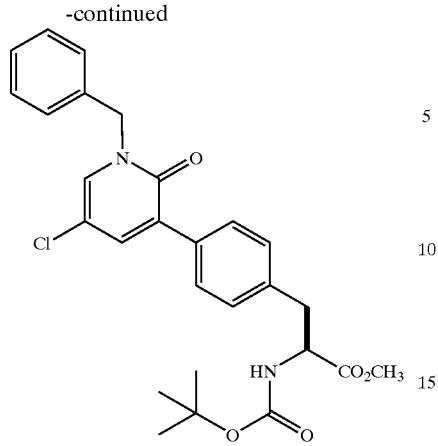

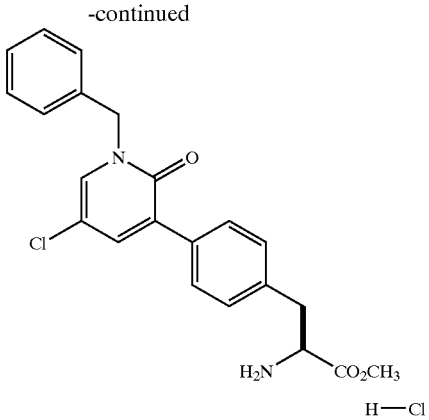

A solution of 1-benzyl-3-bromo-5-chloro-2-pyridone (296 mg, 0.98 mmol) and N-[(1,1-dimethylethoxy)carbonyl]-4-[(tributyl)stannyl]-L-phenylalanine methyl ester (560 mg, 0.99 mmol) in DMF (15 mL) was deoxygenated by alternately freezing the mixture in a liquid nitrogen bath under vacuum and thawing under argon (3×). Bis(triphenylphosphine)palladium dichloride (80 mg, 0.11 mmol) was added and the mixture was heated to 90° C. for 4 hr as the mixture turned dark. An additional 60 mg of the catalyst was added and heating continued for 2 hr. The mixture was allowed to cool, was diluted with dichloromethane, and was filtered through a pad of celite. The filtrate was evaporated to dryness and the residue was chromatographed over 150 g of silica gel eluting with 1:2 ethyl acetate:hexane to give 4-(1-benzyl-5-chloro-2-oxo-3-pyridinyl)-N-[(1,1-dimethylethoxy)carbonyl]-L-phenylalanine methyl ester (255 mg, 52%). LMS-Electrospray: m/z 1015 (2M+Na) (4 Cl) 519 (M+Na) 514 (M+NH4) 497 (M+H).

Example 13

4-(1-Benzyl-5-chloro-2-oxo-3-pyridinyl)-L-phenylalanine methyl ester hydrochloride A solution of 1-benzyl-4-(5-chloro-2-oxo-3-pyridinyl)-N-[(1,1-dimethylethoxy)carbonyl]-L-phenylalanine methyl ester (248 mg, 0.50 mmol) in 4 N HCl in dioxane (10 mL) was stirred for 1 hr and was concentrated. The residue was triturated with ether (15 mL) and was filtered to give 4-(1-benzyl-5-chloro-2-oxo-3-pyridinyl)-L-phenylalanine methyl ester (202 mg, 94%) as a white powder. LR-Electrospray: m/z 1015 (2M+Na, 4 Cl), 519 (M+Na) 514 (M+NH4), 497 (M+H). HRMS: Obs. Mass 496.1774. Calcd. Mass 496.1765 (M+H).

Example 14

4-(1-Benzyl-5-chloro-2-oxo-3-pyridinyl)-N-[(2-chloro-6-methylphenyl)carbonyl]-L-phenylalanine methyl ester

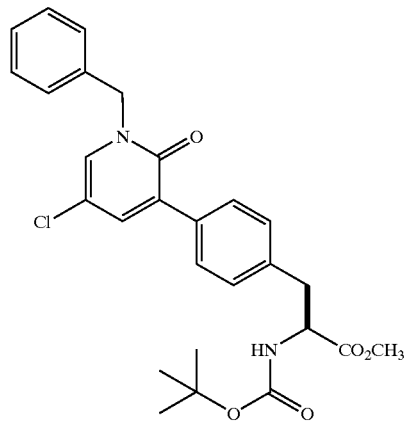

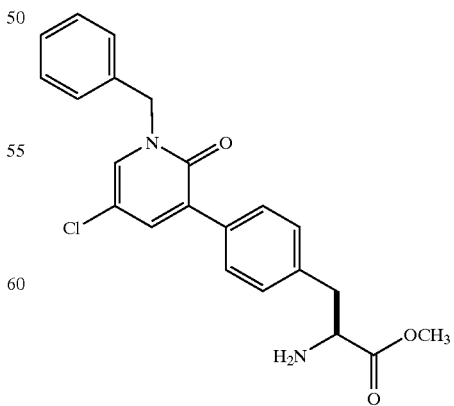

33

-continued

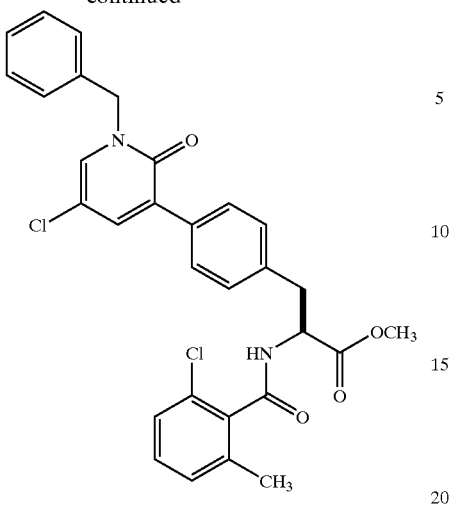

A solution of 4-(1-benzyl-5-chloro-2-oxo-3-pyridinyl)-L-phenylalanine methyl ester hydrochloride (100 mg, 0.23 mmol), 2-chloro-6-methylbenzoic acid (47 mg, 0.28 mmol), DIEA (200 μL, 1.2 mmol) and HBTU (133 mg, 0.35 mmol) in DMF (2 mL) was stirred at room temperature for 18 hr. The mixture was concentrated, the residue was dissolved in ethyl acetate (15 mL), was washed with 0.5 N HCl (1×5 mL), sat. NaHCO₃ (1×5 mL), brine (1×5 mL) and was dried (MgSO₄). The residue obtained upon evaporation was chromatographed on 25 g of silica gel, eluting with 45:55 ethyl acetate:hexane to give 4-(1-benzyl-5-chloro-2-oxo-3-pyridinyl)-N-[(2-chloro-6-methylphenyl)carbonyl]-L-phenylalanine methyl ester (74 mg, 58%). Obs. Mass 397.1313. Calcd. Mass 397.1320 (M+H)

Example 15

4-(1-Benzyl-5-chloro-2-oxo-3-pyridinyl)-N-[(2-chloro-6-methylphenyl)carbonyl]-L-phenylalanine

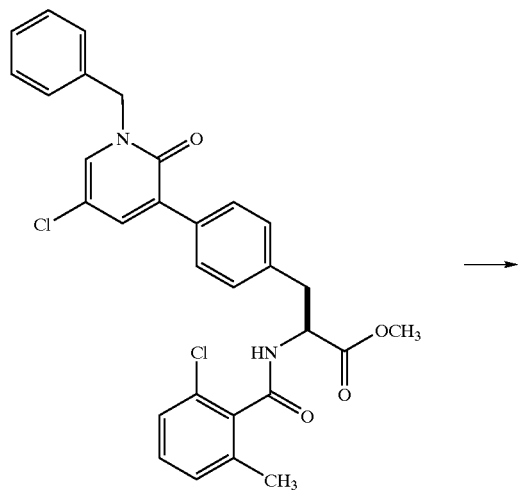

34

-continued

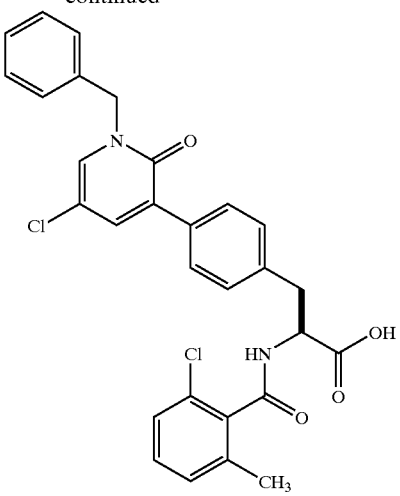

A solution of N-[(2-chloro-6-methylphenyl)carbonyl]-4-(1-benzyl-5-chloro-2-oxo-pyridinyl)-L-phenylalanine methyl ester (72 mg, 0.13 mmol) in THF (3 mL) was treated with a solution of lithium hydroxide monohydrate (22 mg, 0.52 mmol) in water (1.0 mL). Additional THF was added to effect a clear solution and the reaction mixture was stirred 1.5 hr at which time, TLC (ethyl acetate) indicated starting material was consumed. A few drops of acetic were added and the entire reaction mixture was applied to a 4×30 cm, C-18 reversed phase HPLC column and eluted with a linear gradient of acetonitrile in water of 5 to 95% over 35 min. The product containing fraction was lyophillyzed to give 4-(1-benzyl-5-chloro-2-oxo-3-pyridinyl)-N-[(2-chloro-6-methylphenyl)carbonyl]-L-phenylalanine (50 mg, 71%) as a white solid. LR-Electrospray: m/z negative ion 533 (M−H (2 Cl)); positive ion 557(M+Na), 552 (M+NH4), 535 (M+H (2 Cl)). HRMS: Obs. Mass 535.1190. Calcd. Mass 535.1191 (M+H).

Example 16

4-(1-Benzyl-5-chloro-2-oxo-3-pyridinyl)-N-[[1-(2-methoxyethyl)cyclopentyl]carbonyl]-L-phenylalanine methyl ester

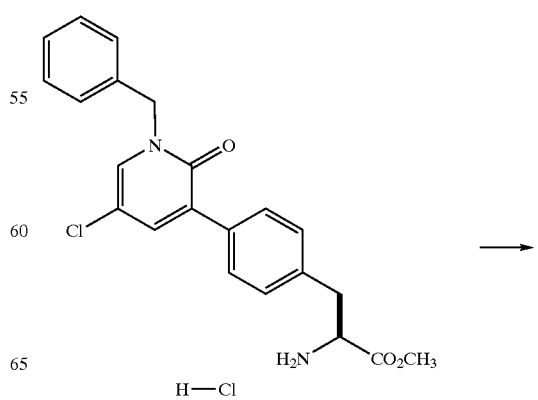

-continued

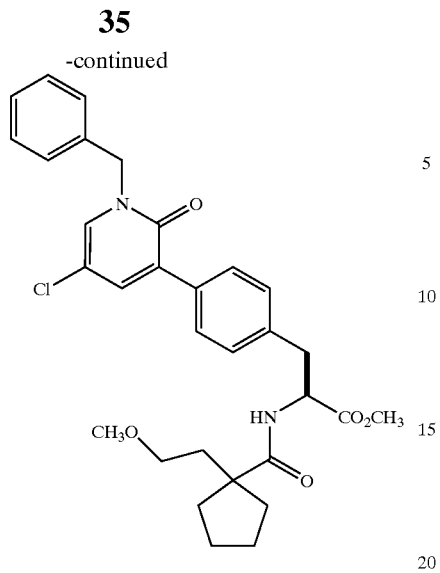

A solution of 4-(1-benzyl-5-chloro-2-oxo-3-pyridinyl)-L-phenylalanine methyl ester hydrochloride (100 mg, 0.25 mmol), 1-(2-methoxyethyl)cyclopentane carboxylic acid (47 mg, 0.28 mmol), DIEA (200 μL, 1.2 mmol) and HBTU (133 mg, 0.35 mmol) in DMF (2 mL) was stirred at room temperature for 18 hr. The mixture was concentrated, the residue was dissolved in ethyl acetate (15 mL), was washed with 0.5 N HCl (1×5 mL), sat. NaHCO$_3$ (1×5 mL), brine (1×5 mL) and was dried (MgSO$_4$). The residue obtained upon evaporation was chromatographed on 25 g of silica gel, eluting with 60:40 ethyl acetate:hexane to give 4-(1-benzyl-5-chloro-2-oxo-3-pyridinyl)-N-[[1-(2-methoxyethyl)cyclopentyl]carbonyl]-L-phenylalanine methyl ester (80 mg, 63%). LR-Electrospray: m/z 1123 (2M+Na), 1118 (2M+NH4), 573 (M+Na), 568 (M+NH4), 551 (M+H (1 Cl)). HRMS: Obs. Mass 551.2297. Calcd. Mass 551.2313 (M+H).

Example 17

4-(1-Benzyl-5-chloro-2-oxo-3-pyridinyl)-N-[[1-(2-methoxyethyl)cyclopentyl]carbonyl]-L-phenylalanine

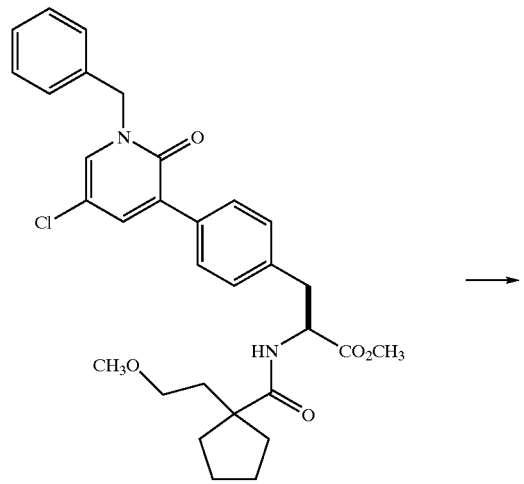

-continued

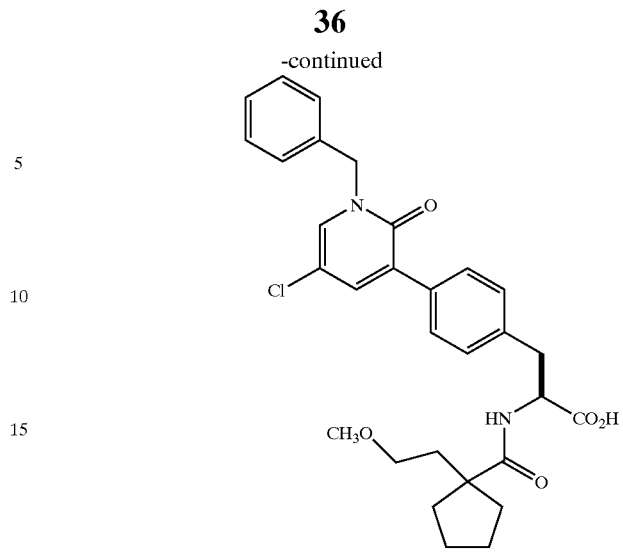

A solution of 4-(1-benzyl-5-chloro-2-oxo-3-pyridinyl)-N-[[1-(2-methoxyethyl)cyclopentyl]carbonyl]-L-phenylalanine methyl ester (78 mg, 0.142 mmol) in THF (3 mL) was treated with a solution of lithium hydroxide monohydrate (24 mg, 0.57 mmol) in water (1.0 mL). Sufficient THF was added to the mixture to effect solution. The mixture was stirred 1 hr and a few drops of acetic acid were added. The entire reaction mixture was applied to a 4×30 cm, C-18 reversed phase HPLC column and eluted with a gradient of acetonitrile in water of 5- to 95% over 35 min. The product containing fraction was lyophillyzed to give 4-(5-chloro-1-benzyl-2-oxo-3-pyridinyl)-N-[[1-(2-methoxyethyl)cyclopentyl]carbonyl]-L-phenylalanine (45 mg, 60%) as a white solid. LRMS-Electrospray: m/z positive ion 559 (M+Na), 554 (M+NH4), 537 (M+H (1 Cl)); negative ion 535 (M−H (1 Cl)). HRMS: obs. mass 537.2151. calcd. mass 537.2156 (M+H).

Example 18

3-Bromo-1H-2-pyridone

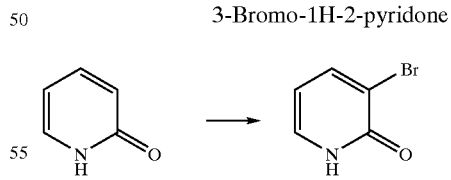

To a solution of 1H-2-pyridone (1.9 g, 20 mmol) in 1M aqueous potassium bromide (20 mL) was added a solution of bromine (3.2 g, 20 mmol) in 1 M aqueous potassium bromide (40 mL) over 5 min. The reaction was allowed to proceed overnight and the resulting precipitate was collected to give 1.4 g. Recrystallization from acetonitrile afforded 0.78 g of 3-bromo-1H-2-pyridone.

Example 19

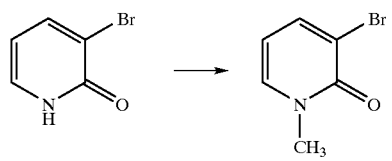

3-Bromo-1-methyl-2-pyridone

A mixture of 3-bromo-1H-2-pyridone (740 mg, 4.25 mmol), potassium carbonate (1.18 g, 8.5 mmol) and iodomethane (2.65 mL, 42.5 mmol) in DME (10 mL) was heated to reflux overnight. The mixture was filtered, washing with ethyl acetate and the filtrate was evaporated to dryness. The residue was purified by dry column chromatography over 27 g of silica gel, eluting with ethyl acetate to give 3-bromo-1-methyl-2-pyridone (0.63 g, 79%). LRMS (electrospray), positive ion, 188 (M+H).

Example 20

3-bromo-1-methyl-2-pyridone and 3,5-dibromo-1-methyl-2-pyridone

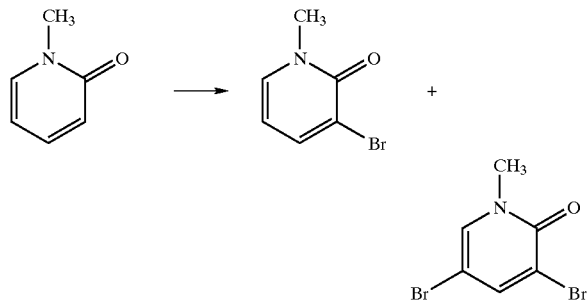

A solution of 1-methyl-2-pyridone (2.73 g, 25 mmol) and bromine (1.4 mL, 27 mmol) in glacial acetic acid (150 mL) was stirred 48 hr at room temperature. The mixture was concentrated. The residue was taken up in water (100 mL), made basic to litmus paper with 10 N sodium hydroxide and was extracted with dichloromethane (3×50 mL). The combined extracts were washed with brine (30 mL) and dried (MgSO$_4$). Filtration and evaporation of the solvent gave 4.7 g, which was purified by dry chromatography over 150 g of silica gel, eluting with 1:6 ethyl acetate:hexane followed by 1:1 ethyl acetate:hexane. The first compound to elute was 3,5-dibromo-1-methyl-2-pyridone (2.0 g, 30%), LR-Electrospray: m/z 266 (M+H (2 Br)). NMR(CDCl$_3$) δ 3.597 (s, 3H), 7.426 (d, j=2.7, 11H), 7.791 (d, j=2.7, 1H). The second compound to elute was 3-bromo-1-methyl-2-pyridone (1.39 g, 30%), LR-Electrospray: m/z positive ion 251 (M+Na$^+$ CH$_3$CN), 188 (M+H).

Example 21

N-[(1,1-Dimethylethoxyl)carbonyl]-4-(1-methyl-2-oxo-3-pyridinyl)-L-phenylalanine methyl ester

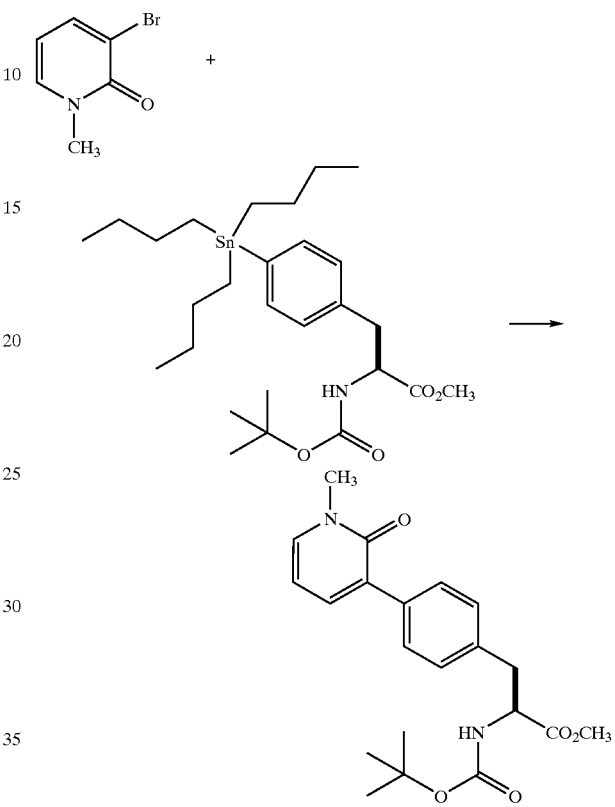

A solution of 3-bromo-1-methyl-2-pyridone (94 mg, 0.50 mmol) and N-[(1,1-dimethylethoxy)carbonyl]-4-[(tributyl) stannyl]-L-phenylalanine methyl ester (284 mg, 0.50 mmol) in DMF (3 mL) was deoxygenated by alternately freezing the mixture in a liquid nitrogen bath under vacuum and thawing under argon (3×). bis(triphenylphosphine) palladium dichloride (40 mg, 0.057 mmol) was added and the mixture was heated to 90° C. for 3 hr as the mixture turned dark. TLC indicated that the reaction was not complete and an additional 20 mg portion of the catalyst was added and heating continued for 4 hr. The mixture was allowed to cool and was diluted with dichloromethane (20 mL) and was filtered through a pad of celite. The filtrate was evaporated to dryness and the residue was dissolved in 1:1 ether:ethyl acetate (20 mL). The solution was washed with water (1×10 mL), 5% potassium fluoride (2×5 mL) and water (1×10 mL) and was dried (MgSO$_4$). The residue obtained upon concentration was chromatographed over 25 g of silica gel eluting with 4:6 ethyl acetate:hexane to give N-[(1,1-dimethylethoxyl)carbonyl]-4-(1-methyl-2-oxo-3-pyridinyl)-L-phenylalanine methyl ester (64 mg, 33%). LRMS-Electrospray: m/z positive ion, 795 (2M+Na) 409 (M+Na) 387 (M+H). HRMS: Obs. Mass 387.1935. Calcd. Mass 387.1920 (M+H).

Example 22

4-(1-methyl-2-oxo-3-pyridinyl)-L-phenylalanine methyl ester hydrochloride

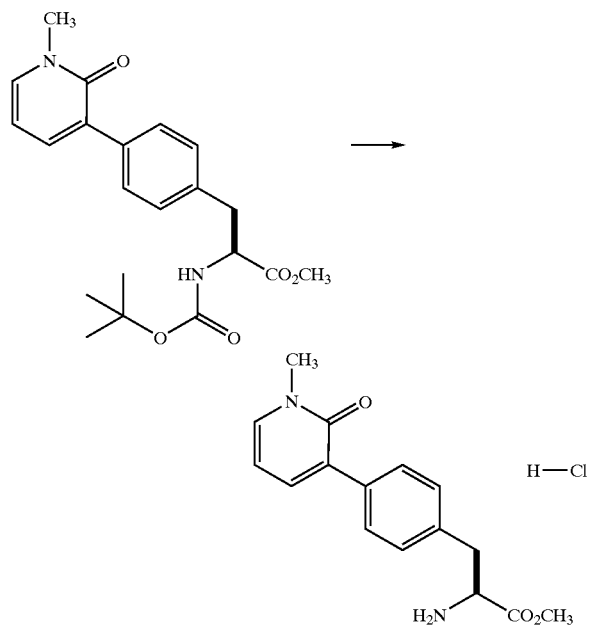

A solution of N-[(1,1-dimethylethoxyl)carbonyl]-4-(1-methyl-2-oxo-3-pyridinyl)-L-phenylalanine methyl ester (60 mg, 0.155 mmol) in 4 N HCl in dioxane (4 mL) was stirred for 2 hr and was concentrated. The residue was triturated with several portions of ether to give 4-(1-methyl-2-oxo-3-pyridinyl)-L-phenylalanine methyl ester hydrochloride (55 mg, quant) as a white powder. LRMS-Electrospray: m/z positive ion 573 (2M+H) 328 (M+H+CH3CN) 319 (M+H+CH3OH) 287 (M+H). HRMS: Obs. Mass 287.1396. Calcd. Mass 287.1396 (M+H)

Example 23

N-[(2-bromo-5-methoxyphenyl)carbonyl]-4-(1-methyl-2-oxo-3-pyridinyl)-L-phenylalanine methyl ester

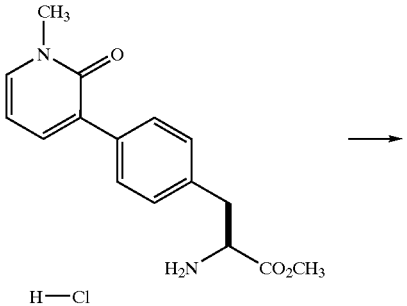

A solution of 4-(1-methyl-2-oxo-3-pyridinyl)-L-phenylalanine methyl ester hydrochloride (52 mg, 0.16 mmol), 2-bromo-5-methoxybenzoic acid (45 mg, 0.19 mmol), DIEA (140 µL, 0.80 mmol) and HBTU (85 mg, 0.22 mmol) in DMF (3 mL) was stirred at room temperature for 18 hr. The mixture was concentrated, the residue was dissolved in ethyl acetate (15 mL), was washed with 0.5 N HCl (1×5 mL), sat. NaHCO$_3$ (1×5 mL), brine (1×5 mL) and was dried (MgSO$_4$). The residue obtained upon evaporation (85 mg) was chromatographed on 25 g of silica gel, eluting with ethyl acetate to give N-[(2-bromo-5-methoxyphenyl)carbonyl]-4-(1-methyl-2-oxo-3-pyridinyl)-L-phenylalanine methyl ester (54 mg, 68%). HRMS: Obs. Mass 499.0872. Calcd. Mass 499.0869 (M+H)

Example 24

N-[(2-bromo-5-methoxyphenyl)carbonyl]-4-(1-methyl-2-oxo-3-pyridinyl)-L-phenylalanine

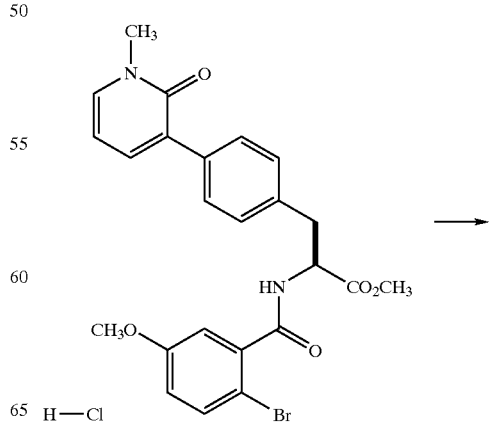

41

-continued

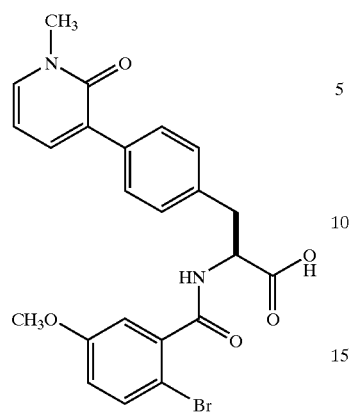

Example 25

4-(5-bromo-1-methyl-2-oxo-3-pyridinyl)-N-[(1,1-dimethylethoxy)carbonyl]-L-phenylalanine methyl ester

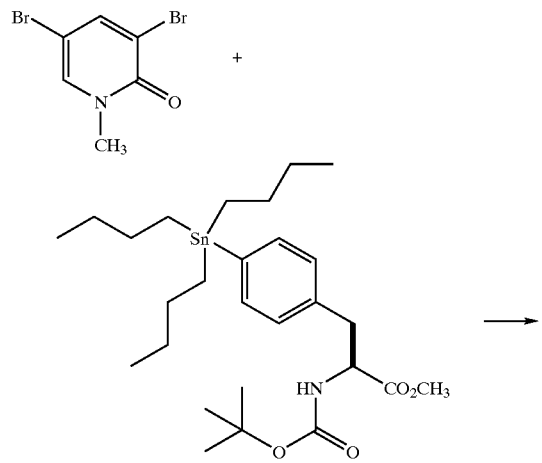

42

-continued

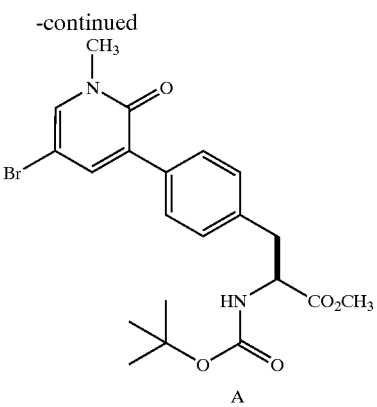

A

A solution of N-[(2-bromo-5-methoxyphenyl)carbonyl]-4-(1-methyl-2-oxo-3-pyridinyl)-L-phenylalanine methyl ester (52 mg, 0.104 mmol) in THF (3 mL) was treated with a solution of lithium hydroxide monohydrate (20 mg, 0.47 mmol) in water (1.0 mL). Methanol (0.5 mL) was added to effect a clear solution and the reaction mixture was stirred 18 hr. Acetic acid (0.5 mL) was added, the entire reaction mixture was applied to a 4×30 cm, C-18 reversed phase HPLC column and eluted with a gradient of acetonitrile in water of 5 to 95% over 35 min. The product containing fraction was lyophillyzed to give N-[(2-bromo-5-methoxyphenyl)carbonyl]-4-(1-methyl-2-oxo-3-pyridinyl)-L-phenylalanine (39 mg, 78%) as a white solid. HRMS: Obs. Mass 485.0703 Calcd. Mass 485.0712 (M+H).

solution of 3,5-dibromo-1-methyl-2-pyridone (267 mg, 1.0 mmol) and N-[(1,1-dimethylethoxy)carbonyl]-4-[(tributyl)stannyl]-L-phenylalanine methyl ester (568 mg, 1.0 mmol) in DMF (7 mL) was deoxygenated by alternately freezing the mixture in a liquid nitrogen bath under vacuum and thawing under argon (3×). bis(triphenylphosphine)palladium dichloride (80 mg, 0.11 mmol) was added and the mixture was heated to 90° C. for 3 hr as the mixture turned dark. TLC indicated that the reaction was not complete and an additional 40 mg portion of the catalyst was added and heating continued for 4 hr. The mixture was allowed to cool and was diluted with dichloromethane (40 mL) and was filtered through a pad of celite. The filtrate was evaporated to dryness and the residue was dissolved in ethyl acetate (30 mL). The solution was washed with water (1×10 mL), 5% potassium fluoride (2×10 mL) and brine (1×5 mL) and was dried (MgSO$_4$). The residue obtained upon concentration was chromatographed over 45 g of silica gel eluting with 3:7 ethyl acetate:hexane to give 4-(5-bromo-1-methyl-2-oxo-3-pyridinyl)-N-[(1,1-dimethylethoxyl)carbonyl]-L-phenylalanine methyl ester (140 mg, 30%). FAB MS: 465 (M+H (1 Br)).

Example 26

4-(5-bromo-1-methyl-2-oxo-3-pyridinyl)-L-phenylalanine methyl ester hydrochloride

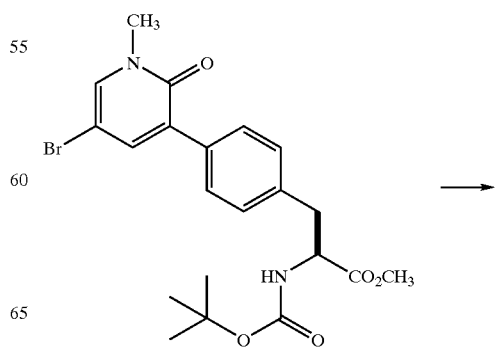

43

-continued

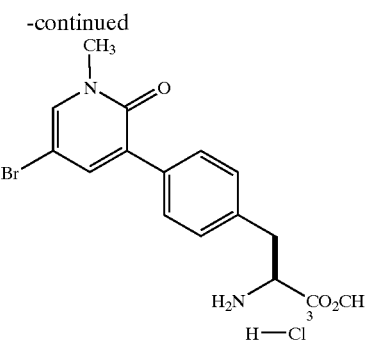

A solution of N-[(1,1-dimethylethoxy)carbonyl]-4-(5-bromo-1-methyl-2-oxo-3-pyridinyl)-L-phenylalanine methyl ester (135 mg, 0.29 mmol) in 4 N HCl in dioxane (5 mL) was stirred for 2 hr and was concentrated. The residue was triturated with several portions of ether to give 4-(5-bromo-1-methyl-2-oxo-3-pyridinyl)-L-phenylalanine methyl ester hydrochloride (120 mg, quant) as a white powder. LRMS-Electrospray: m/z positive ion 729, 2M+H (2 Br), 406 (M+H+CH3CN), 397 (M+H+CH3CN (1 Br)), 365 (M+H (1 Br)). HRMS: Obs. Mass 365.0504. Calcd. Mass 365.0501 (M+H).

Example 27

N-[(2-bromo-5-methoxyphenyl)carbonyl]-4-(5-bromo-1-methyl-2-oxo-3-pyridinyl)-L-phenylalanine methyl ester

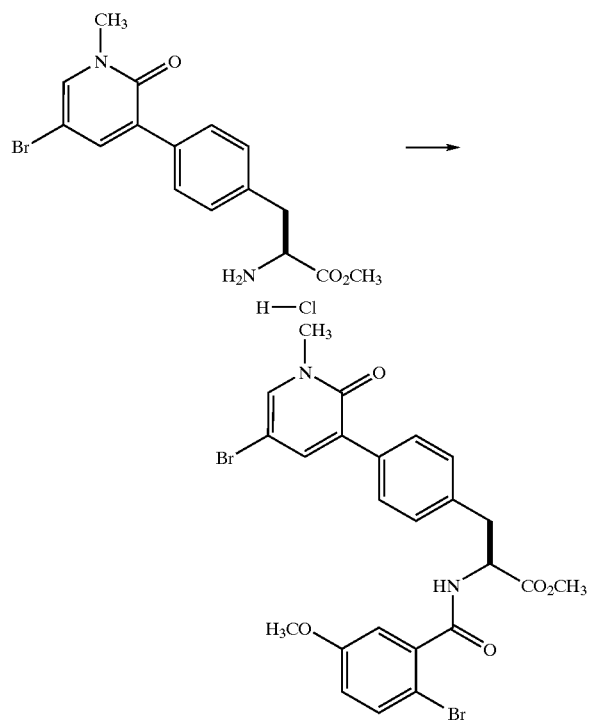

A solution of 4-(5-bromo-1-methyl-2-oxo-3-pyridinyl)-L-phenylalanine methyl ester hydrochloride (120 mg, 0.30 mmol), 2-bromo-5-methoxybenzoic acid (82 mg, 0.36 mmol), DIEA (260 μL, 1.5 mmol) and HBTU (157 mg, 0.41 mmol) in DMF (4 mL) was stirred at room temperature for 18 hr. The mixture was concentrated, the residue was

44 dissolved in ethyl acetate (15 mL), was washed with 0.5 N HCl (1×5 mL), sat. NaHCO₃ (1×5 mL), brine (1×5 mL) and was dried (MgSO₄). The residue obtained upon evaporation (180 mg) was chromatographed on 25 g of silica gel, eluting with 3:1 ethyl acetate:hexane to give N-[(2-bromo-5-methoxyphenyl)carbonyl]-4-(5-bromo-1-methyl-2-oxo-3-pyridinyl)-L-phenylalanine methyl ester (130 mg, 76%). HRMS: Obs. Mass 576.9959. Calcd. Mass 576.9973 (M+H)

Example 28

N-[(2-bromo-5-methoxyphenyl)carbonyl]-4-(5-bromo-1-methyl-2-oxo-3-pyridinyl)-L-phenylalanine

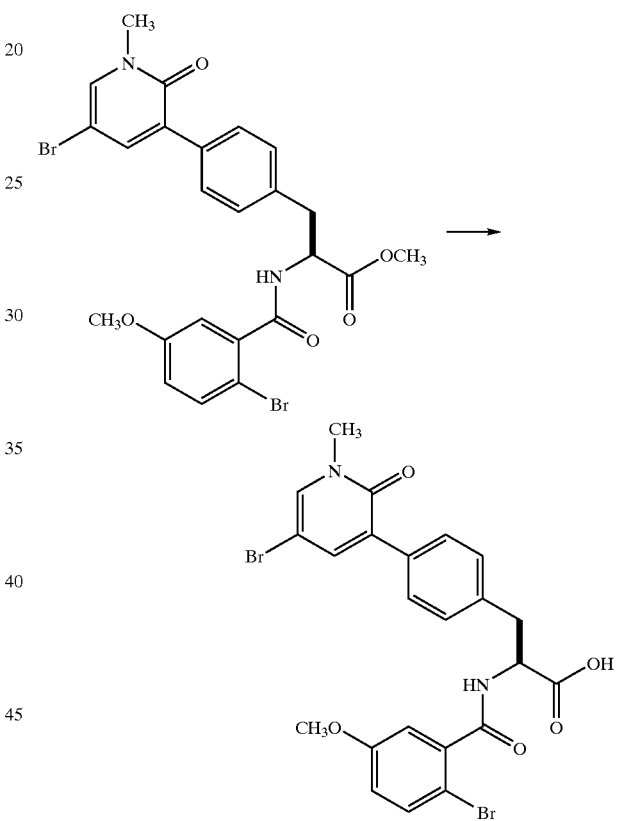

A solution of N-[(2-bromo-5-methoxyphenyl)carbonyl]-4-(5-bromo-1-methyl-2-oxo-3-pyridinyl)-L-phenylalanine methyl ester (29 mg, 0.05 mmol) in THF (3 mL) was treated with a solution of lithium hydroxide monohydrate (20 mg, 0.47 mmol) in water (1.0 mL). Methanol (0.5 mL) was added to effect a clear solution and the reaction mixture was stirred 18 hr. Acetic acid (0.5 mL) was added, the entire reaction mixture was applied to a 4×30 cm, C-18 reversed phase HPLC column and eluted with a gradient of acetonitrile in water of 5 to 95% over 35 min. The product containing fraction was lyophillyzed to give N-[(2-bromo-5-methoxyphenyl)carbonyl]-4-(5-bromo-1-methyl-2-oxo-3-pyridinyl)-L-phenylalanine (22 mg, 79%) as a white solid. HRMS: Obs. Mass 562.9814. Calcd. Mass 562.9817 (M+H).

Example 29

Preparation of N-[(2-chloro-6-methylphenyl)carbonyl]-4-(1-methyl-2-oxo-3-pyridinyl)-L-phenylalanine methyl ester

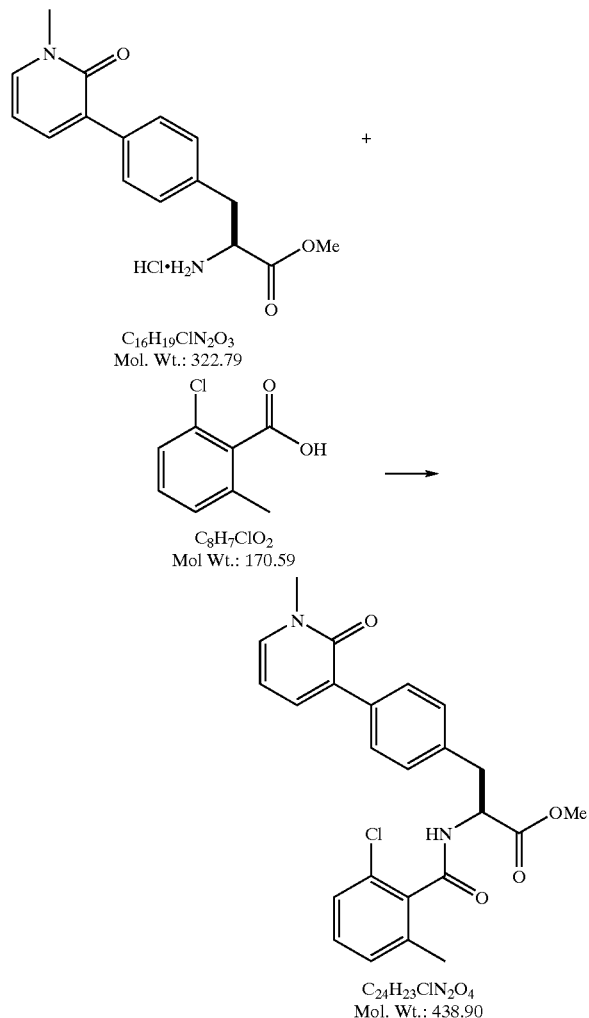

To a suspension of 4-(1-methyl-2-oxo-3-pyridinyl)-L-phenylalanine methyl ester hydrochloride salt (101 mg, 0.313 mmol), 2-chloro-6-methylbenzoic acid (60 mg, 0.35 mmol) and HBTU (133 mg, 0.35 mmol) in DMF (2 mL) was added DIEA (122 μL, 0.88 mmol) at room temperature. The resulting mixture was stirred for 15 h. Then, the mixture was poured into water (25 mL) and the organic compound was extracted into ethyl acetate (2×15 mL). The combined ethyl acetate extracts were washed successively with 0.5 N HCl (25 mL), saturated NaHCO$_3$ solution (25 mL), brine solution (25 mL) and were dried over anhydrous magnesium sulfate. Filtration of the drying agent and concentration gave the crude product which was purified by silica gel chromatography using a Biotage (40 s) column to afford 122 mg (88% yield) of N-[(2-chloro-6-methylphenyl)carbonyl]-4-(1-methyl-2-oxo-3-pyridinyl)-L-phenylalanine methyl ester as an amorphous white solid. FAB-HRMS m/e calcd for C$_{24}$H$_{23}$ClN$_2$O$_4$ (M+H) 439.1425. found 439.1414.

Example 30

Preparation of N-[(2-chloro-6-methylphenyl)carbonyl]-4-(1-methyl-2-oxo-3-pyridinyl)-L-phenylalanine

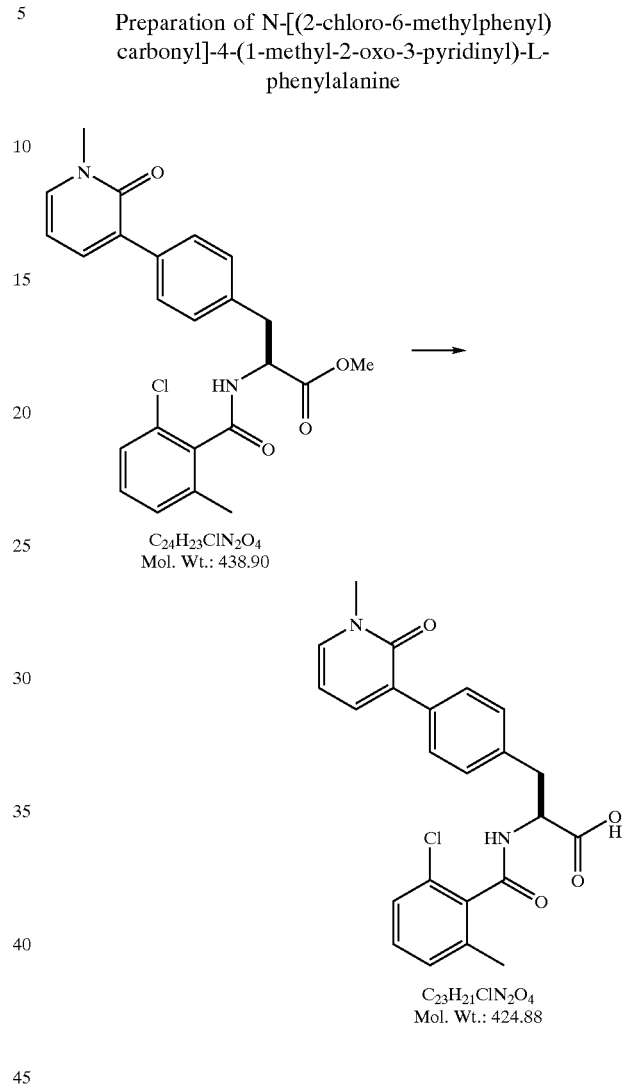

To a suspension of N-[(2-chloro-6-methylphenyl)carbonyl]-4-(1-methyl-2-oxo-3-pyridinyl)-L-phenylalanine methyl ester (118 mg, 0.269 mmol) in ethanol (6 mL) was added 1N aqueous sodium hydroxide solution (4 mL) at room temperature. The resulting solution was heated to 50° C. and stirred for 2 h. Then, the ethanol was removed under vacuum and the residue was diluted with water (25 mL). The aqueous solution was washed with diethyl ether (25 mL) to remove any neutral impurities. The aqueous layer was acidified with 1.0 N HCl and the product was extracted into ethyl acetate (2×25 mL). The combined organic extracts were washed with brine solution (50 mL) and were dried over anhydrous magnesium sulfate. Filtration of the drying agent and concentration afforded 81 mg (71% yield) of N-[(2-chloro-6-methylphenyl)carbonyl]-4-(1-methyl-2-oxo-3-pyridinyl)-L-phenylalanine as a white solid: mp 204–210° C. FAB-HRMS m/e calcd for C$_{23}$H$_{21}$ClN$_2$O$_4$ (M+H) 425.1268. found 425.1267.

Example 31

Preparation of N-[(2,6-dichlorophenyl)carbonyl]-4-(1,4-dimethyl-2-oxo-3-pyridinyl)-L-phenylalanine
Preparation of 1,4-dimethyl-2(1H)-pyridone

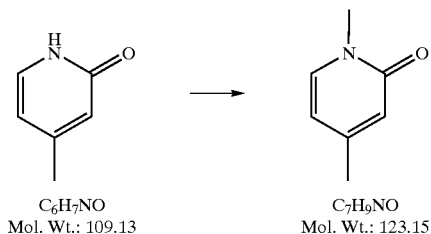

C₆H₇NO
Mol. Wt.: 109.13

C₇H₉NO
Mol. Wt.: 123.15

To a suspension of 4-methy-2(1H)-pyridone (5 g, 45.82 mmol) and potassium carbonate (12.64 g, 91.64 mmol) in DME (100 mL) was added iodomethane (50.5 g, 366 mmol) at room temperature and the reaction mixture was heated to reflux overnight. The reaction mixture was cooled to room temperature, poured into water (200 mL) and was extracted with ethyl acetate (3×100 mL). The combined extracts were washed with brine solution (200 mL) and were dried over anhydrous magnesium sulfate. Filtration of the drying agent and concentration gave the crude product which was purified by silica gel chromatography on a Biotage (40 m) column to afford 2.5 g (44% yield) of 1,4-dimethyl-2(1H)-pyridone as an amorphous white solid. FAB-HRMS m/e calcd for C₇H₉NO (M+H) 123.0241. found 123.0246.

b) Preparation of 1,4-dimethyl-3-iodo-2(1H)-pyridone and 1,4-dimethyl-5-iodo-2(1H)-pyridone

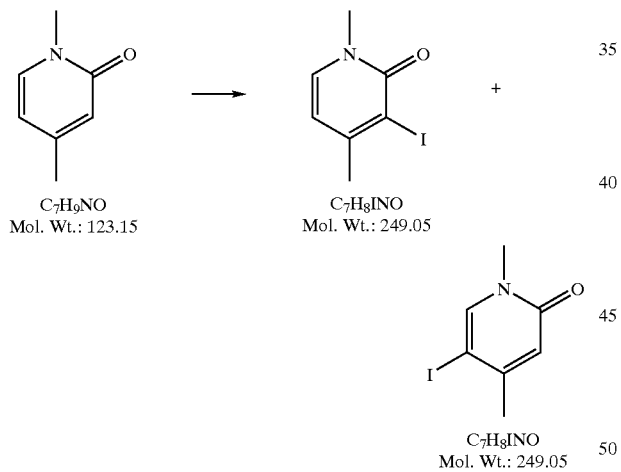

C₇H₉NO
Mol. Wt.: 123.15

C₇H₈INO
Mol. Wt.: 249.05

C₇H₈INO
Mol. Wt.: 249.05

A reaction mixture containing 1,4-dimethyl-2-pyridone (2.46 g, 20 mmol), trifluoroacetic acid (31 mL) and trifluoroacetic anhydride (6.25 mL) was refluxed for 5 min. Then, NIS (5.62 g, 25 mmol) was added and the mixture was stirred for 15 h. The reaction mixture was cooled to room temperature and the solvent was removed under vacuum. The residue was diluted with ethyl acetate (100 mL) and the white solid that formed was collected by filtration. The filtrate was washed with saturated sodium bicarbonate solution (2×100 mL), brine solution (100 mL) and was dried over anhydrous magnesium sulfate. Filtration of the drying agent and concentration of the solvent gave a crude product which was purified by silica gel chromatography on a Biotage (40 m) column to afford 0.92 g (5% yield) of a ~1:1 mixture of 1,4-dimethyl-3-iodo-2(1H)-pyridone and 1,4-dimethyl-5-iodo-2(1H)-pyridone which was used directly in the next step. ¹H NMR (300 MHz, D6-DMSO, ppm) 8.06 (s, 1H), 7.6 (d, 1H, J=5.5 Hz), 6.4 (s, 1H), 6.2 (d, 1H, J=5.5 Hz), 3.4 (s, 3H), 3.3 (s, 3H), 2.3 (s, 3H), 2.15 (s, 3H).

c) Preparation of N-[(1,1-dimethylethoxyl)carbonyl]-4-(1,4-dimethyl-2-oxo-3-pyridinyl)-L-phenylalanine methyl ester and N-[(1,1-dimethylethoxyl)carbonyl]-4-(1,4-dimethyl-2-oxo-5-pyridinyl)-L-phenylalanine methyl ester

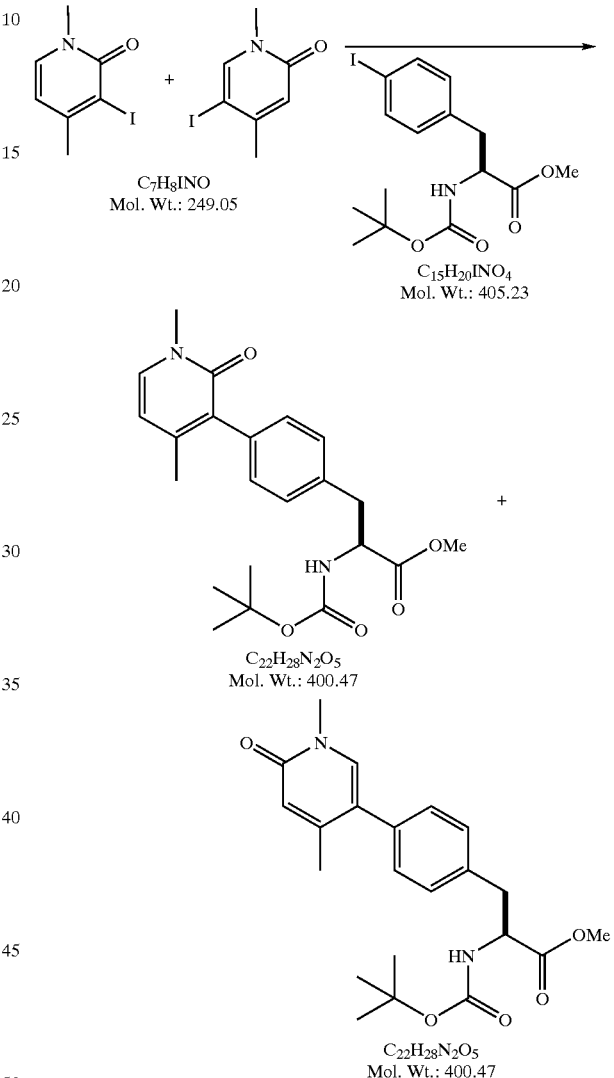

C₇H₈INO
Mol. Wt.: 249.05

C₁₅H₂₀INO₄
Mol. Wt.: 405.23

C₂₂H₂₈N₂O₅
Mol. Wt.: 400.47

C₂₂H₂₈N₂O₅
Mol. Wt.: 400.47

To a suspension of zinc dust (0.66 g, 10 mmol) in THF (1.0 mL) was added 1,2-dibromoethane (86 μL, 1 mmol)) at room temperature. This suspension was heated to 60–65° C. with a heat gun until evolution of ethylene gas ceased. Then, the suspension was cooled to room temperature and trimethylchlorosilane (0.126 mL, 1 mmol)) was added and the mixture was stirred for 15 min. A mixture of 1,4-dimethyl-3-iodo-2(1H)-pyridone and 1,4-dimethyl-5-iodo-2(1H)-pyridone (0.92 g, 3.69 mmol) in DMA (3 mL) was warmed to effect dissolution and was added in one portion to the reaction mixture. After addition, the mixture was heated to 70° C. and was stirred for 15 h, at which time the TLC analysis of an aliquot, which had been quenched with saturated ammonium chloride solution, indicated the absence of starting material. The reaction mixture was diluted with THF (4 mL) and was cooled to room temperature. The excess zinc dust was allowed to settle until a clear supernatant liquid formed (~3 h).

The above prepared solution containing the zinc compound (3.69 mmol) was added to a solution of Pd(dba)$_2$ (54 mg, 0.1 mmol), trifurylphosphine (102 mg, 0.4 mmol) and N-[(1,1-dimethylethoxy)carbonyl]-4-iodo-L-phenylalanine methyl ester (1.01 g, 2.5 mmol) in THF (4 mL) at room temperature and the light yellow mixture was stirred for 15 h at 50° C. Then, the mixture was poured into a saturated ammonium chloride solution and was extracted with ethyl acetate (3×50 mL). The combined extracts were washed with brine solution (150 mL) and were dried over anhydrous magnesium sulfate. Filtration of the drying agent and concentration gave the crude product which was purified by silica gel chromatography on a Biotage (40 m) column to obtain 0.141 g (14% yield) of N-[(1,1-dimethylethoxyl)carbonyl]-4-(1,4-dimethyl-2-oxo-3-pyridinyl)-L-phenylalanine methyl ester as an amorphous white solid. ES-HRMS m/e calcd for $C_{22}H_{28}N_2O_5$ (M+Na) 423.1890. found 423.1894 and 0.350 g (35% yield) of N-[(1,1-dimethylethoxyl)carbonyl]-4-(1,4-dimethyl-2-oxo-5-pyridinyl)-L-phenylalanine methyl ester as an amorphous white solid. ES-HRMS m/e calcd for $C_{22}H_{28}N_2O_5$ (M+Na) 423.1890. found 423.1897.

d) Preparation of 4-(1,4-dimethyl-2-oxo-3-pyridinyl)-L-phenylalanine methyl ester hydrochloride salt

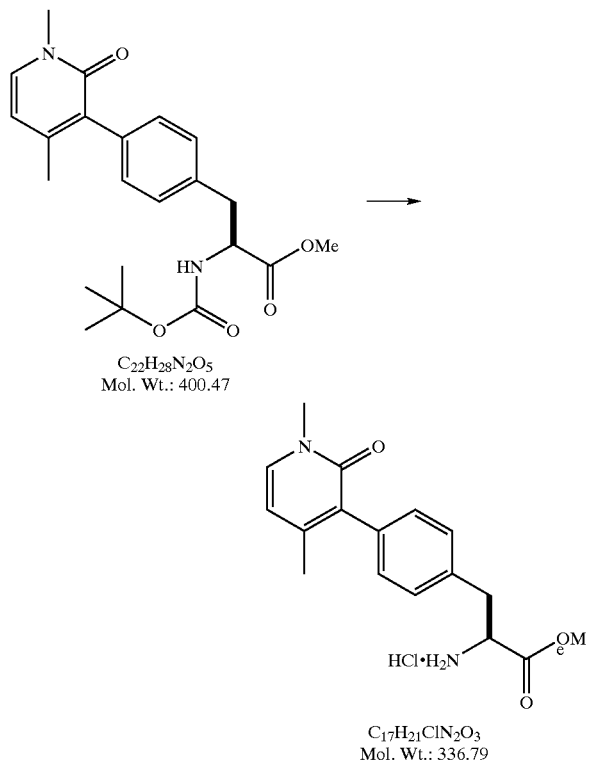

To a solution of N-[(1,1-dimethylethoxyl)carbonyl]-4-(1,4-dimethyl-2-oxo-3-pyridinyl)-L-phenylalanine methyl ester (132 mg, 0.33 mmol) in dioxane (1 mL) was added 4 N HCl solution in dioxane (1.5 mL) at room temperature. The solution was stirred for 4 h and concentrated under vacuum. The residue was dissolved in methanol (5 ml) and toluene (5 mL) and concentrated under vacuum to give 111 mg (99% yield) of 4-(1,4-dimethyl-2-oxo-3-pyridinyl)-L-phenylalanine methyl ester hydrochloride salt as an amorphous white solid. EI-HRMS m/e calcd for $C_{17}H_{20}N_2O_3$ (M$^+$) 300.1474. found 300.1486.

e) Preparation of N-[(2,6-dichlorophenyl)carbonyl]-4-(1,4-dimethyl-2-oxo-3-pyridinyl)-L-phenylalanine methyl ester

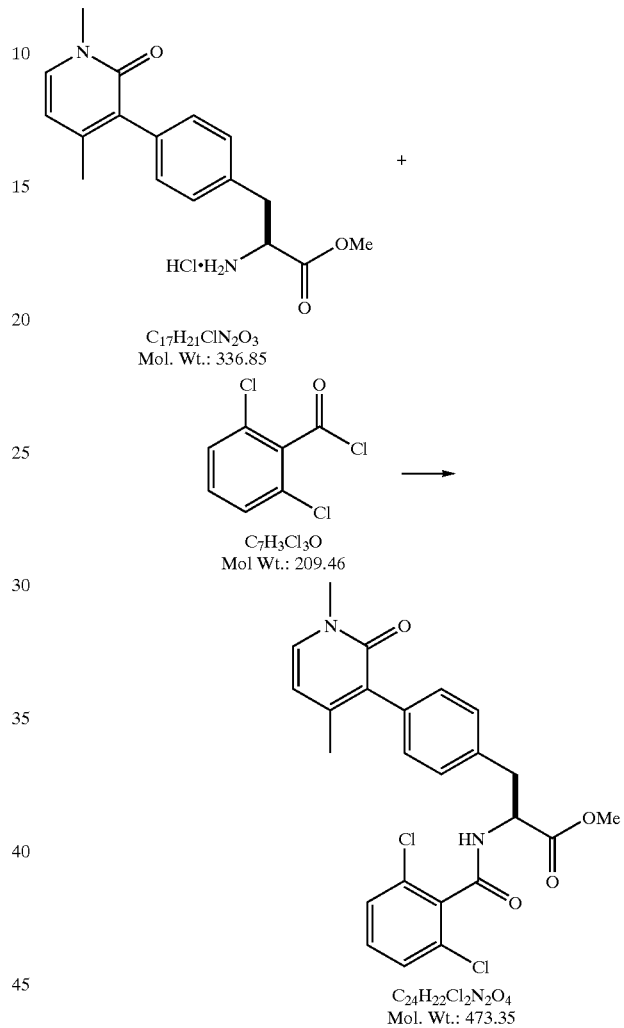

To a suspension of 4-(1,4-dimethyl-2-oxo-3-pyridinyl)-L-phenylalanine methyl ester hydrochloride salt (34 mg, 0.1 mmol) and 2,6-dichlorobenzoyl chloride (25 mg, 0.12 mmol) in dichloromethane (2 mL) was added DIEA (174 μL, 1.0 mmol) at room temperature. After 5 min, a clear solution was obtained which was stirred for 72 h. Then, the mixture was concentrated, the residue was dissolved in ethyl acetate (25 mL), was washed with 0.5 N HCl (25 mL), saturated NaHCO$_3$ solution (25 mL), brine solution (15 mL) and was dried over anhydrous magnesium sulfate. Filtration of the drying agent and concentration gave crude product, which was purified by silica gel chromatography using a Biotage (40 s) column, to afford 23 mg (49% yield) of N-[(2,6-dichlorophenyl)carbonyl]-4-(1,4-dimethyl-2-oxo-3-pyridinyl)-L-phenylalanine methyl ester as an amorphous white solid. ES-HRMS m/e calcd for $C_{24}H_{22}Cl_2N_2O_4$ (M+Na) 495.0850. found 495.0859.

f) Preparation of N-[(2,6-dichlorophenyl)carbonyl]-4-(1,4-dimethyl-2-oxo-3-pyridinyl)-L-phenylalanine

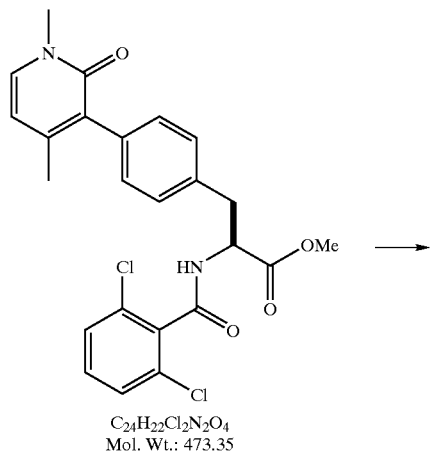

Example 32

Preparation of N-[(2-chloro-6-methylphenyl)carbonyl]-4-(1,4-dimethyl-2-oxo-3-pyridinyl)-L-phenylalanine Preparation of N-[(2-chloro-6-methylphenyl)carbonyl]-4-(1,4-dimethyl-2-oxo-3-pyridinyl)-L-phenylalanine methyl ester

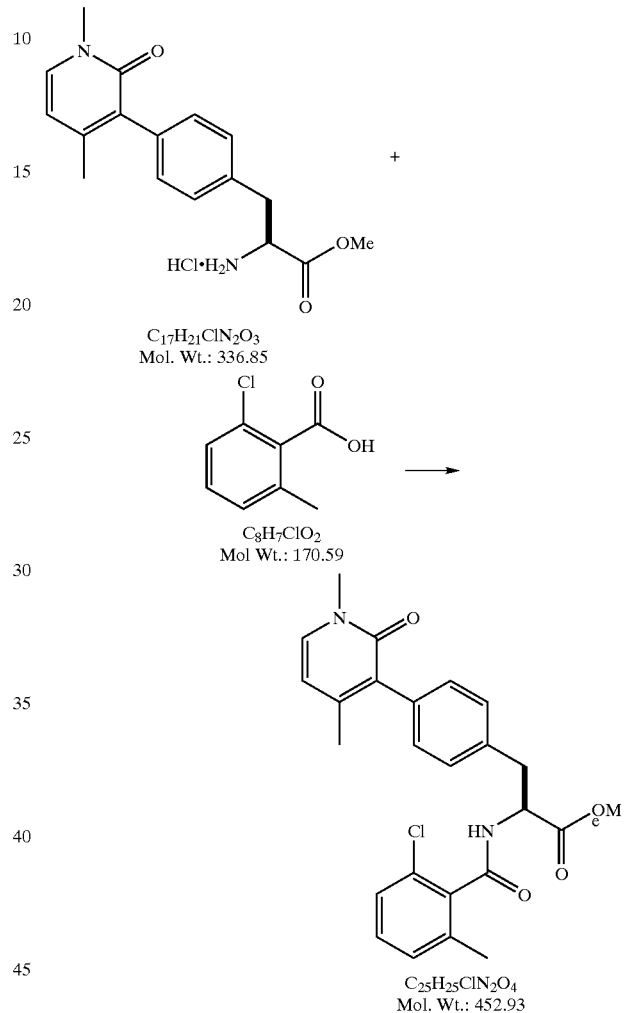

To a suspension of N-[(2,6-dichlorophenyl)carbonyl]-4-(1,4-dimethyl-2-oxo-3-pyridinyl)-L-phenylalanine methyl ester (20 mg, 0.04 mmol) in ethanol (1 mL) was added 1N aqueous sodium hydroxide solution (0.5 mL) at room temperature. The mixture was heated to 40–45° C. and stirred for 3 h. Then, the ethanol was removed under vacuum and the residue was diluted with water (10 mL). The aqueous solution was washed with diethyl ether (25 mL) to remove any neutral impurities. The aqueous layer was acidified with 1.0 N HCl and the product was extracted into ethyl acetate (2×25 mL). The combined organic extracts were washed with brine solution (50 mL) and were dried over anhydrous magnesium sulfate. Filtration of the drying agent and concentration afforded 17 mg (89% yield) of N-[(2,6-dichlorophenyl)carbonyl]-4-(1,4-dimethyl-2-oxo-3-pyridinyl)-L-phenylalanine as an amorphous white solid. ES-HRMS m/e calcd for $C_{23}H_{20}Cl_2N_2O_4$ (M+Na) 481.0691. found 481.0699.

To a suspension of 4-(1,4-dimethyl-2-oxo-3-pyridinyl)-L-phenylalanine methyl ester hydrochloride salt (68 mg, 0.2 mmol), 2-chloro-6-methylbenzoic acid (45 mg, 0.25 mmol) and HBTU (95 mg, 0.25 mmol) in DMF (1.5 mL) was added DIEA (174 µL, 1.0 mmol) at room temperature. The resulting solution was stirred for 72 h, the mixture was poured into water (25 mL) and was extracted with ethyl acetate (2×15 mL). The combined ethyl acetate extracts were washed successively with 0.5 N HCl (25 mL), saturated NaHCO$_3$ solution (25 mL), brine solution (25 mL) and were dried over anhydrous magnesium sulfate. Filtration of the drying agent and concentration of the solvent gave the crude product, which was purified by silica gel chromatography using a Biotage (40 s) column to afford 24 mg (27% yield) of N-[(2-chloro-6-methylphenyl)carbonyl]-4-(1,4-dimethyl-2-oxo-3-pyridinyl)-L-phenylalanine methyl ester as an amorphous white solid. ES-HRMS m/e calcd for $C_{25}H_{25}ClN_2O_4$ (M+Na) 475.1395. found 475.1400.

b) Preparation of N-[(2-chloro-6-methylphenyl)carbonyl]-4-(1,4-dimethyl-2-oxo-3-pyridinyl)-L-phenylalanine

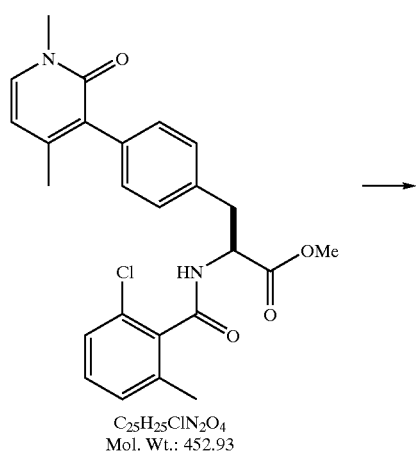

C₂₅H₂₅ClN₂O₄
Mol. Wt.: 452.93

↓

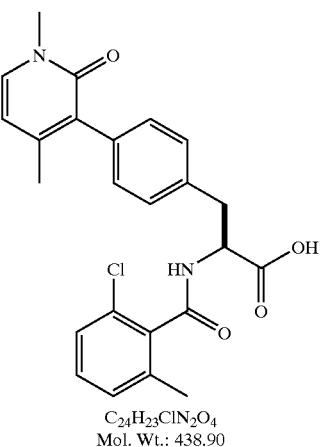

C₂₄H₂₃ClN₂O₄
Mol. Wt.: 438.90

To a suspension of N-[(2-chloro-6-methylphenyl)carbonyl]-4-(1,4-dimethyl-2-oxo-3-pyridinyl)-L-phenylalanine methyl ester (22 mg, 0.048 mmol) in ethanol (1 mL) was added 1N aqueous sodium hydroxide solution (0.5 mL) at room temperature. The resulting solution was heated to 40–45° C. and stirred for 2 h. Then, the ethanol was removed under vacuum and the residue was diluted with water (25 mL). The aqueous solution was washed with diethyl ether (25 mL) to remove any neutral impurities. The aqueous layer was acidified with 1.0 N HCl and the product was extracted into ethyl acetate (2×25 mL). The combined extracts were washed with brine solution (50 mL) and were dried over anhydrous magnesium sulfate. Filtration of the drying agent and concentration afforded 18 mg (86% yield) of N-[(2-chloro-6-methylphenyl)carbonyl]-4-(1,4-dimethyl-2-oxo-3-pyridinyl)-L-phenylalanine as an amorphous white solid. ES-HRMS m/e calcd for $C_{24}H_{23}ClN_2O_4$ (M+H) 439.1419. found 439.1425.

Example 33

Preparation of N-[(2,6-dichlorophenyl)carbonyl]-4-[1,6-dimethyl-4-(trifluoromethyl)-2-oxo-3-pyridinyl]-L-phenylalanine Preparation of 1,6-dimethyl-4-(trifluoromethyl)-2-pyridone

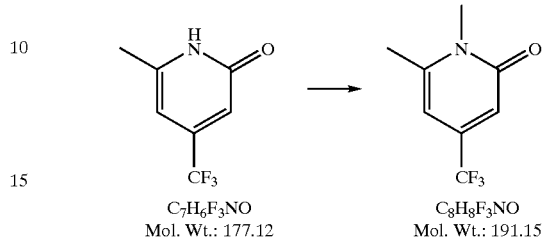

C₇H₆F₃NO
Mol. Wt.: 177.12

C₈H₈F₃NO
Mol. Wt.: 191.15

To a suspension of 6-methyl-4-(trifluoromethyl)-1H-2-pyridone (2 g, 11.25 mmol) and potassium carbonate (4.68 g, 33.9 mmol) in DME (25 mL) was added iodomethane (9.62 g, 67.8 mmol) at room temperature and the reaction mixture was heated to reflux overnight. The reaction mixture was cooled to room temperature, poured into water (100 mL) and extracted with ethyl acetate (3×100 mL). The combined extracts were washed with brine solution (200 mL) and were dried over anhydrous magnesium sulfate. Filtration of the drying agent and concentration of the solvent gave the crude product which was purified by silica gel chromatography on a Biotage (40 m) column to obtain 2.1 g (97% yield) of 1,6-dimethyl-4-(trifluoromethyl)-2-pyridone as a white solid: mp 80–82° C. EI-HRMS m/e calcd for $C_8H_8F_3NO$ (M⁺) 191.0558. found 191.0559.

b) Preparation of 1,6-dimethyl-3-iodo-4-(trifluoromethyl)-2-pyridone

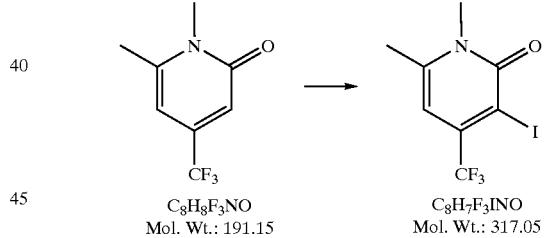

C₈H₈F₃NO
Mol. Wt.: 191.15

C₈H₇F₃INO
Mol. Wt.: 317.05

A mixture containing 1,6-dimethyl-4-(trifluoromethyl)-2-pyridone (2.1 g, 10.98 mmol), trifluoroacetic acid (18 mL) and trifluoroacetic anhydride (3.5 mL) was refluxed for 5 min. Then, NIS (3.15 g, 14 mmol) was added and the reaction mixture was stirred for 15 h. The reaction mixture was cooled to room temperature and the solvent was removed under vacuum. The residue was diluted with ethyl acetate (100 mL), was washed with saturated sodium bicarbonate solution (2×100 mL) and brine solution (100 mL) and was dried over anhydrous magnesium sulfate. Filtration of the drying agent and concentration gave a crude product, which was purified by silica gel chromatography on a Biotage (40 m) column to afford 2.15 g (62% yield) of 1,6-dimethyl-3-iodo-4-(trifluoromethyl)-2-pyridone as an amorphous white solid. EL-HRMS m/e calcd for $C_8H_7F_3INO$ (M⁺) 316.9524. found 316.9527.

c) Preparation of N-[(1,1-dimethylethoxyl)carbonyl]-4-[1,6-dimethyl-4-(trifluoromethyl)-2-oxo-3-pyridinyl]-L-phenylalanine methyl ester

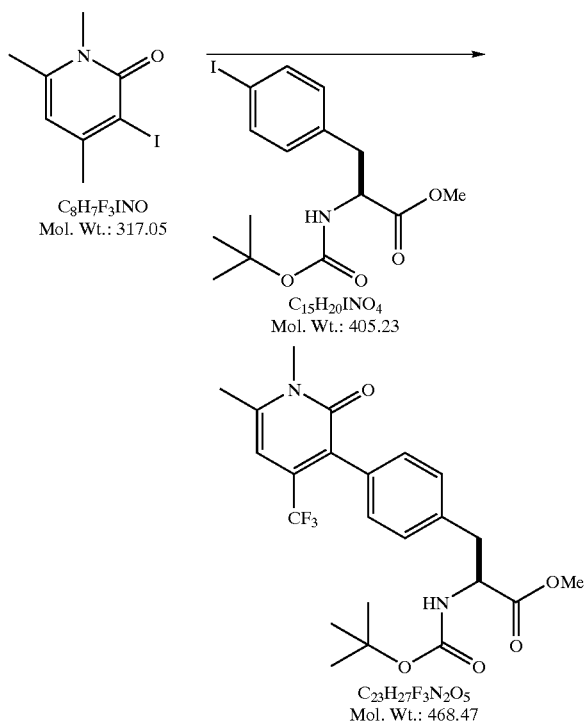

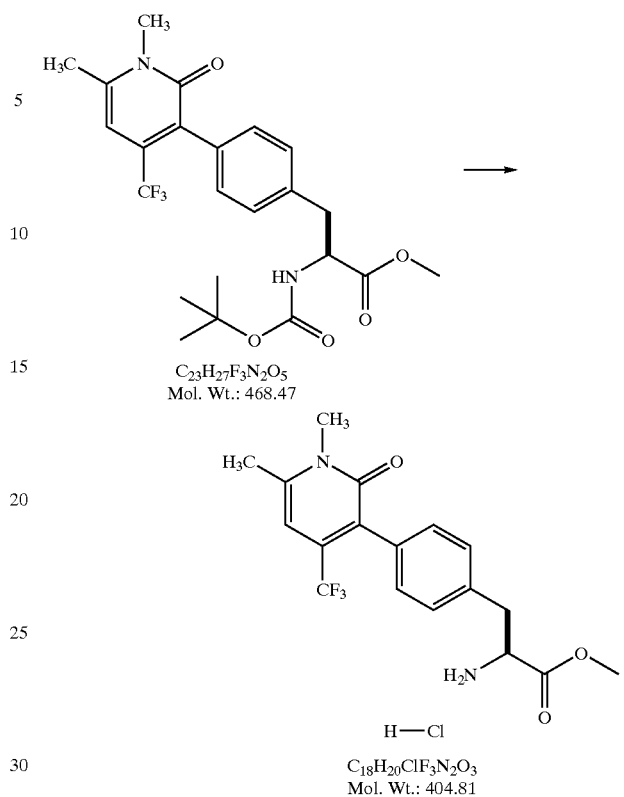

To a suspension of zinc dust (1.96 g, 30 mmol) in THF (2.0 mL) was added 1,2-dibromoethane (172 μL, 2 mmol)) at room temperature. This suspension was heated to 60–65° C. with a heat gun until evolution of ethylene gas ceased. Then, the suspension was cooled to room temperature and trimethylchlorosilane (127 μL, 1 mmol)) was added and the mixture was stirred for 15 min. A suspension of 1,6-dimethyl-3-iodo-4-(trifluoromethyl)-2-pyridone (2.15 g, 6.78 mmol) in DMA (6 mL) was warmed with a heat gun to effect dissolution and was added in one portion to the reaction mixture. After addition, the mixture was heated to 70° C. and was stirred for 15 h, at which time the TLC analysis of an aliquot, which had been quenched with saturated ammonium chloride solution, indicated the absence of starting material. The reaction mixture was diluted with THF (6 mL), was cooled to room temperature and the excess zinc dust was allowed to settle.

The above prepared solution containing the zinc compound (6.78 mmol) was added to a solution of Pd(dba)$_2$ (108 mg, 0.2 mmol), trifurylphosphine (204 mg, 0.8 mmol) and N-[(1,1-dimethylethoxy)carbonyl]-4-iodo-L-phenylalanine methyl ester (1.62 g, 4 mmol) in THF (8 mL) at room temperature and the light yellow mixture was stirred for 15 h at 50° C. The reaction mixture was poured into a saturated ammonium chloride solution and was extracted with ethyl acetate (3×70 mL). The combined extracts were washed with brine solution (150 mL) and were dried over anhydrous magnesium sulfate. Filtration of the drying agent and concentration gave the crude product, which was purified by silica gel chromatography on a Biotage (40 m) column to obtain 0.711 g (38% yield) of N-[(1,1-dimethylethoxy) carbonyl]-4-[1,6-dimethyl-4-(trifluoromethyl)-2-oxo-3-pyridinyl]-L-phenylalanine methyl ester as an amorphous white solid. ES-HRMS m/e calcd for $C_{23}H_{27}F_3N_2O_5$ (M+Na) 491.1764. found 491.1770.

d) Preparation of 4-[1,6-dimethyl-4-(trifluoromethyl)-2-oxo-3-pyridinyl]-L-phenylalanine methyl ester hydrochloride salt To a solution of N-[(1,1-dimethylethoxyl)carbonyl]-4-[1,6-dimethyl-4-(trifluoromethyl)-2-oxo-3-pyridinyl]-L-phenylalanine methyl ester (132 mg, 0.33 mmol) in dioxane (3 mL) was added 4 N HCl solution in dioxane (4.5 mL) at room temperature. The solution was stirred for 4 h as a white solid was formed. The mixture was diluted with diethyl ether (50 mL) and solid was collected by filtration washing with diethyl ether. After drying under high vacuum, 315 mg (92% yield) of 4-[1,6-dimethyl-4-(trifluoromethyl)-2-oxo-3-pyridinyl]-L-phenylalanine methyl ester hydrochloride salt was obtained as an amorphous white solid. ES-HRMS m/e calcd for $C_{18}H_{19}F_3N_2O_3$ (M+Na) 391.1241. found 391.1241.

e) Preparation of N-[(2,6-dichlorophenyl)carbonyl]-4-[1,6-dimethyl-4-(trifluoromethyl)-2-oxo-3-pyridinyl]-L-phenylalanine methyl ester

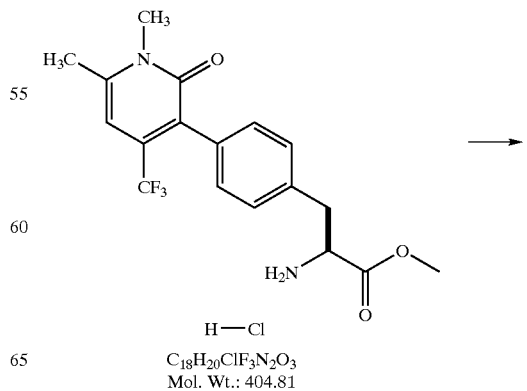

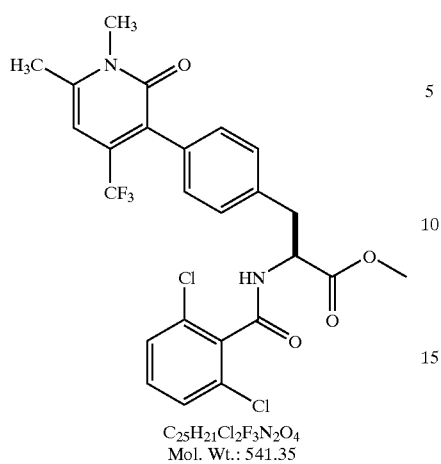

C25H21Cl2F3N2O4
Mol. Wt.: 541.35

To a suspension of 4-[1,6-dimethyl-4-(trifluoromethyl)-2-oxo-3-pyridinyl]-L-phenylalanine methyl ester hydrochloride salt (150 mg, 0.37 mmol) and 2,6-dichlorobenzoyl chloride (85 mg, 0.4 mmol) in dichloromethane (6 mL) was added DIEA (257 µL, 1.48 mmol) at room temperature. After 5 min, a clear solution was obtained which was stirred for 48 h. Then, the mixture was concentrated and the residue was dissolved in ethyl acetate (50 mL). The ethyl acetate solution was washed with 0.5 N HCl (50 mL), saturated NaHCO3 solution (50 mL) and brine solution (50 mL) and was dried over anhydrous magnesium sulfate. Filtration of the drying agent and concentration gave crude product, which was purified by silica gel chromatography on a Biotage (40 m) column to give 190 mg (95% yield) of N-[(2,6-dichlorophenyl)carbonyl]-4-[1,6-dimethyl-4-(trifluoromethyl)-2-oxo-3-pyridinyl]-L-phenylalanine methyl ester as an amorphous white solid. ES-HRMS m/e calcd for $C_{25}H_{21}Cl_2F_3N_2O_4$ (M+Na) 563.0724. found 563.0726.

f) Preparation of N-[(2,6-dichlorophenyl)carbonyl]-4-[1,6-dimethyl-4-(trifluoromethyl)-2-oxo-3-pyridinyl]-L-phenylalanine

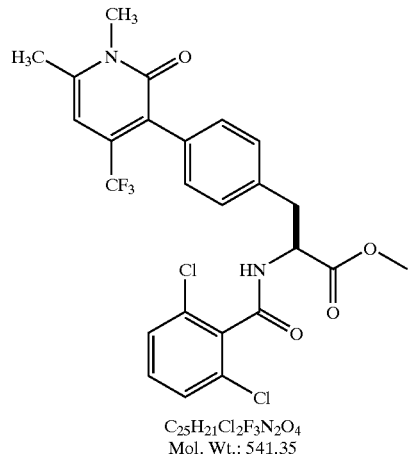

C25H21Cl2F3N2O4
Mol. Wt.: 541.35

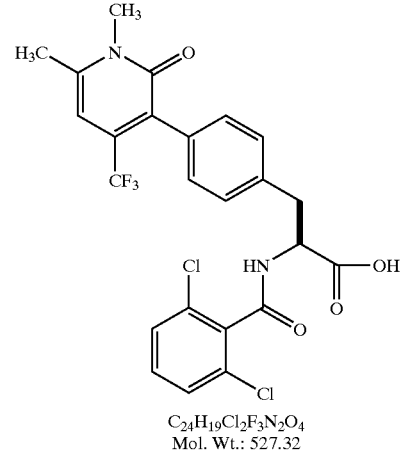

C24H19Cl2F3N2O4
Mol. Wt.: 527.32

To a suspension of N-[(2,6-dichlorophenyl)carbonyl]-4-[1,6-dimethyl-4-(trifluoromethyl)-2-oxo-3-pyridinyl]-L-phenylalanine methyl ester (177 mg, 0.326 mmol) in ethanol (6 mL) was added 1N aqueous sodium hydroxide solution (4 mL) at room temperature. The mixture was stirred for 5 h. Then, the ethanol was removed under vacuum and the residue was diluted with water (20 mL). The aqueous solution was washed with diethyl ether (50 mL) to remove any neutral impurities. The aqueous layer was acidified with 1.0 N HCl and the product was extracted with ethyl acetate (2×50 mL). The combined organic extracts were washed with brine solution (50 mL) and were dried over anhydrous magnesium sulfate. Filtration of the drying agent and concentration afforded 159 mg (92% yield) of N-[(2,6-dichlorophenyl)carbonyl]-4-[1,6-dimethyl-4-(trifluoromethyl)-2-oxo-3-pyridinyl]-L-phenylalanine as a white solid: mp 238–240° C. ES-HRMS m/e calcd for $C_{24}H_{19}Cl_2F_3N_2O_4$ (M+Na) 549.0567. found 549.0570.

Example 34

Preparation of N-[(2-ethyl-6-methylphenyl)carbonyl]-4-[1,6-dimethyl-4-(trifluoromethyl)-2-oxo-3-pyridinyl]-L-phenylalanine a. Preparation of 2-ethyl-6-methylbenzoic acid.

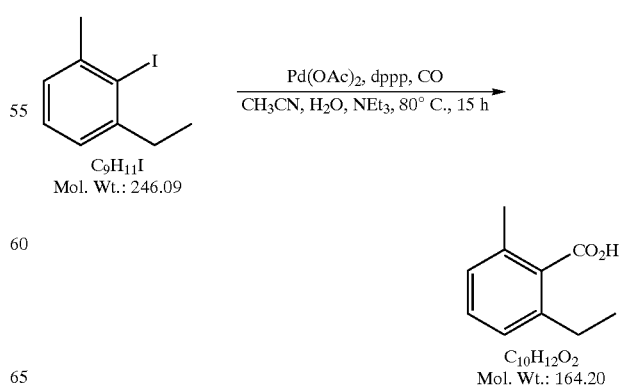

A 250 mL pressure bottle was charged with 2-ethyl-6-methyliodobenzene (30.07 mmol, 7.4 g), Pd(OAc)$_2$ (1.43 mmol, 334 mg) and dppp (1.43 mmol, 620 mg). The flask was closed with a septum and evacuated three times with argon. Then, acetonitrile (96 mL), triethylamine (189 mmol, 19.0 g, 26.25 mL) and water (19.1 mL) were added successively by the aid of syringe and the rubber septum was replaced with teflon lined cap connected to a carbon monoxide source. The flask was now pressurized with carbon monoxide (40 psi) and the excess pressure was released. This process was repeated three times and finally the mixture was stirred for 5 min under 40 psi carbon monoxide pressure. The flask was then disconnected from the carbon monoxide cylinder and immersed in a preheated oil bath (83–85° C.). The reaction mixture turned black over 1 hr and was stirred for another 14 hr at this temperature. Then, the reaction mixture was cooled to room temperature and the pressure was released. The resulting mixture was diluted with ether (200 mL) and 1.0N NaOH (20 mL). The formed acid was extracted into water (2×100 mL). The combined water extracts were neutralized with 1.0N HCl and the acid was extracted into dichloromethane (3×100 mL). The combined dichloromethane extracts were washed with brine solution and dried over MgSO$_4$. Filtration of the drying agent and removal of solvent under vacuum gave 3.58 g (72.5%) of a viscous brown oil which slowly solidfied overnight. HR MS: Obs. mass, 164.0833. Calcd. mass, 164.0837 (M+).

b. Preparation of 2-ethyl-6-methylbenzoyl chloride

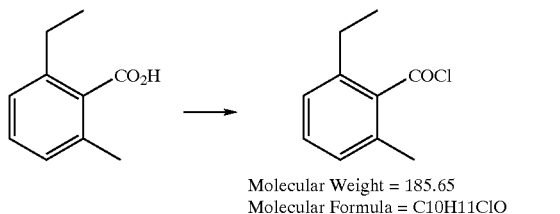

Molecular Weight = 185.65
Molecular Formula = C10H11ClO

A solution of 2-ethyl-6-methylbenzoic acid (49 mg, 0.30 mmol) in dichloromethane (3 mL) containing DMF (1 drop) was treated with oxalyl chloride (0.14 mL, 1.6 mmol) and the mixture was stirred for 15 h. The mixture was concentrated, azeotroping with toluene to remove traces of oxalyl chloride and the residue was used directly in the next step.

c. Preparation of N-[(2-ethyl-6-methylphenyl)carbonyl]-4-[1,6-dimethyl-4-(trifluoromethyl)-2-oxo-3-pyridinyl]-L-phenylalanine methyl ester

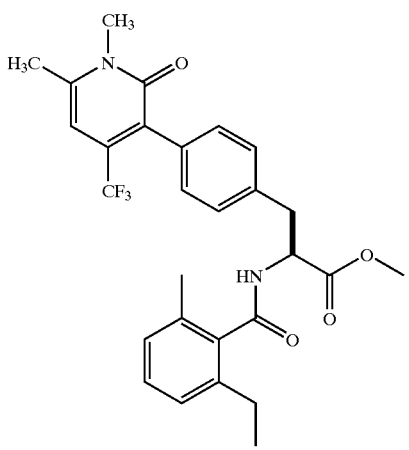

Molecular Weight = 514.54
Molecular Formula = C28H29F3N2O4

A mixture of the above prepared acid chloride, 4-[1,6-dimethyl-4-(trifluoromethyl)-2-oxo-3-pyridinyl]-phenylalanine methyl ester hydrochloride (100 mg, 0.25 mmol) in dichloromethane (5 mL) was treated with DIPEA (0.17 mL, 1.0 mmol) and the resulting light brown solution was stirred for 3 days. The mixture was concentrated, diluted with ethyl acetate, washed with 1 N HCl and brine solution and was dried over magnesium sulfate. Filtration and evaporation afforded a residue, which was purified by silica gel chromatography using a Biotage column (40 s) to give N-[(2-ethyl-6-methylphenyl)carbonyl]-4-[1,6-dimethyl-4-(trifluoromethyl)-2-oxo-3-pyridinyl]-L-phenylalanine methyl ester as a white foam (79 mg, 62%). ES-HRMS m/e calcd for C$_{28}$H$_{29}$F$_3$NO$_4$ (M+Na) 537.1974. found 537.1972.

d. Preparation of N-[(2-ethyl-6-methylphenyl)carbonyl]-4-[1,6-dimethyl-4-(trifluoromethyl)-2-oxo-3-pyridinyl]-L-phenylalanine

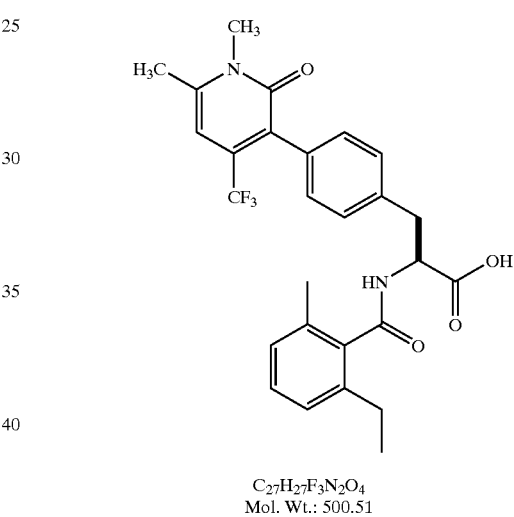

C$_{27}$H$_{27}$F$_3$N$_2$O$_4$
Mol. Wt.: 500.51

A solution of N-[(2-ethyl-6-methylphenyl)carbonyl]-4-[1,6-dimethyl-4-(trifluoromethyl)-2-oxo-3-pyridinyl]-L-phenylalanine methyl ester (74 mg, 0.14 mmol), and 1 N sodium hydroxide (2 mL, 2 mmol) in ethanol (3 mL) was heated to 40–45 C for 3 h. Then, the ethanol was removed under vacuum and the residue was diluted with water. The aqueous solution was washed with diethyl ether to remove any neutral impurities. The aqueous layer was acidified with 1.0 N HCl and the product was extracted with ethyl acetate. The combined organic extracts were washed with brine solution and were dried over anhydrous magnesium sulfate. Filtration of the drying agent and concentration afforded 68 mg (95% yield) of N-[(2-ethyl-6-methylphenyl)carbonyl]-4-[1,6-dimethyl-4-(trifluoromethyl)-2-oxo-3-pyridinyl]-L-phenylalanine (mp 219–221° C.). ES-HRMS m/e calcd for C$_{27}$H$_{27}$F$_3$N$_2$O$_4$ (M+Na) 523.1815. found 523.1816.

Example 35

Preparation of N-[(2-(1-methylethyl)-6-methylphenyl)carbonyl]-4-[1,6-dimethyl-4-(trifluoromethyl)-2-oxo-3-pyridinyl]-L-phenylalanine a. Preparation of 2-(1-methylethyl)-6-methyliodobenzene

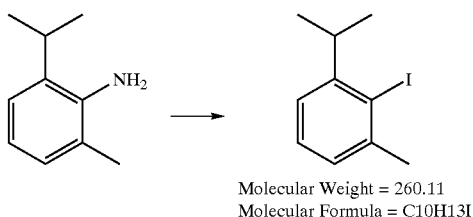

Molecular Weight = 260.11
Molecular Formula = C10H13I

To a suspension of 2-(1-methylethyl)-6-methylaniline (15.57 mmol, 14.9 g), in conc. HCl (50 mL) and 30 g of ice, was added dropwise a solution of NaNO$_2$ (110 mmol, 8 g) in H$_2$O (35 mL) at −5° C. to 5° C. for 30 min. After addition, the red colored solution was stirred for another 30 min. Then, a solution of KI (200 mmol, 33.2 g) in H$_2$O (50 mL) was added dropwise over 20 min at 0–5° C. After the addition, the mixture was allowed to warm to room temperature during which time, an exothermic reaction with gas evolution occurred. The resulting red colored solution was stirred for 18 h. Then, the mixture was extracted with ethyl acetate (3×100 mL). The combined extracts were washed with sodium thiosulfate solution (200 mL), brine solution and dried over MgSO$_4$. Filtration of the drying agent and concentration of the solvent under vacuum gave a colored compound which was purified by a silica gel column chromatography to obtain pure 2-(1-methylethyl)-6-methyliodobenzene (17.8 g, 68%) as a yellow oil. HR MS: Obs. mass, 260.0063. Calcd. mass, 260.0062 (M+).

b. Preparation of 2-(1-methylethyl)-6-methylbenzoic acid.

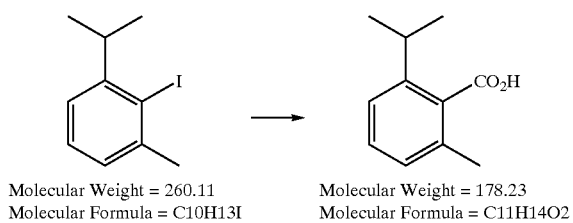

Molecular Weight = 260.11         Molecular Weight = 178.23
Molecular Formula = C10H13I       Molecular Formula = C11H14O2

A 250 mL pressure bottle was charged with 2-(1-methylethyl)-6-methyliodobenzene (25.2 mmol, 6.55 g), Pd(OAc)$_2$ (1.2 mmol, 280 mg) and dppp (1.2 mmol, 520 mg). The flask was closed with a septum and evacuated three times with argon. Then, acetonitrile (96 mL), triethylamine (188.7 mmol, 19.0 g, 26.25 mL) and water (19.1 mL) were added successively by the aid of syringe. Then, the rubber septum was replaced with teflon lined cap connected to a carbon monoxide source. The flask was now pressurized with carbon monoxide (40 psi) and the excess pressure was released. This process was repeated three times and finally the mixture was stirred for 5 min under 40 psi carbon monoxide pressure. The flask was then disconnected from the carbon monoxide cylinder and immersed in a preheated oil bath (83–85° C.). The reaction mixture turned black in 1 hr and was stirred for another 4 hr at this temperature. Then, the reaction mixture was cooled to room temperature, the pressure was released and the mixture was diluted with ether (200 mL) and 1.0N NaOH (10 mL). The acid was extracted into water (2×100 mL). The combined aqueous extracts were neutralized with 1.0N HCl and the acid was extracted into ethyl acetate (2×100 mL). The combined organic extracts were washed with brine solution and dried over MgSO$_4$. Filtration of the drying agent and concentration gave 2.8 g (62%) of a viscous yellow oil. HR MS: Obs. mass, 178.0996. Calcd. mass, 178.0994 (M+).

c. Preparation of 2-(1-methylethyl)-6-methylbenzoyl chloride

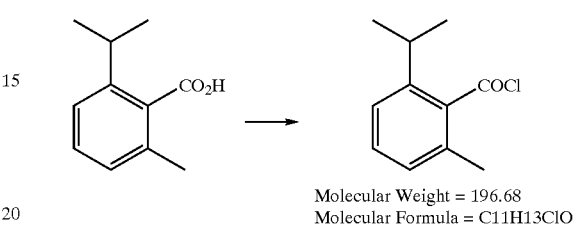

Molecular Weight = 196.68
Molecular Formula = C11H13ClO

A solution of 2-(1-methylethyl)-6-methylbenzoic acid (64 mg, 0.35 mmol) in dichloromethane (3 mL) containing DMF (2 drops) was treated with oxalyl chloride (0.16 mL, 1.8 mmol) and the mixture was stirred for 15 h. The mixture was concentrated, azeotroping with toluene to remove traces of oxalyl chloride and the residue was used directly in the next step.

d. Preparation of N-[[2-(1-methylethyl)-6-methylphenyl]carbonyl]-4-[1,6-dimethyl-4-(trifluoromethyl)-2-oxo-3-pyridinyl]-L-phenylalanine

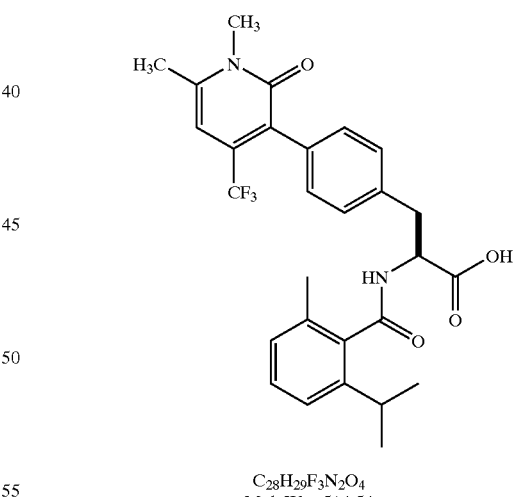

C28H29F3N2O4
Mol. Wt.: 514.54

N-[[2-(1-methylethyl)-6-methylphenyl]carbonyl]-4-[1,6-dimethyl-4-(trifluoromethyl)-2-oxo-3-pyridinyl]-L-phenylalanine was prepared from 4-[1,6-dimethyl-4-(trifluoromethyl)-2-oxo-3-pyridinyl]-L-phenylalanine methyl ester and 2-(1-methylethyl)-6-methylbenzoyl chloride using the general procedures described in example 33. ES-HRMS m/e calcd for C$_{28}$H$_{29}$F$_3$N$_2$O$_4$ (M+Na) 537.1972. found 537.1977.

Example 36

Preparation of N-[(2-chloro-6-methylphenyl)carbonyl]-4-[1,6-dimethyl-4-(trifluoromethyl)-2-oxo-3-pyridinyl]-L-phenylalanine Preparation of N-[(2-chloro-6-methylphenyl)carbonyl]-4-[1,6-dimethyl-4-(trifluoromethyl)-2-oxo-3-pyridinyl]-L-phenylalanine methyl ester

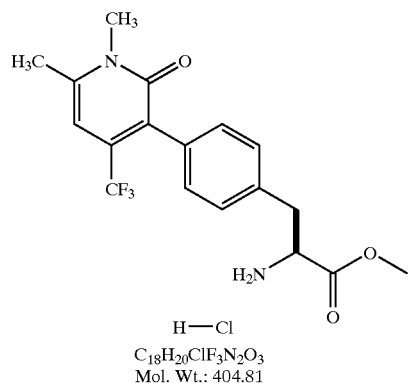

C$_{18}$H$_{20}$ClF$_3$N$_2$O$_3$
Mol. Wt.: 404.81

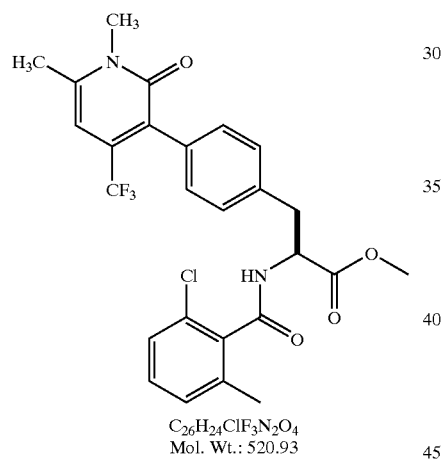

C$_{26}$H$_{24}$ClF$_3$N$_2$O$_4$
Mol. Wt.: 520.93

To a suspension of 4-[1,6-dimethyl-4-(trifluoromethyl)-2-oxo-3-pyridinyl]-L-phenylalanine methyl ester hydrochloride salt (100 mg, 0.25 mmol), 2-chloro-6-methylbenzoic acid (60 mg, 0.35 mmol) and HBTU (132 mg, 0.35 mmol) in DMF (2 mL) was added DIEA (174 µL, 1.0 mmol) at room temperature. The resulting mixture was stirred for 72 h. Then, the mixture was poured into water (25 mL) and was extracted with ethyl acetate (2×15 mL). The combined ethyl acetate extracts were washed successively with 0.5 N HCl (25 mL), saturated NaHCO$_3$ solution (25 mL), brine solution (25 mL) and were dried over anhydrous magnesium sulfate. Filtration of the drying agent and concentration gave the crude product which was purified by silica gel chromatography using a Biotage (40 s) column to afford 98 mg (75% yield) of N-[(2-chloro-6-methylphenyl)carbonyl]-4-[1,6-dimethyl-4-(trifluoromethyl)-2-oxo-3-pyridinyl]-L-phenylalanine methyl ester as an amorphous white solid. ES-HRMS m/e calcd for C$_{26}$H$_{24}$ClF$_3$N$_2$O$_4$ (M+Na) 543.1268. found 543.1275.

b) Preparation of N-[(2-chloro-6-methylphenyl)carbonyl]-4-[1,6-dimethyl-4-(trifluoromethyl)-2-oxo-3-pyridinyl]-L-phenylalanine

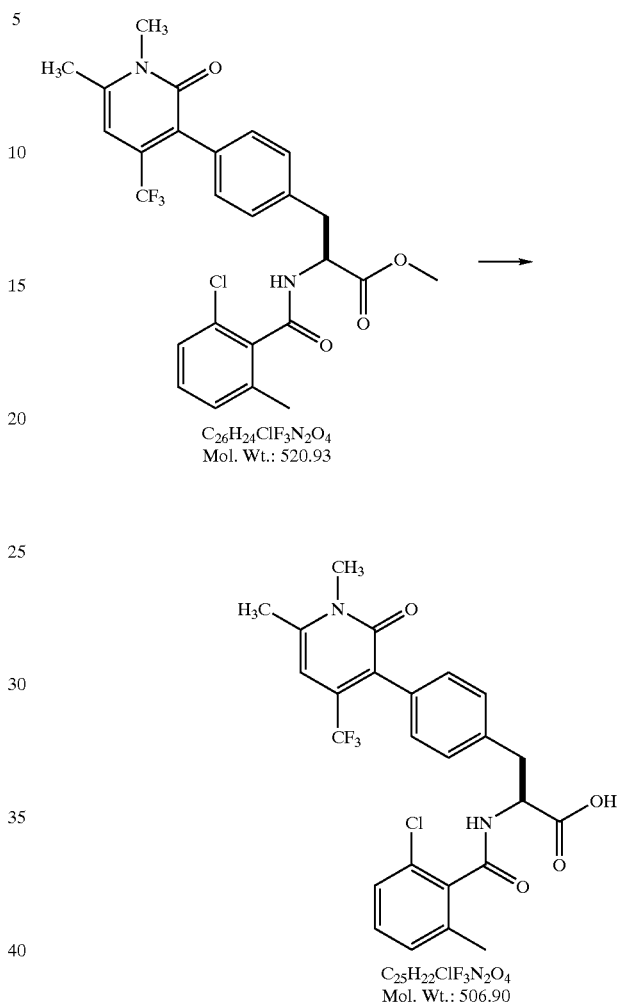

C$_{26}$H$_{24}$ClF$_3$N$_2$O$_4$
Mol. Wt.: 520.93

C$_{25}$H$_{22}$ClF$_3$N$_2$O$_4$
Mol. Wt.: 506.90

To a suspension of N-[(2-chloro-6-methylphenyl)carbonyl]-4-[1,6-dimethyl-4-(trifluoromethyl)-2-oxo-3-pyridinyl]-L-phenylalanine methyl ester (91 mg, 0.174 mmol) in ethanol (5 mL) was added 1N aqueous sodium hydroxide solution (4 mL) at room temperature. The resulting solution was heated to 40–45° C. and stirred for 4 h. Then, the ethanol was removed under vacuum and the residue was diluted with water (25 mL). The aqueous solution was washed with diethyl ether (25 mL) to remove any neutral impurities. The aqueous layer was acidified with 1.0 N HCl and was extracted with ethyl acetate (2×25 mL). The combined organic extracts were washed with brine solution (50 mL) and were dried over anhydrous magnesium sulfate. Filtration of the drying agent and concentration of the filtrate afforded 71 mg (80% yield) of N-[(2-chloro-6-methylphenyl)carbonyl]-4-[1,6-dimethyl-4-(trifluoromethyl)-2-oxo-3-pyridinyl]-L-phenylalanine as a white solid: mp 220–223° C. ES-HRMS m/e calcd for C$_{25}$H$_{22}$ClF$_3$N$_2$O$_4$ (M+Na) 529.1111. found 529.1119.

Example 37

Preparation of N-[[1-(2-methoxyethyl)cyclopentyl]carbonyl]-4-[1,6-dimethyl-4-(trifluoromethyl)-2-oxo-3-pyridinyl]-L-phenylalanine

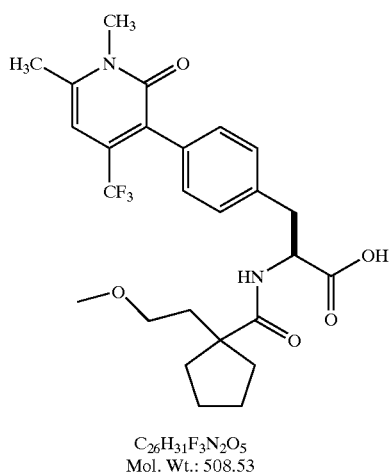

C$_{26}$H$_{31}$F$_3$N$_2$O$_5$
Mol. Wt.: 508.53

N-[[1-(2-methoxyethyl)cyclopentyl]carbonyl]-4-[1,6-dimethyl-4-(trifluoromethyl)-2-oxo-3-pyridinyl]-L-phenylalanine (mp 181–183° C.) was prepared from 4-[1,6-dimethyl-4-(trifluoromethyl)-2-oxo-3-pyridinyl]-L-phenylalanine methyl ester and 1-(2-methoxyethyl)cyclopentane carboxylic acid (obtained as described in WO 9910313) using the general procedures described in example 36. ES-HRMS m/e calcd for C$_{26}$H$_{31}$F$_3$N$_2$O$_5$ (M+Na) 531.2077. found 531.2084.

Example 38

Preparation of N-[(2,6-dichlorophenyl)carbonyl]-4-[1,6-dimethyl-4-(trifluoromethyl)-2-oxo-3-pyridinyl]-L-phenylalanine ethyl ester

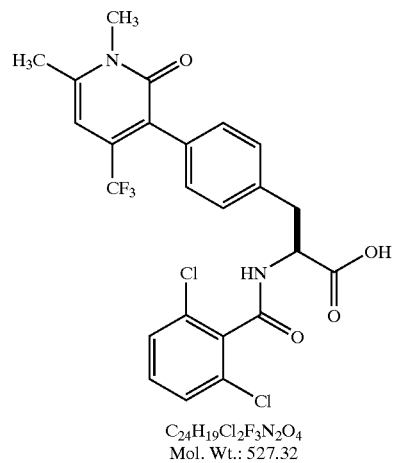

C$_{24}$H$_{19}$Cl$_2$F$_3$N$_2$O$_4$
Mol. Wt.: 527.32

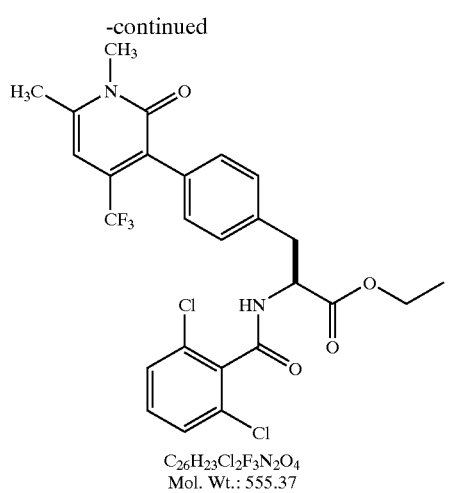

C$_{26}$H$_{23}$Cl$_2$F$_3$N$_2$O$_4$
Mol. Wt.: 555.37

To a suspension of N-[(2,6-dichlorophenyl)carbonyl]-4-[1,6-dimethyl-4-(trifluoromethyl)-2-oxo-3-pyridinyl]-L-phenylalanine (145 mg, 0.275 mmol) and sodium bicarbonate (185 mg, 2.2 mmol) in DMF (2 mL) was added iodoethane (343 mg, 2.2 mmol) at room temperature. The mixture was stirred for 72 h at room temperature. Then, the reaction mixture was poured into water (30 mL) and was extracted with ethyl acetate (3×20 mL). The combined organic extracts were washed with brine solution (60 mL) and were dried over anhydrous magnesium sulfate. Filtration of the drying agent and concentration of the filtrate gave 129 mg (85% yield) of N-[(2,6-dichlorophenyl)carbonyl]-4-[1,6-dimethyl-4-(trifluoromethyl)-2-oxo-3-pyridinyl]-L-phenylalanine ethyl ester as a crystalline white solid: mp 86–91° C. ES-HRMS m/e calcd for C$_{26}$H$_{23}$Cl$_2$F$_3$N$_2$O$_4$ (M+Na) 577.0876. found 577.0887.

Example 39

Preparation of N-[(2,6-dichlorophenyl)carbonyl]-4-[1,6-dimethyl-4-(trifluoromethyl)-2-oxo-3-pyridinyl]-L-phenylalanine 2-[(N,N-diethyl)amino]ethyl ester

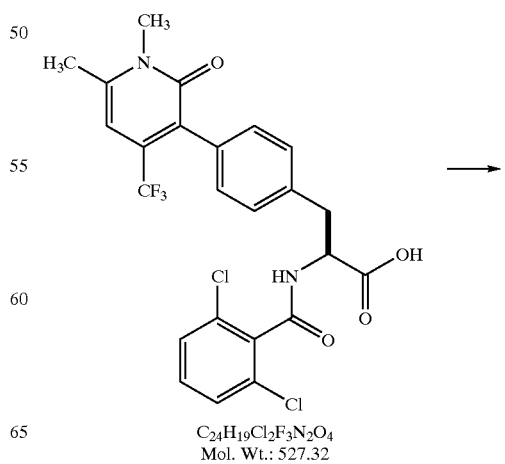

C$_{24}$H$_{19}$Cl$_2$F$_3$N$_2$O$_4$
Mol. Wt.: 527.32

-continued

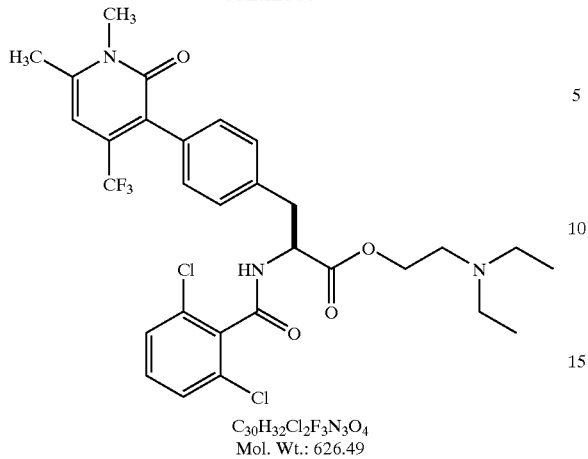

C30H32Cl2F3N3O4
Mol. Wt.: 626.49

-continued

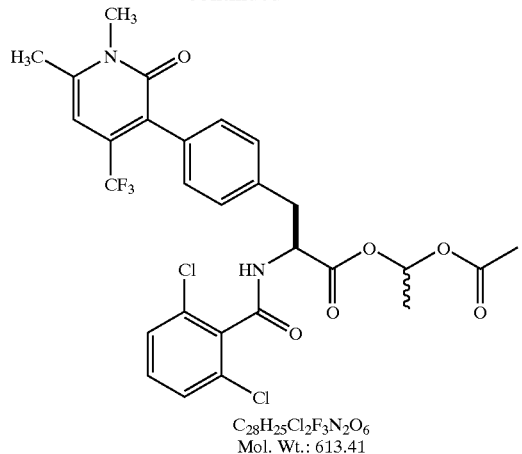

C28H25Cl2F3N2O6
Mol. Wt.: 613.41

To a mixture of N-[(2,6-dichlorophenyl)carbonyl]-4-[1,6-dimethyl-4-(trifluoromethyl)-2-oxo-3-pyridinyl]-L-phenylalanine (145 mg, 0.275 mmol), 2-diethylaminoethyl chloride hydrochloride (487 mg, 2.75 mmol) and potassium carbonate (380 mg, 2.7 mmol) was added ethyl acetate (3 mL) and water (3 mL) at room temperature. The mixture was stirred for 72 h at room temperature. Then, the reaction mixture was poured into a mixture of water (30 mL) and ethyl acetate (30 mL). The layers were separated and the aqueous layer was extracted with ethyl acetate (2×20 mL). The combined organic extracts were washed with brine solution (60 mL) and were dried over anhydrous magnesium sulfate. Filtration of the drying agent and concentration gave the crude product, which was purified by silica gel chromatography using a Biotage (40 s) column afforded 122 mg (71% yield) of N-[(2,6-dichlorophenyl)carbonyl]-4-[1,6-dimethyl-4-(trifluoromethyl)-2-oxo-3-pyridinyl]-L-phenylalanine 2-[(N,N-diethyl)amino]ethyl ester as an amorphous white solid. ES-HRMS m/e calcd for $C_{30}H_{32}Cl_2F_3N_3O_4$ (M+H) 626.1796. found 626.1802.

Example 40

Preparation of N-[(2,6-dichlorophenyl)carbonyl]-4-[1,6-dimethyl-4-(trifluoromethyl)-2-oxo-3-pyridinyl]-L-phenylalanine 1-(acetoxy)ethyl ester

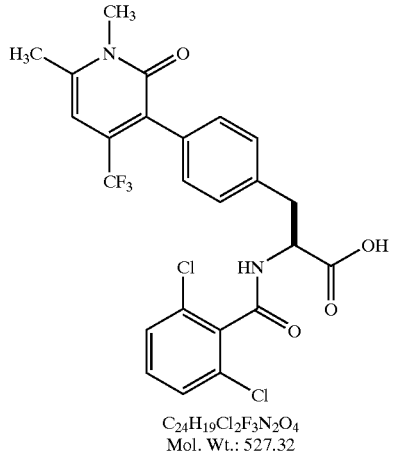

C24H19Cl2F3N2O4
Mol. Wt.: 527.32

To a suspension of N-[(2,6-dichlorophenyl)carbonyl]-4-[1,6-dimethyl-4-(trifluoromethyl)-2-oxo-3-pyridinyl]-L-phenylalanine (145 mg, 0.275 mmol) and sodium bicarbonate (185 mg, 2.2 mmol) in DMF (2 mL) was added 1-chloroethyl acetate (270 mg, 2.2 mmol) at room temperature. The mixture was stirred for 48 h at room temperature. Then, the reaction mixture was poured into water (30 mL) and was extracted with ethyl acetate (3×20 mL). The combined organic extracts were washed with brine solution (60 mL) and were dried over anhydrous magnesium sulfate. Filtration of the drying agent and concentration gave the crude product, which was purified by silica gel chromatography using a Biotage (40 s) column to afford 110 mg (65% yield) of N-[(2,6-dichlorophenyl)carbonyl]-4-[1,6-dimethyl-4-(trifluoromethyl)-2-oxo-3-pyridinyl]-L-phenylalanine 1-(acetoxy)ethyl ester as an amorphous white solid. ES-HRMS m/e calcd for $C_{28}H_{25}Cl_2F_3N_2O_6$ (M+Na) 635.0931. found 635.0932.

Example 41

Preparation of N-[(2-chloro-6-methylphenyl)carbonyl]-4-[1,6-dimethyl-4-(trifluoromethyl)-2-oxo-3-pyridinyl]-L-phenylalanine ethyl ester

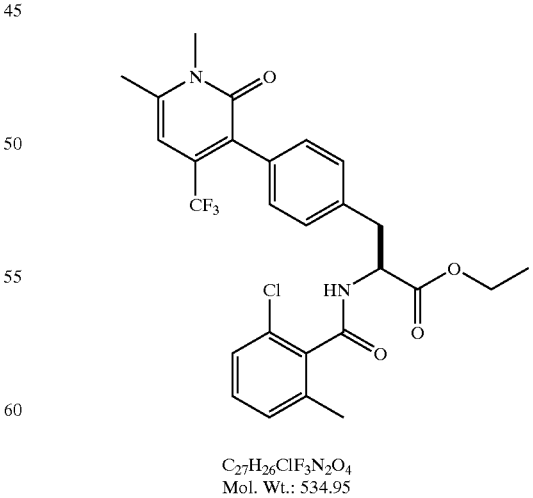

C27H26ClF3N2O4
Mol. Wt.: 534.95

N-[(2-chloro-6-methylphenyl)carbonyl]-4-[1,6-dimethyl-4-(trifluoromethyl)-2-oxo-3-pyridinyl]-L-phenylalanine ethyl ester can be prepared from N-[(2-chloro-6-methylphenyl)carbonyl]-4-[1,6-dimethyl-4-(trifluoromethyl)-2-oxo-3-pyridinyl]-L-phenylalanine and iodoethane using the general procedure described in example 38.

Example 42

Preparation of N-[(2-chloro-6-methylphenyl)carbonyl]-4-[1,6-dimethyl-4-(trifluoromethyl)-2-oxo-3-pyridinyl]-L-phenylalanine 2-[(N,N-diethyl)amino]ethyl ester

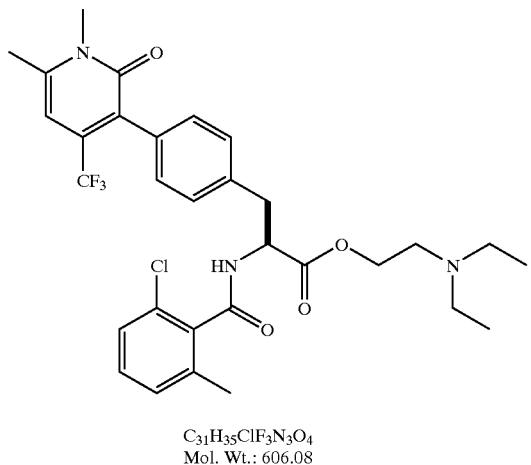

$C_{31}H_{35}ClF_3N_3O_4$
Mol. Wt.: 606.08

N-[(2-chloro-6-methylphenyl)carbonyl]-4-[1,6-dimethyl-4-(trifluoromethyl)-2-oxo-3-pyridinyl]-L-phenylalanine 2-[(N,N-diethyl)amino]ethyl ester can be prepared from N-[(2-chloro-6-methylphenyl)carbonyl]-4-[1,6-dimethyl-4-(trifluoromethyl)-2-oxo-3-pyridinyl]-L-phenylalanine and 2-[(N,N-diethyl)amino]ethyl chloride hydrochloride using the general procedure described in example 39.

Example 43

Preparation of N-[(2-chloro-6-methylphenyl)carbonyl]-4-[1,6-dimethyl-4-(trifluoromethyl)-2-oxo-3-pyridinyl]-L-phenylalanine 1-(acetoxy)ethyl ester

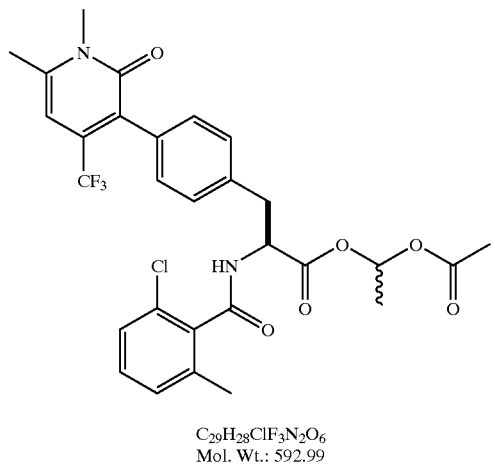

$C_{29}H_{28}ClF_3N_2O_6$
Mol. Wt.: 592.99

N-[(2-chloro-6-methylphenyl)carbonyl]-4-[1,6-dimethyl-4-(trifluoromethyl)-2-oxo-3-pyridinyl]-L-phenylalanine 1-(acetoxy)ethyl ester can be prepared from N-[(2-chloro-6-methylphenyl)carbonyl]-4-[1,6-dimethyl-4-(trifluoromethyl)-2-oxo-3-pyridinyl]-L-phenylalanine and 1-chloroethyl acetate using the general procedure described in example 40.

Example 44

Preparation of N-[(2,6-dichlorophenyl)carbonyl]-4-(1,4-dimethyl-6-(trifluoromethyl)-2-oxo-3-pyridinyl)-L-phenylalanine Preparation of 4-methoxy-1,1,1-trifluoropent-3-en-2-one

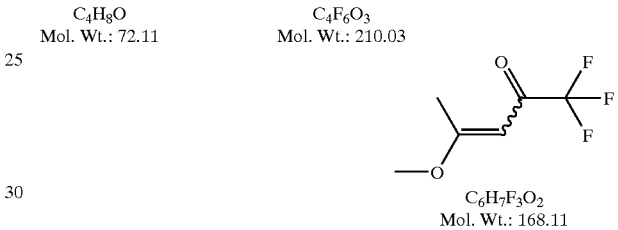

$C_4H_8O$  $C_4F_6O_3$
Mol. Wt.: 72.11  Mol. Wt.: 210.03

$C_6H_7F_3O_2$
Mol. Wt.: 168.11

To a solution of 2-methoxypropene (3.68 g, 51.03 mmol) and pyridine (1.35 g, 16.69 mmol) in dichloromethane (15 mL) was added a solution of trifluoroacetic anhydride (10 mL, 46.56 mmol) in dichloromethane (8 mL) at 0° C. over a period of 10–12 min. After addition, the solution turned to dark red-brown and then the cooling bath was removed and stirring was stopped. The mixture was allowed to stand for 16 h and was diluted with ice cold water (45 mL) and dichloromethane (120 mL). The two layers were separated and the organic layer was washed successively with 2N HCl (35 mL), saturated sodium carbonate solution (75 mL) and brine solution (25 mL) and was dried over anhydrous sodium sulfate. Filtration of the drying agent and concentration gave the crude product, which was purified by distillation under high vacuum to afford 5.546 g (65% yield) of 4-methoxy-1,1,1-trifluoropent-3-en-2-one as a light yellow oil.

b) Preparation of N-[(2,6-dichlorophenyl)carbonyl]-4-(1,4-dimethyl-6-(trifluoromethyl)-2-oxo-3-pyridinyl)-L-phenylalanine Preparation of 4-methoxy-1,1,1-trifluoropent-3-en-2-one

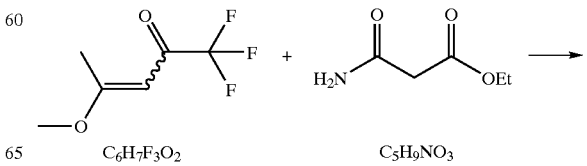

$C_6H_7F_3O_2$  $C_5H_9NO_3$
Mol. Wt.: 168.11  Mol. Wt.: 131.13

-continued

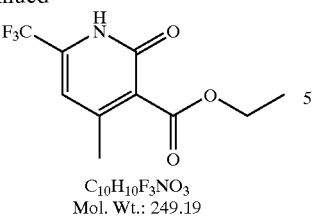

C₁₀H₁₀F₃NO₃
Mol. Wt.: 249.19

To a suspension of 4-methoxy-1,1,1-trifluoropent-3-en-2-one (5.53 g, 32.89 mmol) and ethyl malonate monoamide (4.31 g, 32.89 mmol) in ethanol (30 mL) was added sodium ethoxide (11.72 g, 36.18 mmol, 21% pure) at room temperature and the reaction mixture was heated to ~85° C. After stirring for 18 h, the reaction mixture was cooled to room temperature and 15% HCl (10 mL) was added. Then, it was diluted with water (10 mL) and was extracted with chloroform (2×50 mL). The combined extracts were washed with brine solution (100 mL) and were dried over anhydrous sodium sulfate. Filtration of the drying agent and concentration gave the crude product, which was purified by silica gel chromatography on a Biotage (40 m) column to afford 5.22 g (62% yield) of 4-methyl-2(1H)-oxo-6-(trifluoromethyl)pyridine-3-carboxylic acid ethyl ester as an amorphous white solid. ES-LRMS: m/z 313.4 (M+Na+ CH₃CN).

Preparation of N-[(2,6-dichlorophenyl)carbonyl]-4-(1,4-dimethyl-6-(trifluoromethyl)-2-oxo-3-pyridinyl)-L-phenylalanine Preparation of 4-methoxy-1,1,1-trifluoropent-3-en-2-one

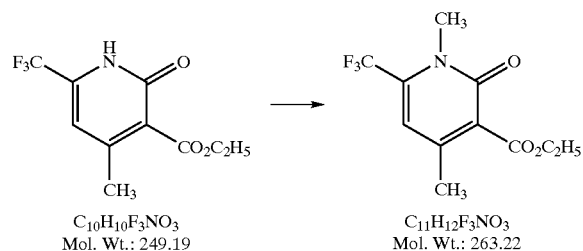

C₁₀H₁₀F₃NO₃
Mol. Wt.: 249.19

C₁₁H₁₂F₃NO₃
Mol. Wt.: 263.22

To a suspension of 4-methyl-2(1H)-oxo-6-(trifluoromethyl)pyridine-3-carboxylic acid ethyl ester (5.2 g, 20.87 mmol) and potassium carbonate (8.65 g, 62.59 mmol) in DME (50 mL) was added iodomethane (12 mL, 192.8 mmol) at room temperature and the reaction mixture was heated to reflux for 18 h. The reaction mixture was cooled to room temperature and the inorganic solids were filtered and the solids were washed with DME. The solvent was concentrated under vacuum and the residue was purified by silica gel chromatography on a Biotage (40 m) column to afford 4.02 g (71% yield) of 1,4-dimethyl-2(1H)-oxo-6-(trifluoromethyl)pyridine 3-carboxylic acid ethyl ester as an amorphous white solid. ES-HRMS m/e calcd for C₁₁H₁₂F₃NO₃ (M+Na) 286.0661. found 286.0664.

d) Preparation of 1,4-dimethyl-6-(trifluoromethyl)-1H-pyridin-2-one

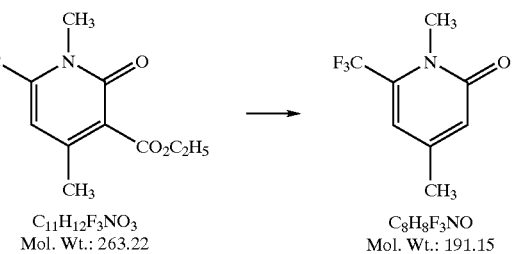

C₁₁H₁₂F₃NO₃
Mol. Wt.: 263.22

C₈H₈F₃NO
Mol. Wt.: 191.15

To a mixture of 1,4-dimethyl-2(1H)-oxo-6-(trifluoromethyl)pyridine-3-carboxylic acid ethyl ester (2.5 g, 9.5 mmol) and lithium chloride (1.0 g, 23.6 mmol) was added DMF (15 mL) and water (0.38 mL) at room temperature. The reaction mixture was heated to a bath temperature of 160° C. and stirred for 19 h. The reaction mixture was cooled to room temperature and diluted with cold ethyl acetate and diethyl ether (75 mL, 1:1). The resulting mixture was washed with cold water (3×20 mL) and brine solution (20 mL) and was dried over anhydrous sodium sulfate. Filtration of the drying agent and concentration of the solvent gave the crude product, which was purified by silica gel chromatography on a Biotage (40 s) column to afford 1.45 g (80% yield) of 1,4-dimethyl-6-(trifluoromethyl)-1H-pyridin-2-one as a light yellow solid. ES-HRMS m/e calcd for C₈H₈F₃NO (M+H) 192.0631. found 192.0632.

e) Preparation of 1,4-dimethyl-3-iodo-6-(trifluoromethyl)-1H-pyridin-2-one

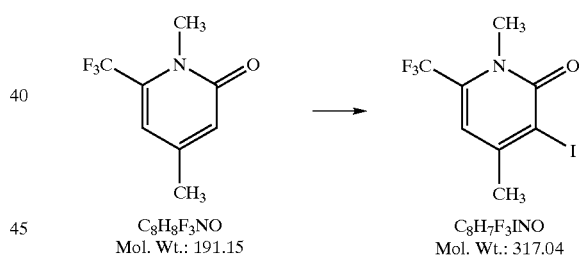

C₈H₈F₃NO
Mol. Wt.: 191.15

C₈H₇F₃INO
Mol. Wt.: 317.04

To a solution of 1,4-dimethyl-6-(trifluoromethyl)-1H-pyridin-2-one (1.44 g, 7.23 mmol), trifluoroacetic acid (9 mL) and trifluoroacetic anhydride (1.53 mL, 10.85 mmol) was added NIS (2.569 g, 10.85 mmol) at room temperature. Then, the mixture was heated to 70–85° C. and was stirred for 2 h. The reaction mixture was cooled to room temperature and saturated sodium carbonate solution was added slowly to neutralize the solution. Then, the aqueous mixture was extracted with ethyl acetate (2×50 mL). The combined extracts were washed successively with saturated sodium thiosulfate solution (100 mL) and brine solution (100 mL) and were dried over anhydrous sodium sulfate. Filtration of the drying agent and concentration of the solvent gave a crude product, which was purified by silica gel chromatography on a Biotage (40 m) column to afford 1.02 g (45% yield) of 1,4-dimethyl-3-iodo-6-(trifluoromethyl)-1H-pyridin-2-one as an amorphous white solid. ES-LRMS: m/z 318.1 (M+H), 381.2 (M+Na⁺ CH₃CN).

f) Preparation of N-[(1,1-dimethylethoxyl)carbonyl]-4-[1,4-dimethyl-6-(trifluoromethyl)-2-oxo-3-pyridinyl]-L-phenylalanine methyl ester

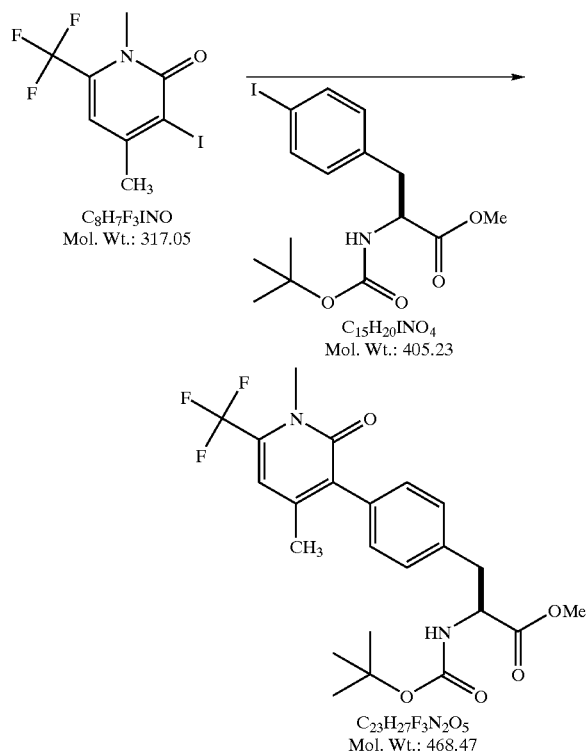

To a suspension of zinc dust (1.96 g, 30 mmol) in THF (1.0 mL) was added 1,2-dibromoethane (172 μL, 2 mmol)) at room temperature. This suspension was heated to 60–65° C. with a heat gun until evolution of ethylene gas ceased. Then, the suspension was cooled to room temperature and trimethylchlorosilane (150 μL, 1.2 mmol)) was added and the mixture was stirred for 15 min. A suspension of 1,4-dimethyl-3-iodo-6-(trifluoromethyl)-2-pyridone (2.4 g, 7.57 mmol) in DMA (6 mL) was warmed with a heat gun to effect dissolution and was added in one portion to the reaction mixture. After addition, the mixture was heated to 70–75° C. and was stirred for 2 h, at which time the TLC analysis of an aliquot, which had been quenched with saturated ammonium chloride solution, indicated the absence of starting material. The reaction mixture was diluted with THF (5 mL), was cooled to room temperature and the excess zinc dust was allowed to settle.

The above prepared solution containing the zinc compound (7.57 mmol) was added to a solution of Pd(dba)$_2$ (274 mg, 0.478 mmol), trifurylphosphine (391 mg, 1.287 mmol) and N-[(1,1-dimethylethoxy)carbonyl]-4-iodo-L-phenylalanine methyl ester (3 g, 7.411 mmol) in THF (7 mL) at room temperature and the light yellow mixture was stirred for 40 h at 50–55° C. The reaction mixture was poured into a saturated ammonium chloride solution and was extracted with ethyl acetate (3×70 mL). The combined extracts were washed with brine solution (100 mL) and were dried over anhydrous magnesium sulfate. Filtration of the drying agent and concentration gave the crude product, which was purified by silica gel chromatography on a Biotage (40 m) column to obtain 1.289 g (36% yield) of N-[(1,1-dimethylethoxyl)carbonyl]-4-[1,4-dimethyl-6-(trifluoromethyl)-2-oxo-3-pyridinyl]-L-phenylalanine methyl ester as an amorphous white solid. ES-HRMS m/e calcd for $C_{23}H_{27}F_3N_2O_5$ (M+Na) 491.1764. found 491.1764.

g) Preparation of 4-[1,6-dimethyl-4-(trifluoromethyl)-2-oxo-3-pyridinyl]-L-phenylalanine methyl ester hydrochloride salt

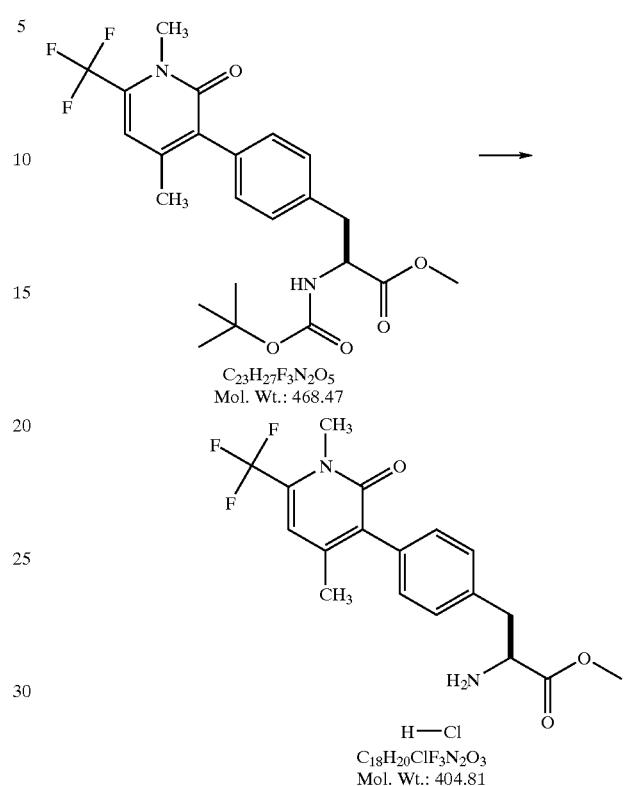

A N-[(1,1-dimethylethoxyl)carbonyl]-4-[1,4-dimethyl-6-(trifluoromethyl)-2-oxo-3-pyridinyl]-L-phenylalanine methyl ester (253 mg, 0.54 mmol) was treated with 4 N HCl solution in dioxane (4.0 mL) at room temperature. The solution was stirred for 2 h as a white solid was formed. The mixture was concentrated and the residue was dissolved in methanol. After removal of methanol, the residue was dried under high vacuum to obtain 221 mg (100% yield) of 4-[1,4-dimethyl-6-(trifluoromethyl)-2-oxo-3-pyridinyl]-L-phenylalanine methyl ester hydrochloride salt as an amorphous white solid. ES-LRMS m/z 369.3 (M+H), 410.3 (M+CH3CN).

h) Preparation of N-[(2,6-dichlorophenyl)carbonyl]-4-[1,4-dimethyl-6-(trifluoromethyl)-2-oxo-3-pyridinyl]-L-phenylalanine methyl ester

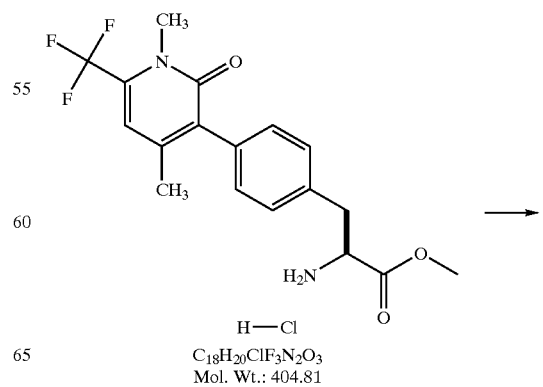

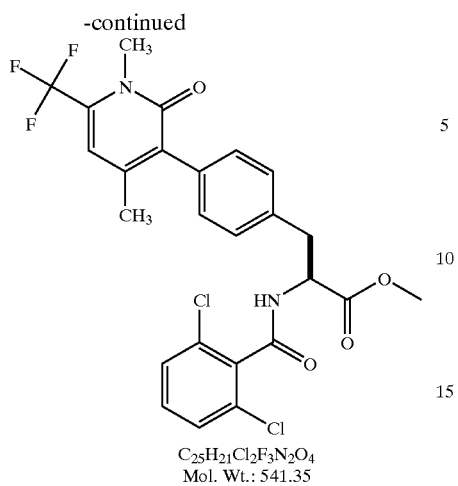

C₂₅H₂₁Cl₂F₃N₂O₄
Mol. Wt.: 541.35

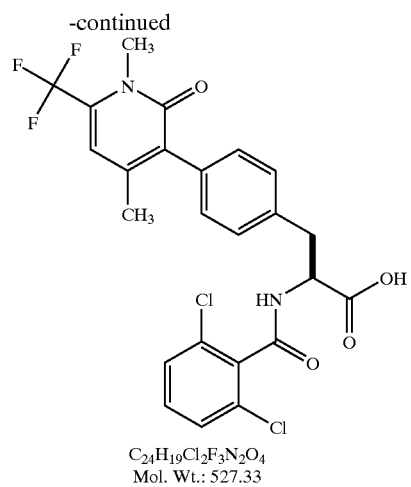

C₂₄H₁₉Cl₂F₃N₂O₄
Mol. Wt.: 527.33

To a suspension of 4-[1,4-dimethyl-6-(trifluoromethyl)-2-oxo-3-pyridinyl]-L-phenylalanine methyl ester hydrochloride salt (216 mg, 0.53 mmol) and 2,6-dichlorobenzoyl chloride (120 mg, 0.57 mmol) in THF (6 mL) was added DIEA (210 µL, 1.19 mmol) at room temperature. After 5 min, a clear solution was obtained which was stirred for 18 h. Then, the mixture was diluted with ethyl acetate (50 mL). The ethyl acetate solution was washed successively with 0.5 N HCl (50 mL), saturated NaHCO₃ solution (50 mL) and brine solution (50 mL) and was dried over anhydrous magnesium sulfate. Filtration of the drying agent and concentration gave crude product, which was dissolved in ethyl acetate (~3 mL) and hexanes (~3–4 mL) was added and stored in the refrigerator. The solid was collected and washed with hexanes. After drying under high vacuum, 270 mg (93.5% yield) of N-[(2,6-dichlorophenyl)carbonyl]-4-[1,4-dimethyl-6-(trifluoromethyl)-2-oxo-3-pyridinyl]-L-phenylalanine methyl ester was obtained a white solid: mp 170–173° C. ES-HRMS m/e calcd for C₂₅H₂₁Cl₂F₃N₂O₄ (M+Na) 563.0724. found 563.0730.

Preparation of N-[(2,6-dichlorophenyl)carbonyl]-4-(1,4-dimethyl-6-(trifluoromethyl)-2-oxo-3-pyridinyl)-L-phenylalanine

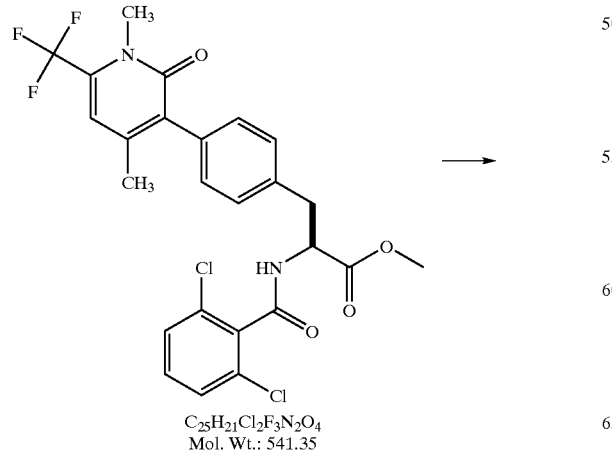

C₂₅H₂₁Cl₂F₃N₂O₄
Mol. Wt.: 541.35

To a suspension of N-[(2,6-dichlorophenyl)carbonyl]-4-[1,4-dimethyl-6-(trifluoromethyl)-2-oxo-3-pyridinyl]-L-phenylalanine methyl ester (243 mg, 0.45 mmol) in ethanol (5 mL) was added 1N aqueous sodium hydroxide solution (1.8 mL) at room temperature. The mixture was heated to 45–50° C. and was stirred for 2 h. Then, the ethanol was removed under vacuum and the residue was diluted with water (20 mL). The aqueous solution was washed with ethyl acetate (50 mL) to remove any neutral impurities. The aqueous layer was acidified with 1.0 N HCl and the product was extracted with ethyl acetate (2×50 mL). The combined organic extracts were washed with brine solution (50 mL) and were dried over anhydrous magnesium sulfate. Filtration of the drying agent and concentration afforded 186 mg (79% yield) of N-[(2,6-dichlorophenyl)carbonyl]-4-[1,4-dimethyl-6-(trifluoromethyl)-2-oxo-3-pyridinyl]-L-phenylalanine as an amorphous white solid. ES-HRMS m/e calcd for C₂₄H₁₉Cl₂F₃N₂O₄ (M+Na) 549.0567. found 549.0573.

Example 45

Preparation of N-[(2-chloro-6-methylphenyl)carbonyl]-4-(1,4-dimethyl-6-(trifluoromethyl)-2-oxo-3-pyridinyl)-L-phenylalanine

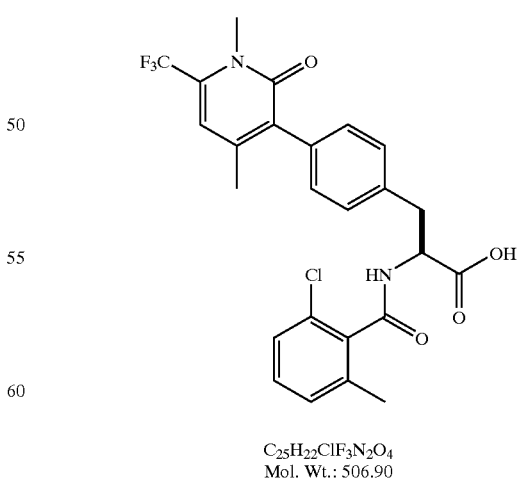

C₂₅H₂₂ClF₃N₂O₄
Mol. Wt.: 506.90

N-[(2-chloro-6-methylphenyl)carbonyl]-4-(1,4-dimethyl-6-(trifluoromethyl)-2-oxo-3-pyridinyl)-L-phenylalanine was prepared from 4-[1,4-dimethyl-6-(trifluoromethyl)-2-oxo-3-pyridinyl]-L-phenylalanine methyl ester and 2-chloro-6-methylbenzoyl chloride using the general procedures described in example 44. ES-LRMS m/z 507.1 (M+H), 529.1 (M+Na).

Example 46

Preparation of N-[(2-chloro-6-methylphenyl)carbonyl]-4-[1,4-dimethyl-6-(trifluoromethyl)-2-oxo-3-pyridinyl]-L-phenylalanine ethyl ester

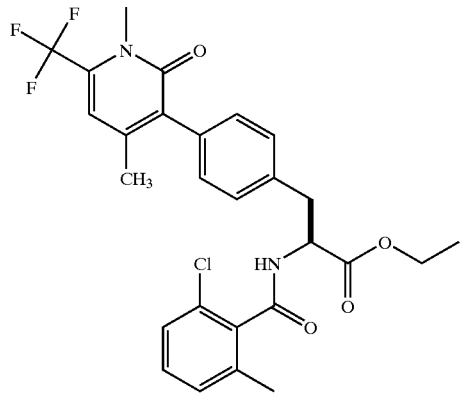

$C_{27}H_{26}ClF_3N_2O_4$
Mol. Wt.: 534.95

N-[(2-chloro-6-methylphenyl)carbonyl]-4-[1,4-dimethyl-6-(trifluoromethyl)-2-oxo-3-pyridinyl]-L-phenylalanine ethyl ester can be prepared from N-[(2-chloro-6-methylphenyl)carbonyl]-4-[1,4-dimethyl-6-(trifluoromethyl)-2-oxo-3-pyridinyl]-L-phenylalanine and iodoethane using the general procedure described in example 38.

Example 47

Preparation of N-[(2-chloro-6-methylphenyl)carbonyl]-4-[1,4-dimethyl-6-(trifluoromethyl)-2-oxo-3-pyridinyl]-L-phenylalanine 2-[(N,N-diethyl)amino]ethyl ester

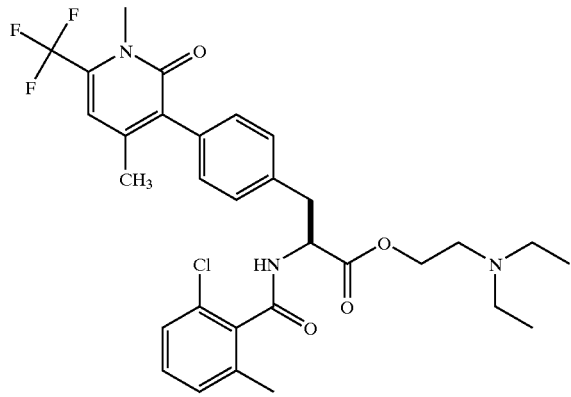

$C_{31}H_{35}ClF_3N_3O_4$
Mol. Wt.: 606.08

N-[(2-chloro-6-methylphenyl)carbonyl]-4-[1,4-dimethyl-6-(trifluoromethyl)-2-oxo-3-pyridinyl]-L-phenylalanine 2-[(N,N-diethyl)amino]ethyl ester can be prepared from N-[(2-chloro-6-methylphenyl)carbonyl]-4-[1,4-dimethyl-6-(trifluoromethyl)-2-oxo-3-pyridinyl]-L-phenylalanine and 2-[(N,N-diethyl)amino]ethyl chloride hydrochloride using the general procedure described in example 39.

Example 48

Preparation of N-[(2-chloro-6-methylphenyl)carbonyl]-4-[1,4-dimethyl-6-(trifluoromethyl)-2-oxo-3-pyridinyl]-L-phenylalanine 1-(acetoxy)ethyl ester

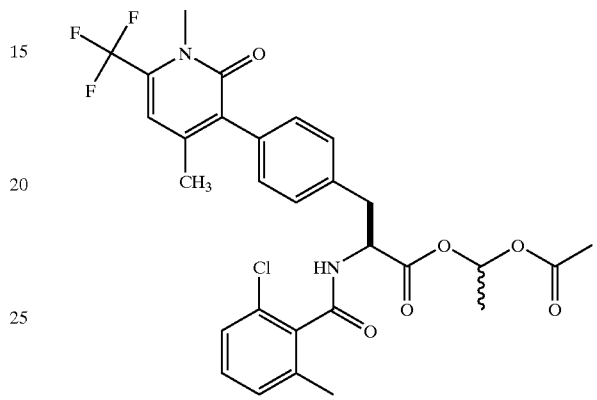

$C_{29}H_{28}ClF_3N_2O_6$
Mol. Wt.: 592.99

N-[(2-chloro-6-methylphenyl)carbonyl]-4-[1,4-dimethyl-6-(trifluoromethyl)-2-oxo-3-pyridinyl]-L-phenylalanine 1-(acetoxy)ethyl ester can be prepared from N-[(2-chloro-6-methylphenyl)carbonyl]-4-[1,4-dimethyl-6-(trifluoromethyl)-2-oxo-3-pyridinyl]-L-phenylalanine and 1-chloroethyl acetate using the general procedure described in example 40.

Example 49

Preparation of N-[(2,6-dichlorophenyl)carbonyl]-4-[1,4-dimethyl-6-(trifluoromethyl)-2-oxo-3-pyridinyl]-L-phenylalanine ethyl ester

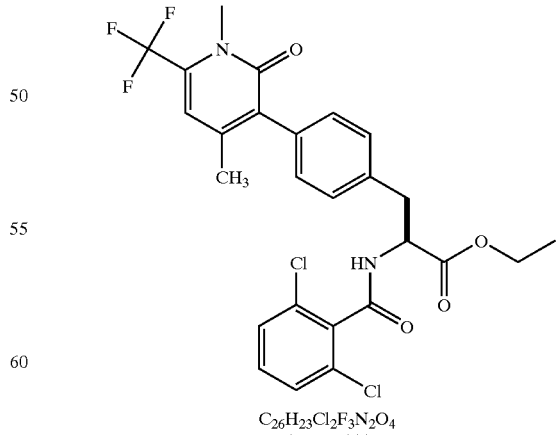

$C_{26}H_{23}Cl_2F_3N_2O_4$
Mol. Wt.: 555.37

N-[(2,6-dichlorophenyl)carbonyl]-4-[1,4-dimethyl-6-(trifluoromethyl)-2-oxo-3-pyridinyl]-L-phenylalanine ethyl ester can be prepared from N-[(2,6-dichlorophenyl)carbonyl]-4-[1,4-dimethyl-6-(trifluoromethyl)-2-oxo-3-pyridinyl]-L-phenylalanine and iodoethane using the general procedure described in example 38.

Example 50

Preparation of N-[(2,6-dichlorophenyl)carbonyl]-4-[1,4-dimethyl-6-(trifluoromethyl)-2-oxo-3-pyridinyl]-L-phenylalanine 2-[(N,N-diethyl)amino]ethyl ester

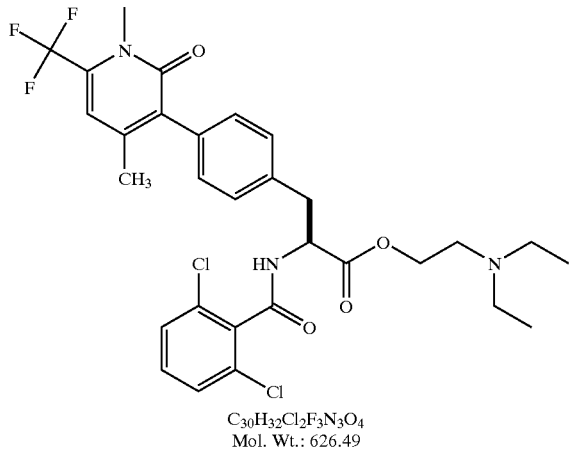

$C_{30}H_{32}Cl_2F_3N_3O_4$
Mol. Wt.: 626.49

N-[(2,6-dichlorophenyl)carbonyl]-4-[1,4-dimethyl-6-(trifluoromethyl)-2-oxo-3-pyridinyl]-L-phenylalanine 2-[(N,N-diethyl)amino]ethyl ester can be prepared from N-[(2,6-dichlorophenyl)carbonyl]-4-[1,4-dimethyl-6-(trifluoromethyl)-2-oxo-3-pyridinyl]-L-phenylalanine and 2-[(N,N-diethyl)amino]ethyl chloride hydrochloride using the general procedure described in example 39.

Example 51

Preparation of N-[(2,6-dichlorophenyl)carbonyl]-4-[1,4-dimethyl-6-(trifluoromethyl)-2-oxo-3-pyridinyl]-L-phenylalanine 1-(acetoxy)ethyl ester

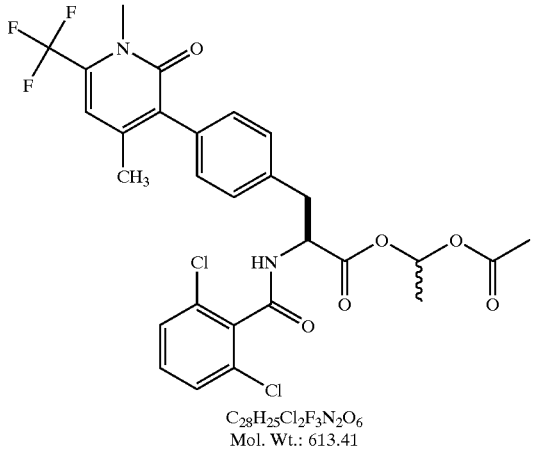

$C_{28}H_{25}Cl_2F_3N_2O_6$
Mol. Wt.: 613.41

N-[(2,6-dichlorophenyl)carbonyl]-4-[1,4-dimethyl-6-(trifluoromethyl)-2-oxo-3-pyridinyl]-L-phenylalanine 1-(acetoxy)ethyl ester can be prepared from N-[(2,6-dichlorophenyl)carbonyl]-4-[11,4-dimethyl-6-(trifluoromethyl)-2-oxo-3-pyridinyl]-L-phenylalanine and 1-chloroethyl acetate using the general procedure described in example 40.

BIOASSAY EXAMPLES

Example A

VLA-4/VCAM-1 Screening Assay

VLA-4 antagonist activity, defined as ability to compete for binding to immobilized VCAM-1, was quantitated using a solid-phase, dual antibody ELISA. VLA-4 ($\alpha 4\beta 1$ integrin) bound to VCAM-1 was detected by a complex of anti-integrin $\beta 1$ antibody: HRP-conjugated anti-mouse IgG: chromogenic substrate (K-Blue). Initially, this entailed coating 96 well plates (Nunc Maxisorp) with recombinant human VCAM-1 (0.4 $\mu$g in 100 $\mu$l PBS), sealing each plate and then allowing the plates to stand at 4° C. for ~18 hr. The VCAM-coated plates were subsequently blocked with 250 $\mu$L of 1% BSA/0.02% $NaN_3$ to reduce non-specific binding. On the day of assay, all plates were washed twice with VCAM Assay Buffer (200 $\mu$l/well of 50 mM Tris-HCl, 100 mM NaCl, 1 mM $MnCl_2$, 0.05% Tween 20; pH 7.4). Test compounds were dissolved in 100% DMSO and then diluted 1:20 in VCAM Assay Buffer supplemented with 1 mg/mL BSA (i.e., final DMSO=5%). A series of 1:4 dilutions were performed to achieve a concentration range of 0.005 nM–1.563 $\mu$M for each test compound. 100 $\mu$l per well of each dilution was added to the VCAM-coated plates, followed by 10 $\mu$l of Ramos cell-derived VLA-4. These plates were sequentially mixed on a platform shaker for 1 min, incubated for 2 hr at 37° C., and then washed four times with 200 $\mu$l/well VCAM Assay Buffer. 100 $\mu$l of mouse anti-human integrin $\beta 1$ antibody was added to each well (0.6 $\mu$g/mL in VCAM Assay Buffer+1 mg/mL BSA) and allowed to incubate for 1 hr at 37° C. At the conclusion of this incubation period, all plates were washed four times with VCAM Assay Buffer (200 $\mu$l/well). A corresponding second antibody, HRP-conjugated goat anti-mouse IgG (100 $\mu$l per well @ 1:800 dilution in VCAM Assay Buffer+1 mg/mL BSA), was then added to each well, followed by a 1 hr incubation at room temperature and concluded by three washes (200 $\mu$l/well) with VCAM Assay Buffer. Color development was initiated by addition of 100 $\mu$l K-Blue per well (15 min incubation, room temp) and terminated by addition of 100 $\mu$l Red Stop Buffer per well. All plates were then read in a UV/Vis spectrophotometer at 650 nM. Results were calculated as % inhibition of total binding (i.e., VLA-4+VCAM-1 in the absence of test compound).

The results are provided in the following Table I (A=$IC_{50}$<1 nM, B=$IC_{50}$<10 nM):

TABLE I

| Compound of Example | Activity in VCAM/VLA-4 ELISA Assay |
| --- | --- |
| 8 | A |
| 10 | B |
| 15 | B |
| 17 | B |
| 24 | A |
| 28 | A |

Example B

Ramos (VLA-4)/VCAM-1 Cell-Based Screening Assay Protocol

Materials:

Soluble recombinant human VCAM-1 (mixture of 5- and 7-Ig domain) was purified from CHO cell culture media by immunoaffinity chromatography and maintained in a solution containing 0.1 M Tris-glycine (pH 7.5), 0.1 M NaCl, 5 mM EDTA, 1 mM PMSF, 0.02% 0.02% $NaN_3$ and 10 µg/mL leupeptin. Calcein-AM was purchased from Molecular Probes Inc.

Methods:

VLA-4 ($\alpha 4\beta 1$ integrin) antagonist activity, defined as ability to compete with cell-surface VLA-4 for binding to immobilized VCAM-1, was quantitated using a Ramos-VCAM-1 cell adhesion assay. Ramos cells bearing cell-surface VLA-4, were labeled with a fluorescent dye (Calcein-AM) and allowed to bind VCAM-1 in the presence or absence of test compounds. A reduction in fluorescence intensity associated with adherent cells (% inhibition) reflected competitive inhibition of VLA-4 mediated cell adhesion by the test compound.

Initially, this entailed coating 96 well plates (Nunc Maxisorp) with recombinant human VCAM-1 (100 ng in 100 µl PBS), sealing each plate and allowing the plates to stand at 4° C. for ≈18 hr. The VCAM-coated plates were subsequently washed twice with 0.05% Tween-20 in PBS, and then blocked for 1 hr (room temperature) with 200 µl of Blocking Buffer (1% BSA/0.02% thimerosal) to reduce non-specific binding. Following the incubation with Blocking Buffer, plates were inverted, blotted and the remaining buffer aspirated. Each plate was then washed with 300 µl PBS, inverted and the remaining PBS aspirated.

Test compounds were dissolved in 100% DMSO and then diluted 1:25 in VCAM Cell Adhesion Assay Buffer (4 mM $CaCl_2$, 4 mM $MgCl_2$ in 50 mM TRIS-HCl, pH 7.5) (final DMSO=4%). A series of eight 1:4 dilutions were performed for each compound (general concentration range of 1 nM–12,500 nM). 100 µl/well of each dilution was added to the VCAM-coated plates, followed by 100 µl of Ramos cells (200,000 cells/well in 1% BSA/PBS). Plates containing test compounds and Ramos cells were allowed to incubate for 45 min at room temperature, after which 165 µl/well PBS was added. Plates were inverted to remove non-adherent cells, blotted and 300 µL/well PBS added. Plates were again inverted, blotted and the remaining buffer gently aspirated. 100 µl Lysis Buffer (0.1% SDS in 50 mM TRIS-HCl, pH 8.5) was added to each well and agitated for 2 min on a rotary shaking platform. The plates were then read for fluorescence intensity on a Cytofluor 2300 (Millipore) fluorecence measurement system (excitation=485 nm, emission=530 nm). The results are shown in the following table:

The results are provided in the following Table II (A=$IC_{50}$<100 nM, B=$IC_{50}$<10000 nM, C=$IC_{50}$<5,000 nM):

TABLE II

| Compound of Example | Activity in VCAM/VLA-4 Ramos Cell Assay |
|---|---|
| 8 | B |
| 10 | B |
| 15 | C |
| 24 | B |
| 28 | C |
| 30 | B |
| 31 | B |
| 32 | B |
| 33 | A |
| 34 | B |
| 35 | B |
| 36 | A |
| 37 | B |

Example C
Alpha4-Beta7 Assay Protocol

Two weeks to one day prior to the assay, Nunc high-binding F96 Maxisorp immuno plates, #442404 or #439454, were coated with 25 ng/well (0.25 µg/ml) MadCAM in a volume of 100 µl/well. The plates were covered with sealer and wrapped in saran wrap followed by incubation in the refrigerator for at least 24 hours. The coating buffer employed was: 10 mM carbonate/bicarbonate buffer made up from: 0.8 g/L sodium carbonate and 1.55 g/L sodium bicarbonate adjusted to pH 9.6 with 1 N HCl.

Assay buffers consisted of the following:
Wash Buffer: 0.05% Tween 20 in PBS
Blocking Buffer: 1% Nonfat Dry Milk in PBS
Labeling Buffer: PBS
Cell Buffer: RPMI 1640 medium (no additives)
Binding Buffer: 1.5 mM $CaCl_2$
0.5 mM $MnCl_2$
50 mM TRIS-HCl; add NaOH dropwise to pH 7.5
Bring to volume in $H_2O$
Adjust to pH 7.5
Dilution Buffer: 4% DMSO in Binding Buffer Plates were washed 2× with wash buffer and then blocked at room temperature for at least 1 hour with Blocking Buffer. Sealed plates were sometimes blocked overnight in the refrigerator. Plates were then washed with PBS and hand blotted dry. Remaining liquid was aspirated from the wells.

Sufficient RPMI 8866 cells were removed from stock for assay ($2\times10^6$ cells/ml×10 ml/plate×number of plates) and placed in a centrifuge tube. The tubes were filled to volume with PBS and were spun at 200×G for 8 minutes. The buffer was poured off and the cells were resuspended to $10\times10^6$/ml in PBS and a stock solution of calcein in DMSO (5 mg/mL) was added at 5 µl/ml of cell suspension. The suspension was incubated for 30 minutes at 37° C. in dark. The cells were then washed with PBS. The PBS was poured off and the cells resuspended in cell buffer at a concentration of $2\times10^6$ cells/mL for plating in the assay.

Stock solution of test compounds at 25× first dilution desired in 100% DMSO were prepared. First dilutions for the standard, as well as test compounds, were 1:25 into straight Binding Buffer, while the remaining serial dilutions were into Dilution Buffer (Binding Buffer/4% DMSO). Stock concentrations and dilutions of compounds for screening were determined by anticipated activity.

For the assay, 129 µl Binding Buffer was plated into first row of wells and 100 µl Dilution Buffer was plated into remaining wells. A 5.4 µl aliquot of each compound was pipetted into appropriate, labeled wells, in triplicate. The compounds were next diluted down the plate (34 µl+100 µl=>4-fold dilution). For controls, 100 µl of Dilution Buffer+100 µl Cell Buffer were plated into the nonspecific background wells (no cells, no compound) and 100 µl Dilution Buffer+100 µl cells were plated into the total binding wells (no compound=100% binding). Labeled cells at $2\times10^6$ cells/ml, 100µl/well (=$2\times10^5$ cells/well) were added to each well containing compound. The plates were sealed and incubated in the dark for 45 minutes at room temperature. Following incubation, unbound cells were removed by adding 150 µl PBS/well. The plates were inverted, blotted onto paper towels and washed by gently adding 200 µl PBS to wells and blotting again. Remaining buffer was carefully aspirated from the wells. A final 100 µl PBS was added to each well.

The plates were then read for fluorescence intensity on a Cytofluor 2300 (Millipore) fluorecence measurement system (excitation=485 nm, emission=530 nm). $IC_{50}$s of each compound were determined by linear regression analysis.

The results are shown in the following table:
The results are provided in the following Table III:

TABLE III

| Compound of Example | Activity in MadCAM/RPMI Cell Assay (A = $IC_{50}$ < 100 nM, B = $IC_{50}$ < 10000 nM, C = $IC_{50}$ < 5,000 nM) |
|---|---|
| 30 | B |
| 31 | B |
| 32 | B |
| 33 | A |
| 34 | B |
| 35 | C |
| 36 | B |
| 37 | B |

What is claimed is:

1. A compound of the formula:

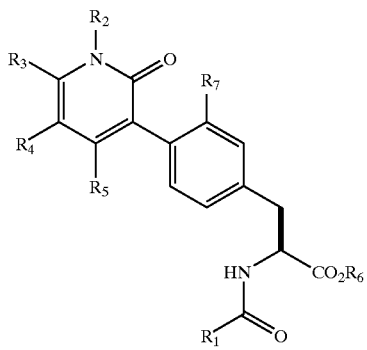

wherein $R_1$ is a group of the formula Y-1

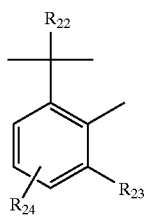

wherein $R_{22}$ and $R_{23}$ are independently hydrogen, lower alkyl, lower alkoxy, cycloalkyl, aryl, arylalkyl, nitro, cyano, lower alkylthio, lower alkylsulfinyl, lower alkyl sulfonyl, lower alkanoyl, halogen, or perfluorolower alkyl and at least one of $R_{22}$ and $R_{23}$ is other than hydrogen, and $R_{24}$ is hydrogen, lower alkyl, lower alkoxy, aryl, nitro, cyano, lower alkyl sulfonyl, or halogen; or $R_1$ is a a group of the formula Y-2, which is a five or six membered heteroaromatic ring bonded via a carbon atom to the amide carbonyl wherein said ring contains one, two or three heteroatoms selected from the group consisting of N, O and S and one or two atoms of said ring are independently substituted by lower alkyl, cycloalkyl, halogen, cyano, perfluoro lower alkyl, or aryl and at least one of said substituted atoms is adjacent to the carbon atom bonded to the amide carbonyl; or $R_1$ is a group of the formula Y-3 which is a 3–7 membered ring of the formula:

wherein $R_{25}$ is lower alkyl, unsubstituted or fluorine substituted lower alkenyl, or a group of formula $R_{26}$—$(CH_2)_e$—, $R_{26}$ is aryl, heteroaryl, azido, cyano, hydroxy, lower alkoxy, lower alkoxycarbonyl, lower alkanoyl, lower alkylthio, lower alkyl sulfonyl, lower alkyl sulfinyl, perfluoro lower alkanoyl, nitro, or $R_{26}$ is a group of formula —$NR_{28}R_{29}$, wherein $R_{28}$ is hydrogen or lower alkyl, $R_{29}$ is hydrogen, lower alkyl, lower alkoxycarbonyl, lower alkanoyl, aroyl, perfluoro lower alkanoylamino, lower alkyl sulfonyl, lower alkylaminocarbonyl, arylaminocarbonyl; or $R_{28}$ and $R_{29}$, taken together with the attached nitrogen atom, form a 4, 5 or 6-membered saturated heterocyclic ring optionally containing one additional heteroatom selected from O, S, and N—$R_{40}$, Q is —$(CH_2)_f O$—, —$(CH_2)_f S$—, —$(CH_2)_f N(R_{27})$—, —$(CH_2)_f$—, $R_{27}$ is H, lower alkyl, aryl, lower alkanoyl, aroyl or lower alkoxycarbonyl, $R_{40}$ is H, lower alkyl, aryl, lower alkanoyl, aroyl or lower alkoxycarbonyl, the carbon atoms in the ring are unsubstituted or substituted by lower alkyl or halogen, e is an integer from 0 to 4, and f is an integer from 0 to 3;

$R_2$ is hydrogen, lower alkyl, substituted lower alkyl, aryl, or aryl lower alkyl;

$R_3$ is hydrogen, halogen, lower alkyl, trifluoromethyl, or aryl;

$R_4$ is hydrogen, halogen, lower alkyl, or aryl;

$R_5$ is hydrogen, lower alkyl, lower alkoxy, or trifluoromethyl, or OH;

$R_6$ is hydrogen, lower alkyl, lower alkylcarbonyloxy lower alkyl, or $R_6$ is a group of formula P-3:

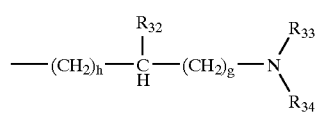

wherein:

$R_{32}$ is hydrogen or lower alkyl; $R_{33}$ is hydrogen, lower alkyl, aryl; $R_{34}$ is hydrogen or lower alkyl; h is an integer from 0 to 2; g is an integer from 0 to 2; the sum of h and g is 1 to 3; or $R_6$ is a group of formula P-4:

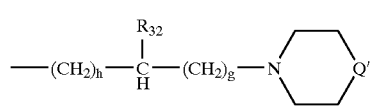

wherein: $R_{32}$, g, and h are as previously defined; Q' is O, S, —$(CH_2)_j$—, or a group of the formula N—$R_{35}$; wherein $R_{35}$ is hydrogen, lower alkyl, lower alkanoyl, lower alkoxycarbonyl; j is 0, 1 or 2; and $R_7$ is hydrogen, chloro, lower alkoxy, or lower alkyl; or the pharmaceutically acceptable salts thereof.

2. A compound of claim 1 wherein Q is —$(CH_2)_fO$—, —$(CH_2)_fS$—, or, —$(CH_2)_f$—.

3. A compound of claim 2 wherein $R_5$ is hydrogen, lower alkyl, or trifluoromethyl.

4. A compound of claim 1 wherein $R_1$ is a group of the formula Y-1 wherein $R_{22}$ and $R_{23}$ are independently lower alkyl or halogen and $R_{24}$ is hydrogen.

5. A compound of claim 1 wherein $R_1$ is a group of the formula Y-1 wherein $R_{22}$ and $R_{23}$ are independently hydrogen, lower alkyl or halogen and $R_{24}$ is hydrogen, lower alkyl or lower alkoxy.

6. A compound of claim 5 wherein $R_{22}$ and $R_{23}$ are independently hydrogen, lower alkyl or halogen, $R_{24}$ is hydrogen or lower alkoxy and $R_2$ is aryl lower alkyl.

7. A compound of claim 1 wherein $R_1$ is a group of the formula Y-3 wherein $R_{25}$ a group of formula $R_{26}$—$(CH_2)_e$—, wherein $R_{26}$ is lower alkoxy, Q is —$(CH_2)_f$—, e is an integer from 0 to 4 and f is an integer from 0 to 3.

8. A compound of claim 1 wherein $R_1$ is a group of the formula Y-3 and $R_2$ is hydrogen, lower alkyl, substituted lower alkyl or aryl lower alkyl.

9. A compound of claim 8 wherein $R_1$ is a group of the formula Y-3 wherein $R_{25}$ is a group of formula $R_{26}$—$(CH_2)_e$—, wherein $R_{26}$ is lower alkoxy, Q is —$(CH_2)_f$—, e is an integer from 0 to 4, f is an integer from 0 to 3; and $R_2$ is aryl lower alkyl.

10. A compound of claim 1 wherein
$R_2$ is hydrogen, lower alkyl or aryl lower alkyl;
$R_3$ is hydrogen;
$R_4$ is hydrogen or halogen;
$R_5$ is hydrogen, lower alkyl, or trifluoromethyl, or lower alkoxy;
$R_6$ is hydrogen or lower alkyl; and
$R_7$ is hydrogen, chloro, lower alkoxy, or lower alkyl.

11. A compound of claim 10 wherein $R_1$ is a group of the formula Y-1.

12. A compound of claim 11 wherein $R_1$ is a group of the formula Y-1 wherein $R_{22}$ and $R_{23}$ are independently lower alkyl or halogen and $R_{24}$ is hydrogen or lower alkoxy.

13. A compound of claim 11 wherein $R_1$ is a group of the formula Y-1 wherein $R_{22}$ and $R_{23}$ are independently hydrogen, lower alkyl or halogen and $R_{24}$ is hydrogen, lower alkyl or lower alkoxy.

14. A compound of claim 13 wherein $R_1$ is a group of the formula Y-1 wherein $R_{22}$ and $R_{23}$ are independently hydrogen, lower alkyl or halogen, $R_{24}$ is hydrogen and $R_2$ is aryl lower alkyl.

15. A compound of claim 10 wherein $R_1$ is a group of the formula Y-2.

16. A compound of claim 10 wherein $R_1$ is a group of the formula Y-3.

17. A compound of claim 16 wherein $R_1$ is a group of the formula Y-3 wherein $R_{25}$ is a group of formula $R_{26}$—$(CH_2)_e$—, wherein $R_{26}$ is lower alkoxy, Q is —$(CH_2)_f$—, e is an integer from 0 to 4 and f is an integer from 0 to 3.

18. A compound of claim 10 wherein $R_1$ is a group of the formula Y-3 wherein $R_{25}$ is a group of formula $R_{26}$—$(CH_2)_e$—, wherein $R_{26}$ is lower alkoxy, Q is —$(CH_2)_f$—, e is an integer from 0 to 4, f is an integer from 0 to 3, and $R_2$ is aryl lower alkyl.

19. A compound of claim 10 wherein
$R_2$ is hydrogen, lower alkyl or aryl lower alkyl;
$R_3$ is hydrogen;
$R_4$ is halogen;
$R_5$ is hydrogen;
$R_6$ is hydrogen or lower alkyl; and
$R_7$ is hydrogen, chloro, lower alkoxy, or lower alkyl.

20. A compound of claim 3 wherein $R_1$ is a group of formula Y-1 or a group of formula Y-3;
$R_2$ is hydrogen, lower alkyl or aryl lower alkyl;
$R_3$ is hydrogen, lower alkyl, or trifluoromethyl;
$R_4$ is hydrogen or halogen;
$R_5$ is hydrogen, lower alkyl, or trifluoromethyl;
$R_6$ is hydrogen, lower alkyl, lower alkylcarbonyloxy lower alkyl, a group of formula P-3;
or a group of formula P-4, and
$R_7$ is hydrogen or lower alkyl.

21. A compound of claim 20 wherein
$R_2$ is lower alkyl or aryl lower alkyl;
$R_6$ is hydrogen, lower alkyl, lower alkylcarbonyloxy lower alkyl, or a group of formula P-3; and
$R_7$ is hydrogen.

22. A compound of claim 21 wherein $R_{22}$ and $R_{23}$ are hydrogen, halogen or lower alkyl, $R_{24}$ is hydrogen or lower alkoxy, $R_{25}$ is a group of formula $R_{26}$—$(CH_2)_e$—, wherein $R_{26}$ is lower alkoxy, Q is —$(CH_2)_f$—, e is an integer from 0 to 4 and f is an integer from 0 to 3.

23. A compound of claim 22 wherein $R_2$ is lower alkyl, $R_4$ is hydrogen, and $R_3$ and $R_5$ are lower alkyl or trifluoromethyl.

24. A compound of claim 23 where $R_6$ is hydrogen.

25. A compound of claim 24 wherein $R_1$ is Y-3.

26. A compound of claim 25 which is N-[[1-(2-methoxyethyl)cyclopentyl]carbonyl]-4-[1,6-dimethyl-4-(trifluoromethyl)-2-oxo-3-pyridinyl]-L-phenylalanine.

27. A compound of claim 23 wherein $R_6$ is lower alkyl.

28. A compound of claim 27 which is N-[(2,6-dichlorophenyl)carbonyl]-4-[1,6-dimethyl-4-(trifluoromethyl)-2-oxo-3-pyridinyl]-L-phenylalanine ethyl ester.

29. A compound of claim 27 which is N-[(2,6-dichlorophenyl)carbonyl]-4-[1,4-dimethyl-6-(trifluoromethyl)-2-oxo-3-pyridinyl]-L-phenylalanine ethyl ester.

30. A compound of claim 27 which is N-[(2-chloro-6-methylphenyl)carbonyl]-4-[1,6-dimethyl-4-(trifluoromethyl)-2-oxo-3-pyridinyl]-L-phenylalanine ethyl ester.

31. A compound of claim 27 which is N-[(2-chloro-6-methylphenyl)carbonyl]-4-[1,4-dimethyl-6-(trifluoromethyl)-2-oxo-3-pyridinyl]-L-phenylalanine ethyl ester.

32. A compound of claim 23 wherein $R_6$ is lower alkylcarbonyloxy lower alkyl.

33. A compound of claim 32 which is N-[(2,6-dichlorophenyl)carbonyl]-4-[1,6-dimethyl-4-(trifluoromethyl)-2-oxo-3-pyridinyl]-L-phenylalanine 1-(acetoxy)ethyl ester.

34. A compound of claim 32 which is N-[(2,6-dichlorophenyl)carbonyl]-4-[1,4-dimethyl-6-(trifluoromethyl)-2-oxo-3-pyridinyl]-L-phenylalanine 1-(acetoxy)ethyl ester.

35. A compound of claim 32 which is N-[(2-chloro-6-methylphenyl)carbonyl]-4-[1,6-dimethyl-4-(trifluoromethyl)-2-oxo-3-pyridinyl]-L-phenylalanine 1-(acetoxy)ethyl ester.)

36. A compound of claim 32 which is N-[(2-chloro-6-methylphenyl)carbonyl]-4-[1,4-dimethyl-6-(trifluoromethyl)-2-oxo-3-pyridinyl]-L-phenylalanine 1-(acetoxy)ethyl ester.

37. A compound of claim 23 wherein $R_6$ is a group of formula P-3 wherein $R_{32}$ is hydrogen; $R_{33}$ and $R_{34}$ are lower alkyl; one of g and h is 1 and the other is 0.

38. A compound of claim 37 which is N-[(2,6-dichlorophenyl)carbonyl]-4-[1,6-dimethyl-4-(trifluoromethyl)-2-oxo-3-pyridinyl]-L-phenylalanine 2-[(N,N-diethyl)amino]ethyl ester.

39. A compound of claim 37 which is N-[(2,6-dichlorophenyl)carbonyl]-4-[1,4-dimethyl-6-(trifluoromethyl)-2-oxo-3-pyridinyl]-L-phenylalanine 2-[(N,N-diethyl)amino]ethyl ester.

40. A compound of claim 37 which is N-[(2-chloro-6-methylphenyl)carbonyl]-4-[1,6-dimethyl-4-(trifluoromethyl)-2-oxo-3-pyridinyl]-L-phenylalanine 2-[(N,N-diethyl)amino]ethyl ester.

41. A compound of claim 37 which is N-[(2-chloro-6-methylphenyl)carbonyl]-4-[1,4-dimethyl-6-(trifluoromethyl)-2-oxo-3-pyridinyl]-L-phenylalanine 2-[(N,N-diethyl)amino]ethyl ester.

42. A compound of claim 22 wherein $R_6$ is hydrogen.

43. A compound of claim 42 wherein $R_2$ is lower alkyl; $R_3$ is hydrogen; $R_4$ is hydrogen or halogen; and $R_5$ is hydrogen or lower alkyl.

44. A compound of claim 43 wherein $R_1$ is Y-1.

45. A compound of claim 44 wherein $R_{22}$ and $R_{23}$ are lower alkyl or halogen, and $R_{24}$ is hydrogen.

46. A compound of claim 45 which is N-[(2-chloro-6-methylphenyl)carbonyl]-4-(5-chloro-1-methyl-2-oxo-3-pyridinyl)-L-phenylalanine.

47. A compound of claim 45 which is N-[(2-chloro-6-methylphenyl)carbonyl]-4-(1-methyl-2-oxo-3-pyridinyl)-L-phenylalanine.

48. A compound of claim 45 which is N-[(2-chloro-6-methylphenyl)carbonyl]-4-(1,4-dimethyl-2-oxo-3-pyridinyl)-L-phenylalanine.

49. A compound of claim 44 wherein $R_{22}$ and $R_{23}$ are halogen, and $R_{24}$ is hydrogen.

50. A compound of claim 49 which is N-[(2,6-dichlorophenyl)carbonyl]-4-(1,4-dimethyl-2-oxo-3-pyridinyl)-L-phenylalanine.

51. A compound of claim 44 wherein $R_{22}$ and $R_{23}$ are halogen or hydrogen and $R_{24}$ is lower alkoxy.

52. A compound of claim 51 which is N-[(2-bromo-5-methoxyphenyl)carbonyl]-4-(1-methyl-2-oxo-3-pyridinyl)-L-phenylalanine.

53. A compound of claim 51 which is N-[(2-bromo-5-methoxyphenyl)carbonyl]-4-(5-bromo-1-methyl-2-oxo-3-pyridinyl)-L-phenylalanine.

54. A compound of claim 43 wherein $R_1$ is Y-3.

55. A compound of claim 54 which is 4-(5-chloro-1-methyl-2-oxo-3-pyridinyl)-N-[[1-(2-methoxyethyl)cyclopentyl]carbonyl]-L-phenylalanine.

56. A compound of claim 21 wherein $R_{22}$ and $R_{23}$ are halogen or lower alkyl, $R_{24}$ is hydrogen or lower alkoxy, $R_{25}$ is a group of formula $R_{26}$—$(CH_2)_e$—, wherein $R_{26}$ is lower alkoxy, Q is —$(CH_2)_f$—, e is an integer from 0 to 4 and f is an integer from 0 to 3.

57. A compound of claim 56 wherein $R_2$ is aryl lower alkyl; $R_3$ is hydrogen, $R_4$ is halogen, and $R_5$, $R_6$ and $R_7$ are hydrogen.

58. A compound of claim 57 wherein $R_1$ is Y-1.

59. A compound of claim 58 which is 4-(1-Benzyl-5-chloro-2-oxo-3-pyridinyl)-N-[(2-chloro-6-methylphenyl)carbonyl]-L-phenylalanine.

60. A compound of claim 57 wherein $R_1$ is Y-3.

61. A compound of claim 60 which is 4-(1-Benzyl-5-chloro-2-oxo-3-pyridinyl)-N-[[1-(2-methoxyethyl)cyclopentyl]carbonyl]-L-phenylalanine.

\* \* \* \* \*